(12) United States Patent
Lauterbach et al.

(10) Patent No.: US 10,973,892 B2
(45) Date of Patent: Apr. 13, 2021

(54) METHODS AND COMPOSITIONS FOR ENHANCING VACCINE IMMUNE RESPONSES

(71) Applicant: Bavarian Nordic A/S, Kvistgaard (DK)

(72) Inventors: Henning Lauterbach, Echinq (DE); Hubertus Hochrein, Munich (DE)

(73) Assignee: Bavarian Nordic A/S, Kvistgaard (DK)

( * ) Notice: Subject to any disclaimer, the term of this patent is extended or adjusted under 35 U.S.C. 154(b) by 0 days.

(21) Appl. No.: 14/425,585

(22) PCT Filed: Mar. 15, 2013

(86) PCT No.: PCT/EP2013/055481
§ 371 (c)(1),
(2) Date: Mar. 3, 2015

(87) PCT Pub. No.: WO2014/037124
PCT Pub. Date: Mar. 13, 2014

(65) Prior Publication Data
US 2015/0202272 A1 Jul. 23, 2015

Related U.S. Application Data

(60) Provisional application No. 61/734,875, filed on Dec. 7, 2012, provisional application No. 61/696,764, filed on Sep. 4, 2012.

(51) Int. Cl.
*A61K 39/00* (2006.01)
*A61K 39/12* (2006.01)

(52) U.S. Cl.
CPC .......... *A61K 39/0011* (2013.01); *A61K 39/00* (2013.01); *A61K 39/0005* (2013.01); *A61K 39/00117* (2018.08); *A61K 39/001102* (2018.08); *A61K 39/001103* (2018.08); *A61K 39/001106* (2018.08); *A61K 39/001112* (2018.08); *A61K 39/001113* (2018.08); *A61K 39/001119* (2018.08); *A61K 39/001124* (2018.08); *A61K 39/001128* (2018.08); *A61K 39/001129* (2018.08); *A61K 39/001132* (2018.08); *A61K 39/001134* (2018.08); *A61K 39/001135* (2018.08); *A61K 39/001138* (2018.08); *A61K 39/001144* (2018.08); *A61K 39/001152* (2018.08); *A61K 39/001156* (2018.08); *A61K 39/001157* (2018.08); *A61K 39/001161* (2018.08); *A61K 39/001162* (2018.08); *A61K 39/001164* (2018.08); *A61K 39/001171* (2018.08); *A61K 39/001172* (2018.08); *A61K 39/001176* (2018.08); *A61K 39/001181* (2018.08); *A61K 39/001182* (2018.08); *A61K 39/001184* (2018.08); *A61K 39/001186* (2018.08); *A61K 39/001188* (2018.08); *A61K 39/001189* (2018.08); *A61K 39/001191* (2018.08); *A61K 39/001192* (2018.08); *A61K 39/001194* (2018.08); *A61K 39/001195* (2018.08); *A61K 39/001197* (2018.08); *A61K 39/12* (2013.01); *A61K 2039/5256* (2013.01); *A61K 2039/53* (2013.01); *A61K 2039/55516* (2013.01); *C12N 2710/24034* (2013.01); *C12N 2710/24143* (2013.01); *C12N 2760/14134* (2013.01); *Y02A 50/30* (2018.01)

(58) Field of Classification Search
None
See application file for complete search history.

(56) References Cited

U.S. PATENT DOCUMENTS

| 2011/0027309 A1* | 2/2011 | Bottje | A61K 39/0275 424/200.1 |
|---|---|---|---|
| 2011/0135683 A1* | 6/2011 | Chaplin | C12N 7/00 424/199.1 |
| 2011/0274649 A1 | 11/2011 | Kupper et al. | |
| 2012/0076820 A1* | 3/2012 | Amara | A61K 39/21 424/205.1 |
| 2014/0127252 A1* | 5/2014 | Deisseroth | C07K 14/005 424/190.1 |

FOREIGN PATENT DOCUMENTS

| WO | WO 03/074712 A1 | 9/2003 | |
| WO | WO-2013038066 | * 3/2013 | ............ A61K 35/76 |

OTHER PUBLICATIONS

Paoletti, PNAS USA, 1996, 93:11349-11353.*
Hanke et al., Journal of General Virology, 1998, 79 (Pt 1):83-90.*
Nials et al., Disease Models & Mechanisms, 2008, 1:213-220. (Year: 2008).*
Adamina et al. "Heterologous prime-boost immunotherapy of melanoma patients with Influenza virosomes . . . " Contemporary Clinical Trials, Elsevier GB vol. 29: 165-181 (2008).
Litzinger et al. "Comparative analysis of MVA-CD40L and MVA-TRICOM vectors for enhancing . . . " Leukemia Research, vol. 34 (10): 1351-57 (2010).
Feder-Mengus et al. "Nonreplicating Recombinant Vaccinia virus expressing CD40 Ligand enhances . . . " Human Gene Therapy, vol. 16: 348-360 (2005).
Liu J et al. "CD40L expressed from the canarypox vector, ALVAC, can boost immunogenclity of HIV-1 . . . " Vaccine, vol. 26:4062-4072 (2008).
Ruby et al. "CD40 ligand has potent antiviral activity." Nature Medicine vol. 1: 437-441 (1995).

(Continued)

Primary Examiner — Nicole Kinsey White

(57) ABSTRACT

Provided herein are immunogenic compositions comprising a recombinant modified vaccinia virus Ankara (MVA) comprising a nucleic acid sequence encoding a CD40 ligand (CD40L) and a nucleic acid sequence encoding a heterologous disease-associated antigen, wherein the immunogenic composition induces increases T-cell immune responses specific for the heterologous disease-associated antigen when administered to a human host, and related methods and uses.

15 Claims, 18 Drawing Sheets

Specification includes a Sequence Listing.

(56) References Cited

OTHER PUBLICATIONS

Rolph et al. "Recombinant Viruses as vaccines and immunological tools." Current Opinion in Immunology, vol. 9: 517-524 (1997).
Oxenius et al. "CD40-CD40 ligand interactions are critical T-B Cooperation . . . " J. Exp. Med. vol. 183: 2209-2218 (1996).
McFadden et al. "Getting to know you: Viruses meet CD40 ligand." Nature Medicine, vol. 1: 437-441 (1995).
Kurche et al. "Comparison of OX40 ligand and CD70 in the promotion of CD4 T cell responses" J Immunol 185: 2106-2115 (2010).
Hodge et al. "Enhanced Activation of T cells by Dendritic cells . . . " Journal of the National Cancer Institute, vol. 92: 1228-39 (2000).
Gomez et al. "Multimeric soluble CD40 ligand (sCD40L) efficiently enhances HIV . . . " Vaccine, vol. 27: 3165-3174 (2009).
Cella et al. "Ligation of CD40 on Dendritic Cells Triggers Production of High Levels . . . " J. Exp. Med. vol. 184: 747-752 (1996).
Bereta et al. "Immune properties of recombinant vaccinia virus encoding CD154 (CD40L) . . . " Cancer Gene Therapy, vol. 11:808-818 (2004).
Ahlers et al. "A push-pull approach to maximize vaccine efficacy: Abrogating suppression with an IL-13 inhibitor . . . " PNAS, vol. 99:13020-25 (2002).
Spehner et al. "Extracellular vesicles containing virus-encoded membrane proteins . . . " Virus Research 137: 129-136 (2008).
Zheng et al. "CD4+ T cell-independent DNA vaccination against opportunistic infections" J. Clin. Invest. 115: 3536-44 (2005).
Peng et al. "In vivo gene transfer of CD40 ligand into colon cancer cells induces local production of cytokines . . . " Gene Therapy, 7: 1467-76 (2000).
Schmitz et al. "Adenovirus-Mediated CD40 Ligand Gene Therapy in a Rat Model of Orthotopic Hepatocellular Carcinoma" Hepatology, 34: 72-81 (2001).
Peter et al, "Immunotherapy for murine K1735 melanoma: Combinatorial use of recombinant adenovirus expressing CD40L . . . " Cancer Gene Therapy, 9:597-605 (2002).
Kikuchi et al. "Tumor Regression Induced by Intratumor Administration of Adenovirus Vector Expressing CD40 Ligand . . . " Cancer Res 60: 6391-95 (2000).
Lida et al. "Adenovirus-mediated CD40L gene therapy induced both humoral and cellular immunity . . . " Cancer Sci 99: 2097-2103 (2008).
Hanyu et al. "immunogene Therapy by Adenovirus Vector Expressing CD40 Ligand for Metastatic Liver Cancer in Rats" Anticancer Res 28:2785-2790 (2008).
Tripp et al. "CD40 Ligand (CD154) Enhances the Th1 and Antibody Responses . . . " J Immunol 164: 5913-5921 (2000).
Loskog et al. "Adenovirus CD40 Ligand Gene Therapy Counteracts Immune Escape Mechanisms . . . " J Immunol. 172: 7200-7205 (2004).
Friedlander et al. "Efficacy of CD40 Ligand Gene Therapy in Malignant Mesothelioma" Am J. Respir Cell Mol Biol., 29; 321-330 (2003).
International Search Report and Written Opinion of the International Search Authority for PCT/EP2013/055481, dated Jun. 27, 2013.
European Office Communication for EP 13717720.0 (PCT application PCT/EP2013/055481) dated Apr. 28, 2016.
Kwa et al., "CD40L-Adjuvanted DNA/Modified Vaccinia Virus Ankara Simian Immunodeficiency Virus SIV239 Enhances SIV-Specific Humoral and Cellular Immunity . . . ," 2014, pp. 9579-9589, vol. 88.

* cited by examiner

SEQUENCE LISTING

```
<160> NUMBER OF SEQ ID NOS: 5

<210> SEQ ID NO 1
<211> LENGTH: 260
<212> TYPE: PRT
<213> ORGANISM: Murine
<220> FEATURE:
<221> NAME/KEY: misc_feature
<222> LOCATION: (1)..(260)
<223> OTHER INFORMATION: Amino acid sequence of mouse CD40L (Accession
      No. NM_011616.2)

<400> SEQUENCE: 1

Met Ile Glu Thr Tyr Ser Gln Pro Ser Pro Arg Ser Val Ala Thr Gly
1               5                   10                  15

Leu Pro Ala Ser Met Lys Ile Phe Met Tyr Leu Leu Thr Val Phe Leu
            20                  25                  30

Ile Thr Gln Met Ile Gly Ser Val Leu Phe Ala Val Tyr Leu His Arg
        35                  40                  45

Arg Leu Asp Lys Val Glu Glu Glu Val Asn Leu His Glu Asp Phe Val
    50                  55                  60

Phe Ile Lys Lys Leu Lys Arg Cys Asn Lys Gly Glu Gly Ser Leu Ser
65                  70                  75                  80

Leu Leu Asn Cys Glu Glu Met Arg Arg Gln Phe Glu Asp Leu Val Lys
                85                  90                  95

Asp Ile Thr Leu Asn Lys Glu Glu Lys Lys Glu Asn Ser Phe Glu Met
            100                 105                 110

Gln Arg Gly Asp Glu Asp Pro Gln Ile Ala Ala His Val Val Ser Glu
        115                 120                 125

Ala Asn Ser Asn Ala Ala Ser Val Leu Gln Trp Ala Lys Lys Gly Tyr
    130                 135                 140

Tyr Thr Met Lys Ser Asn Leu Val Met Leu Glu Asn Gly Lys Gln Leu
145                 150                 155                 160
```

```
Thr Val Lys Arg Glu Gly Leu Tyr Tyr Val Tyr Thr Gln Val Thr Phe
            165                 170                 175

Cys Ser Asn Arg Glu Pro Ser Ser Gln Arg Pro Phe Ile Val Gly Leu
            180                 185                 190

Trp Leu Lys Pro Ser Ser Gly Ser Glu Arg Ile Leu Leu Lys Ala Ala
            195                 200                 205

Asn Thr His Ser Ser Ser Gln Leu Cys Glu Gln Gln Ser Val His Leu
            210                 215                 220

Gly Gly Val Phe Glu Leu Gln Ala Gly Ala Ser Val Phe Val Asn Val
225                 230                 235                 240

Thr Glu Ala Ser Gln Val Ile His Arg Val Gly Phe Ser Ser Phe Gly
            245                 250                 255

Leu Leu Lys Leu
            260

<210> SEQ ID NO 2
<211> LENGTH: 261
<212> TYPE: PRT
<213> ORGANISM: Human
<220> FEATURE:
<221> NAME/KEY: misc_feature
<222> LOCATION: (1)..(261)
<223> OTHER INFORMATION: Amino acid sequence of human CD40L (Accession
      No. NM_000074.2)

<400> SEQUENCE: 2

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240
```

```
Val Thr Asp Pro Ser Gln Val Ser His Gly Thr Gly Phe Thr Ser Phe
            245                 250                 255

Gly Leu Leu Lys Leu
            260

<210> SEQ ID NO 3
<211> LENGTH: 8
<212> TYPE: PRT
<213> ORGANISM: Artificial
<220> FEATURE:
<223> OTHER INFORMATION: MVA-derived B820-27-peptide

<400> SEQUENCE: 3

Thr Ser Tyr Lys Phe Glu Ser Val
1               5

<210> SEQ ID NO 4
<211> LENGTH: 8
<212> TYPE: PRT
<213> ORGANISM: Artificial
<220> FEATURE:
<223> OTHER INFORMATION: Ovalbumin-derived OVA257-264-peptide

<400> SEQUENCE: 4

Ser Ile Ile Asn Phe Glu Lys Leu
1               5

<210> SEQ ID NO 5
<211> LENGTH: 8
<212> TYPE: PRT
<213> ORGANISM: Artificial
<220> FEATURE:
<223> OTHER INFORMATION: Ebola Virus-Zaire glycoprotein derived ZEBOV-
      GP577-584-peptide

<400> SEQUENCE: 5

Thr Glu Leu Arg Thr Phe Ser Ile
1               5
```

US 10,973,892 B2

METHODS AND COMPOSITIONS FOR ENHANCING VACCINE IMMUNE RESPONSES

This application is a National Phase application under 35 U.S.C. § 371 of International Application No. PCT/EP2013/055481, filed Mar. 15, 2013, and claims the benefit under 35 U.S.C. § 119(e) of U.S. Provisional Patent Application 61/734,875 filed Dec. 7, 2012 and U.S. Provisional Patent Application 61/696,764 filed Sep. 4, 2012, the disclosures of which are incorporated by reference herein in their entirety.

FIELD

The present invention relates to immunogenic compositions comprising a recombinant modified vaccinia virus Ankara (MVA) comprising a nucleic acid sequence encoding a CD40 ligand (CD40L) and a nucleic acid sequence encoding a heterologous disease-associated antigen, wherein the immunogenic composition induces increases T-cell immune responses specific for the heterologous disease-associated antigen when administered to a human host, and to related methods and uses.

BACKGROUND

Decades of successful vaccine development led to a drastic reduction in child mortality and debilitating illness resulting from infectious disease, although a substantial unmed medical need remains. Despite this impressive success, probably best exemplified by the eradication of smallpox, an estimated 5.6 million deaths annually can attributed solely to the three most devastating infectious diseases: malaria, tuberculosis, and human immunodeficiency virus/acquired immune deficiency syndrome ("HIV/AIDS") [World Health Organization, World Health Report 2004: Changing history. Geneva: World Health Organization. Available at http://www.who.int/whr/2004/en]. Other infectious diseases, such as Ebola and Marburg hemorrhagic fever, are quite rare but accompanied by high fatality rates. Moreover, the corresponding viruses might be used as bioterrorism agents. The common element linking these very diverse diseases is the requirement for strong T-cell responses as part of the adaptive immune response to protect the host from infection. Because it is generally accepted that an ideal vaccine should induce both T-cells and antibodies (i.e., both T-cell and B-cell responses), modern vaccinology is faced with the challenge to create a safe vaccine able to activate efficiently both arms of the adaptive immune system.

Progress in the vaccine arts has also led to the development of active immunotherapies for the treatment of various types of cancer. Unlike preventive vaccines for infectious disease, development of a successful cancer vaccine requires the identification of specific tumor-associated antigens characteristic of particular types of cancer and the ability to break self-tolerance so that the patient's immune system can recognize and attack cancer cells expressing the tumor-associated antigen. Like vaccines for infectious disease, however, it is thought that cancer vaccines must also induce a strong T-cell response as part of the tumor-specific adaptive immune response to treat the disease, as well as a robust antibody response (i.e., both T-cell and B-cell responses). While the first cancer vaccine was approved by the US Food & Drug Administration in 2011, there remains a substantial unmet medical need for effective oncology therapeutics lacking the side effects typically associated with chemotherapeutics.

Among the many possible vaccine modalities, live vector viruses seem best to fulfill the requirement for inducing both T-cell and B-cell responses [R. A. Koup and D. C. Douek, "Vaccine Design for CD8+ T Lymphocyte Responses," *Cold Spring Harb. Perspect. Med.* 2011; 1:a007252]. While some live virus vaccines, such as vaccinia virus and yellow fever virus are effective but have unfavorable safety profiles, others, such as adenovirus, face problems due to preexisting immunity [A. R. Thorner, et al., "Age Dependence of Adenovirus-Specific Neutralizing Antibody Titers in Individuals from Sub-Saharan Africa," *J. Clin. Microbiol.* 44(10):3781-3783 (2006)]. A safe live vector vaccine unaffected by preexisting immunity is modified vaccinia virus Ankara (MVA), originally created by Anton Mayr and further developed into a third-generation smallpox vaccine (MVA-BN®) [Z. Wang et al., "Recombinant Modified Vaccinia Virus Ankara Expressing a Soluble Form of Glycoprotein B Causes Durable Immunity and Neutralizing Antibodies against Multiple Strains of Human Cytomegalovirus," *J. Virol.* 78(8):3965-3976 (2004)].

The excellent safety profile of MVA, because of its replication deficiency in human cells, has been proven in many clinical trials, including vaccination of immune-compromised individuals, and during the smallpox eradication campaign in the 1970s, when 120,000 people were vaccinated with MVA [A. Mayr et al., "The smallpox vaccination strain MVA: marker, genetic structure, experience gained with the parenteral vaccination and behavior in organisms with a debilitated defense mechanism," *Zentralbl. Bakteriol. B* 167 (5-6):375-390 (1978)]. Since then, many different recombinant MVA vaccines have been generated and tested for the ability to immunize animals and humans against infectious (e.g., HIV, malaria) and non-infectious (e.g., prostate cancer) diseases. Its proven safety and good immunogenicity thus make MVA a prime candidate for a T- and B-cell-inducing vaccine vector.

Classically, vaccine development has focused on the induction of neutralizing antibodies. In recent years, however, T-cells, especially CD8+ T-cells, have moved into the focus of vaccinologists. This paradigm shift stems from an increasing amount of data showing the need for high amounts of multi-functional CD8+ T-cells to clear or protect against pathogens such as HIV, simian immune deficiency virus ("SIV"), Ebola virus, human papillomavirus ("HPV"), hepatitis C virus ("HCV") and *P. falciparum*, the causative agent of malaria. Furthermore, adoptive transfer experiments have demonstrated the therapeutic potential of CD8+ T-cells in treating cancer. This increased awareness of the importance of CD8+ T-cells has spurred more basic science aimed at better understanding T-cell biology. Even though not all factors and mechanisms governing cytotoxic T-lymphocyte ("CTL") expansion and memory differentiation are understood in all details, it is believed that expansion, development of effector functions, and ultimately, differentiation into CD8+ memory T-cells are mainly determined during the first few days after antigen encounter. In a simplistic view, antigen recognition via the T-cell receptor ("TCR")(signal 1) activates the T-cell, co-stimulation via CD28 and CD80/CD86 (signal 2), and the secretion of cytokines such as interleukin-12 ("IL-12") and interferon-alpha ("IFN-α")(signal 3) ensure the efficient generation of effector and memory CTLs. However, after pathogen encounter, a plethora of additional stimulatory and inhibitory molecules are induced, creating a specific inflammatory environment, which further influences quality and quantity of CTL responses [P. Wong & E. G. Pamer, "CD8+ T-cell responses to infectious pathogens," *Ann. Rev. Immunol.* 21:29-70 (2003); E-pub. Dec. 19, 2001].

Among those molecules, members of the tumor necrosis factor receptor/tumor necrosis factor ("TNFR/TNF") superfamily are well known for their T-cell shaping properties. This family includes, among others, CD27/CD70, CD30/CD30L, CD40/CD40L, OX40/OX40L, 4-1BB/4-1BBL, GITR/GITRL and Fas/FasL. The role of CD70, OX40L and 4-1BBL for primary and secondary T-cell responses has been investigated in a broad range of infectious disease models [Hendrick et al., "CD27 is required for generation and long-term maintenance of T-cell immunity," *Nature Immunol.* 1(5):433-440 (2000); Matter et al., "Virus-induced polyclonal B-cell activation improves protective CTL memory via retained CD27 expression on memory CTL," *Eur. J. Immunol.* 35(11):3229-3239 (2005); A. Schildknecht et al., "Priming of CD8+ T-cell responses by pathogens typically depends on CD70-mediated interactions with dendritic cells," *Eur. J. Immunol.* 37(3):716-728 (2007)]. Interestingly, the up-regulation of co-stimulatory molecules (including CD80, CD86, CD70, 4-1BBL and OX40L) on dendritic cells ("DCs") can be induced by combined TLR/CD40 stimulation [Sanchez et al., "Combined TLR/CD40 stimulation mediates potent cellular immunity by regulating dendritic cell expression of CD70 in vivo," *J. Immunol.* 178(3):1564-1572 (2007)]. Furthermore, TLR/CD40 ligation also induces the expression of pro-inflammatory cytokines, including IL-12p70, by DCs in vivo [Schulz et al., "CD40 triggering of IL-12p70 production by dendritic cells in vivo requires a microbial priming signal," *Immunity* 13(4):453-462 (2000)]. Thus, CD40 can be regarded as a master-switch for DC activation. While CD40 is constitutively expressed on many cell types, including B-cells, macrophages and DCs, its ligand CD40L is predominantly expressed on activated CD4+ T-cells [Lee et al., "CD4−, but not CD154, expression on B-cells is necessary for optimal primary B-cell responses," *J. Immunol.* 171(11):5707-5717 (2002); D. Y. Ma and E. A. Clark, "The role of CD40 and CD154/CD40L in dendritic cells," *Semin. Immunol.* 21(5): 265-272 (2009)]. The cognate interaction between DCs and CD4+ T-cells early after infection or immunization 'licenses' DCs to prime CD8+ T-cell responses [J. P. Ridge et al., "A conditioned dendritic cell can be a temporal bridge between a CD4+ T-helper and a T-killer cell," *Nature* 393(6684):474-478 (1998)]. DC licensing results in the upregulation of co-stimulatory molecules, increased survival and better cross-presenting capabilities of DCs. This process is mainly mediated via CD40/CD40L interaction [S. R. Bennet et al., "Help for cytotoxic T-cell responses is mediated by CD40 signalling," *Nature* 393(6684):478-480 (1998); S. P. Schoenberger et al., "T-cell help for cytotoxic T-cell help is mediated by CD40-CD40L interactions," *Nature* 393(6684):480-483 (1998)], but CD40/CD40L-independent mechanisms also exist (CD70, LTβR). Interestingly, a direct interaction between CD40L expressed on DCs and CD40 on expressed on CD8+ T-cells has also been suggested, providing a possible explanation for the generation of helper-independent CTL responses [S. Johnson et al., "Selected Toll-like receptor ligands and viruses promote helper-independent cytotoxic T-cell priming by upregulating CD40L on dendritic cells," *Immunity* 30(2):218-227 (2009)].

Several studies indicate that agonistic anti-CD40 antibodies may be useful as a vaccine adjuvant. In addition, recombinant AdV [K. Kato et al., "Gene transfer of CD40-ligand induces autologous immune recognition of chronic lymphocytic leukemia B-cells," *J. Clin. Invest.* 101(5):1133-1141 (1998)] and VV [Bereta et al., "Immune properties of recombinant vaccinia virus encoding CD154 (CD40L) are determined by expression of virally encoded CD40L and the presence of CD40L protein in viral particles," *Cancer Gen. Ther.* 11(12):808-818 (2004)] encoding CD40L have been created that showed superior immunogenicity in vitro and in vivo compared to non-adjuvanted viruses. Based on these data, the central role of CD40/CD40L co-stimulation for CD8+ T-cell responses and the good CTL-inducing capacities of MVA together with its favorable safety profile, we constructed a recombinant MVA expressing CD40L and the model antigen ovalbumin (OVA). In vitro and in vivo analyses revealed significantly enhanced DC activation and cytokine production (including high levels of IL-12p70) after treating cells or mice with MVA-OVA-CD40L. This effect was entirely dependent on de novo gene expression, partly contradicting previous results [Bereta et al., (2004)]. While we could not detect any influence on antibody responses, immunization with MVA-OVA-CD40L led to strongly enhanced primary and memory CD8+ T-cell responses. Of note, one immunization with MVA-OVA-CD40L induced the same number of CTL as two immunizations with MVA-OVA. Importantly, not only the quantity but also the quality of the CTL response was improved, as revealed by intracellular cytokine staining and in vivo killing activity. Finally, the superior T-cell response directly translated into better protection against a fatal virus infection in B-cell-deficient mice. These results highlight the potential of a CD40L-adjuvanted MVA rapidly to induce strong antigen-specific multi-functional CD8+ T-cell responses. Thus, recombinant MVA-CD40L is a prime candidate vector for the development of prophylactic and therapeutic vaccines against diseases such as cancer, HIV/AIDS, Ebola and Marburg hemorrhagic fever, malaria, hepatitis C and other infectious diseases.

SUMMARY OF THE INVENTION

In one aspect, provided herein are immunogenic compositions comprising a recombinant modified vaccinia virus Ankara (MVA) comprising a nucleic acid sequence encoding a CD40 ligand (CD40L) and a nucleic acid sequence encoding a heterologous disease-associated antigen, wherein the immunogenic composition induces increased T-cell immune responses specific for the heterologous disease-associated antigen when administered to a human host. In certain embodiments, the increased T-cell immune response comprises greater numbers of cytotoxic T-cells (CTLs) specific for the heterologous disease-associated antigen. In certain embodiments, the greater numbers of CTLs specific for the heterologous disease-associated antigen also display increased cytolytic activity compared to CTLs induced by administration of a recombinant MVA comprising a nucleic acid sequence encoding a heterologous disease-associated antigen but not a nucleic acid sequence encoding a CD40L. In certain embodiments, the increased T-cell immune response comprises greater numbers of memory T-cells specific for the heterologous disease-associated antigen. In certain embodiments, the increased T-cell immune response comprises greater numbers of CTLs specific for the heterologous disease-associated antigen and greater numbers of memory T-cells specific for the heterologous disease-associated antigen. In certain embodiments, the greater numbers of CTLs specific for the heterologous disease-associated antigen also display increased cytolytic activity compared to CTLs induced by administration of a recombinant MVA comprising a nucleic acid sequence encoding a heterologous disease-associated antigen but not a nucleic acid sequence encoding a CD40L.

In certain embodiments, the nucleic acid sequence encodes a CD40L having at least 95%, 96%, 97%, 98%, 99%, or 100% amino acid sequence identity to SEQ ID NO:1. In certain embodiments, the nucleic acid sequence encodes a CD40L having the amino acid sequence of SEQ ID NO:1. In certain embodiments, the nucleic acid sequence encodes a CD40L having at least 95%, 96%, 97%, 98%, 99%, or 100% amino acid sequence identity to SEQ ID NO:2. In certain embodiments, the nucleic acid sequence encodes a CD40L having the amino acid sequence of SEQ ID NO:2. In certain embodiments, the immunogenic composition further comprises a pharmaceutically acceptable carrier.

In certain embodiments, the disease-associated antigen is an infectious disease antigen or a tumor-associated antigen. In certain embodiments, the disease-associated antigen is an infectious disease antigen. In certain embodiments, the infectious disease antigen is a viral antigen, a bacterial antigen, a fungal antigen, or a parasite antigen.

In certain embodiments, the infectious disease antigen is a viral antigen. In certain embodiments, the viral antigen is derived from a virus selected from the group consisting of adenovirus, Coxsackievirus, Crimean-Congo hemorrhagic fever virus, cytomegalovirus ("CMV"), dengue virus, Ebola virus, Epstein-Barr virus ("EBV"), Guanarito virus, herpes simplex virus-type 1 ("HSV-1"), herpes simplex virus-type 2 ("HSV-2"), human herpesvirus-type 8 ("HHV-8"), hepatitis A virus ("HAV"), hepatitis B virus ("HBV"), hepatitis C virus ("HCV"), hepatitis D virus ("HDV"), hepatitis E virus ("HEV"), human immunodeficiency virus ("HIV"), influenza virus, Junin virus, Lassa virus, Machupo virus, Marburg virus, measles virus, human metapneumovirus, mumps virus, Norwalk virus, human papillomavirus ("HPV"), parainfluenza virus, parvovirus, poliovirus, rabies virus, respiratory syncytial virus ("RSV"), rhinovirus, rotavirus, rubella virus, Sabia virus, severe acute respiratory syndrome virus ("SARS"), varicella zoster virus, variola virus, West Nile virus, and yellow fever virus.

In certain embodiments, the infectious disease antigen is a bacterial antigen. In certain embodiments, the bacterial antigen is derived from a bacterium selected from the group consisting of *Bacillus anthracis, Bordetella pertussis, Borrelia burgdorferi, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diptheriae, Enterococcus faecalis, Enterococcus faecium, Escherichia coli,* enterotoxigenic *Escherichia coli,* enteropathogenic *Escherichia coli, Escherichia coli*) 157:117, *Francisella tularensis, Haemophilus influenza, Helicobacter pylori, Legionella pneumophila, Leptospira interrogans, Listeria monocytogenes, Mycobacterium leprae, Mycobacterium tuberculosis, Mycoplasma pneumoniae, Neisseria gonorrhoeae, Neisseria meningitides, Pseudomonas aeruginosa, Rickettsia rickettsia, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholerae,* and *Yersinia pestis.*

In certain embodiments, the infectious disease antigen is a fungal antigen. In certain embodiments, the fungal antigen is derived from a fungus selected from the group consisting of *Aspergillus clavatus, Aspergillus flavus, Aspergillus fumigatus, Aspergillus nidulans, Aspergillus niger, Aspergillus terreus, Blastomyces dermatitidis, Candida albicans, Candida dubliniensis, Candida glabrata, Candida parapsilosis, Candida rugosa, Candida tropicalis, Cryptococcus albidus, Cryptococcus gattii, Cryptococcus laurentii, Cryptococcus neoformans, Histoplasma capsulatum, Microsporum canis, Pneumocystis carinii, Pneumocystis jirovecii, Sporothrix schenckii, Stachbotrys chartarum, Tinea barbae, Tinea captitis, Tinea corporis, Tinea cruris, Tinea faciei, Tinea incognito, Tinea nigra, Tinea versicolor, Trichophyton rubrum* and *Trichophyton tonsurans.*

In certain embodiments, the infectious disease antigen is a parasite antigen. In certain embodiments, the parasite antigen is derived from a parasite selected from the group consisting of *Anisakis* spp. *Babesia* spp., *Baylisascaris procyonis, Cryptosporidium* spp., *Cyclospora cayetanensis, Diphyllobothrium* spp., *Dracunculus medinensis, Entamoeba histolytica, Giardia duodenalis, Giardia intestinalis, Giardia lamblia, Leishmania* sp., *Plasmodium falciparum, Schistosoma mansoni, Schistosoma haematobium, Schistosoma japonicum, Taenia* spp., *Toxoplasma gondii, Trichinella spiralis,* and *Trypanosoma cruzi.*

In certain embodiments, the disease-associated antigen is a tumor-associated antigen. In certain embodiments, the tumor-associated antigen is selected from the group consisting of 5-α-reductase, α-fetoprotein ("AFP"), AM-1, APC, April, B melanoma antigen gene ("BAGE"), β-catenin, Bcl12, bcr-abl, Brachyury, CA-125, caspase-8 ("CASP-8", also known as "FLICE"), Cathepsins, CD19, CD20, CD21/complement receptor 2 ("CR2"), CD22/BL-CAM, CD23/F$_c$εRII, CD33, CD35/complement receptor 1 ("CR1"), CD44/PGP-1, CD45/leucocyte common antigen ("LCA"), CD46/membrane cofactor protein ("MCP"), CD52/CAMPATH-1, CD55/decay accelerating factor ("DAF"), CD59/protectin, CDC27, CDK4, carcinoembryonic antigen ("CEA"), c-myc, cyclooxygenase-2 ("cox-2"), deleted in colorectal cancer gene ("DCC"), DcR3, E6/E7, CGFR, EMBP, Dna78, farnesyl transferase, fibroblast growth factor-8a ("FGF8a"), fibroblast growth factor-8b ("FGF8b"), FLK-1/KDR, folic acid receptor, G250, G melanoma antigen gene family ("GAGE-family"), gastrin 17, gastrin-releasing hormone, ganglioside 2 ("GD2")/ganglioside 3 ("GD3")/ganglioside-monosialic acid-2 ("GM2"), gonadotropin releasing hormone ("GnRH"), UDP-GlcNAc:R$_1$Man (α1-6)R$_2$ [GlcNAc to Man(α1-6)] β1,6-N-acetylglucosaminyltransferase V ("GnT V"), GP1, gp100/Pme117, gp-100-in4, gp15, gp75/tyrosine-related protein-1 ("gp75/TRP-1"), human chorionic gonadotropin ("hCG"), heparanase, Her2/neu, human mammary tumor virus ("HMTV"), 70 kiloDalton heat-shock protein ("HSP70"), human telomerase reverse transcriptase ("hTERT"), insulin-like growth factor receptor-1 ("IGFR-1"), interleukin-13 receptor ("IL-13R"), inducible nitric oxide synthase ("iNOS"), Ki67, KIAA0205, K-ras, H-ras, N-ras, KSA, LKLR-FUT, melanoma antigen-encoding gene 1 ("MAGE-1"), melanoma antigen-encoding gene 2 ("MAGE-2"), melanoma antigen-encoding gene 3 ("MAGE-3"), melanoma antigen-encoding gene 4 ("MAGE-4"), mammaglobin, MAP17, Melan-A/melanoma antigen recognized by T-cells-1 ("MART-1"), mesothelin, MIC A/B, MT-MMPs, mucin, testes-specific antigen NY-ESO-1, osteonectin, p15, P170/MDR1, p53, p97/melanotransferrin, PAI-1, platelet-derived growth factor ("PDGF"), µPA, PRAMS, probasin, progenipoietin, prostate-specific antigen ("PSA"), prostate-specific membrane antigen ("PSMA"), RAGE-1, Rb, RCAS1, SART-1, SSX-family, STAT3, STn, TAG-72, transforming growth factor-alpha ("TGF-α"), transforming growth factor-beta ("TGF-β"), Thymosin-beta-15, tumor necrosis factor-alpha ("TNF-α"), TP1, TRP-2, tyrosinase, vascular endothelial growth factor ("VEGF"), ZAG, p16INK4, and glutathione-S-transferase ("GST").

In another aspect, provided herein are methods of enhancing an antigen-specific immune response to a disease-associated antigen, comprising administering any one of the immunogenic compositions provided herein to a subject in need thereof, wherein the immunogenic composition induces increased T-cell immune responses specific for the heterologous disease-associated antigen when administered to a human host. In certain embodiments, the subject is a mammal. In certain embodiments, the mammal is a human. In certain embodiments, the increased T-cell immune response comprises greater numbers of cytotoxic T-cells (CTLs) specific for the heterologous disease-associated antigen. In certain embodiments, the greater numbers of CTLs specific for the heterologous disease-associated antigen also display increased cytolytic activity compared to CTLs induced by administration of a recombinant MVA comprising a nucleic acid sequence encoding a heterologous disease-associated antigen but not a nucleic acid sequence encoding a CD40L. In certain embodiments, the increased T-cell immune response comprises greater numbers of memory T-cells specific for the heterologous disease-associated antigen. In certain embodiments, the increased T-cell immune response comprises greater numbers of CTLs specific for the heterologous disease-associated antigen and greater numbers of memory T-cells specific for the heterologous disease-associated antigen. In certain embodiments, the greater numbers of CTLs specific for the heterologous disease-associated antigen also display increased cytolytic activity compared to CTLs induced by administration of a recombinant MVA comprising a nucleic acid sequence encoding a heterologous disease-associated antigen but not a nucleic acid sequence encoding a CD40L.

In certain embodiments, the nucleic acid sequence encodes a CD40L having at least 95%, 96%, 97%, 98%, 99%, or 100% amino acid sequence identity to SEQ ID NO:1. In certain embodiments, the nucleic acid sequence encodes a CD40L having the amino acid sequence of SEQ ID NO:1. In certain embodiments, the nucleic acid sequence encodes a CD40L having at least 95%, 96%, 97%, 98%, 99%, or 100% amino acid sequence identity to SEQ ID NO:2. In certain embodiments, the nucleic acid sequence encodes a CD40L having the amino acid sequence of SEQ ID NO:2. In certain embodiments, the immunogenic composition further comprises a pharmaceutically acceptable carrier.

In certain embodiments, the disease-associated antigen is an infectious disease antigen or a tumor-associated antigen. In certain embodiments, the disease-associated antigen is an infectious disease antigen. In certain embodiments, the infectious disease antigen is a viral antigen, a bacterial antigen, a fungal antigen, or a parasite antigen.

In certain embodiments, the infectious disease antigen is a viral antigen. In certain embodiments, the viral antigen is derived from a virus selected from the group consisting of adenovirus, Coxsackievirus, Crimean-Congo hemorrhagic fever virus, cytomegalovirus ("CMV"), dengue virus, Ebola virus, Epstein-Barr virus ("EBV"), Guanarito virus, herpes simplex virus-type 1 ("HSV-1"), herpes simplex virus-type 2 ("HSV-2"), human herpesvirus-type 8 ("HHV-8"), hepatitis A virus ("HAV"), hepatitis B virus ("HBV"), hepatitis C virus ("HCV"), hepatitis D virus ("HDV"), hepatitis E virus ("HEV"), human immunodeficiency virus ("HIV"), influenza virus, Junin virus, Lassa virus, Machupo virus, Marburg virus, measles virus, human metapneumovirus, mumps virus, Norwalk virus, human papillomavirus ("HPV"), parainfluenza virus, parvovirus, poliovirus, rabies virus, respiratory syncytial virus ("RSV"), rhinovirus, rotavirus, rubella virus, Sabia virus, severe acute respiratory syndrome virus ("SARS"), varicella zoster virus, variola virus, West Nile virus, and yellow fever virus.

In certain embodiments, the infectious disease antigen is a bacterial antigen. In certain embodiments, the bacterial antigen is derived from a bacterium selected from the group consisting of *Bacillus anthracis*, *Bordetella pertussis*, *Borrelia burgdorferi*, *Brucella abortus*, *Brucella canis*, *Brucella melitensis*, *Brucella suis*, *Campylobacter jejuni*, *Chlamydia pneumoniae*, *Chlamydia trachomatis*, *Chlamydophila psittaci*, *Clostridium botulinum*, *Clostridium difficile*, *Clostridium peringens*, *Clostridium tetani*, *Corynebacterium diptheriae*, *Enterococcus faecalis*, *Enterococcus faecium*, *Escherichia coli*, enterotoxigenic *Escherichia coli*, enteropathogenic *Escherichia coli*, *Escherichia coli*) 157: H7, *Francisella tularensis*, *Haemophilus influenza*, *Helicobacter pylori*, *Legionella pneumophila*, *Leptospira interrogans*, *Listeria monocytogenes*, *Mycobacterium leprae*, *Mycobacterium tuberculosis*, *Mycoplasma pneumoniae*, *Neisseria gonorrhoeae*, *Neisseria meningitides*, *Pseudomonas aeruginosa*, *Rickettsia rickettsia*, *Salmonella typhi*, *Salmonella typhimurium*, *Shigella sonnei*, *Staphylococcus aureus*, *Staphylococcus epidermidis*, *Staphylococcus saprophyticus*, *Streptococcus agalactiae*, *Streptococcus pneumoniae*, *Streptococcus pyogenes*, *Treponema pallidum*, *Vibrio cholerae*, and *Yersinia pestis*.

In certain embodiments, the infectious disease antigen is a fungal antigen. In certain embodiments, the fungal antigen is derived from a fungus selected from the group consisting of *Aspergillus clavatus*, *Aspergillus flavus*, *Aspergillus fumigatus*, *Aspergillus nidulans*, *Aspergillus niger*, *Aspergillus terreus*, *Blastomyces dermatitidis*, *Candida albicans*, *Candida dubliniensis*, *Candida glabrata*, *Candida parapsilosis*, *Candida rugosa*, *Candida tropicalis*, *Cryptococcus albidus*, *Cyptococcus gattii*, *Cryptococcus laurentii*, *Cryptococcus neoformans*, *Histoplasma capsulatum*, *Microsporum canis*, *Pneumocystis carinii*, *Pneumocystis jirovecii*, *Sporothrix schenckii*, *Stachbotys chartarum*, *Tinea barbae*, *Tinea captitis*, *Tinea corporis*, *Tinea cruris*, *Tinea faciei*, *Tinea incognito*, *Tinea nigra*, *Tinea versicolor*, *Trichophyton rubrum* and *Trichophyton tonsurans*.

In certain embodiments, the infectious disease antigen is a parasite antigen. In certain embodiments, the parasite antigen is derived from a parasite selected from the group consisting of *Anisakis* spp. *Babesia* spp., *Baylisascaris progonis*, *Cyptosporidium* spp., *Cyclospora cayetanensis*, *Diphyllobothrium* spp., *Dracunculus medinensis*, *Entamoeba histolytica*, *Giardia duodenalis*, *Giardia intestinalis*, *Giardia lamblia*, *Leishmania* sp., *Plasmodium falciparum*, *Schistosoma mansoni*, *Schistosoma haematobium*, *Schistosoma japonicum*, *Taenia* spp., *Toxoplasma gondii*, *Trichinella spiralis*, and *Typanosoma cruzi*.

In certain embodiments, the disease-associated antigen is a tumor-associated antigen. In certain embodiments, the tumor-associated antigen is selected from the group consisting of 5-α-reductase, α-fetoprotein ("AFP"), AM-1, APC, April, B melanoma antigen gene ("BAGE"), β-catenin, Bcl12, bcr-abl, Brachyury, CA-125, caspase-8 ("CASP-8", also known as "FLICE"), Cathepsins, CD19, CD20, CD21/complement receptor 2 ("CR2"), CD22/BL-CAM, CD23/$F_cεRII$, CD33, CD35/complement receptor 1 ("CR1"), CD44/PGP-1, CD45/leucocyte common antigen ("LCA"), CD46/membrane cofactor protein ("MCP"), CD52/CAMPATH-1, CD55/decay accelerating factor ("DAF"), CD59/protectin, CDC27, CDK4, carcinoembryonic antigen ("CEA"), c-myc, cyclooxygenase-2 ("cox-2"), deleted in colorectal cancer gene ("DCC"), DcR3, E6/E7, CGFR, EMBP, Dna78, farnesyl transferase, fibroblast growth factor-8a ("FGF8a"), fibroblast growth factor-8b ("FGF8b"), FLK-1/KDR, folic acid receptor, G250, G melanoma antigen gene family ("GAGE-family"), gastrin 17, gastrin-releasing hormone, ganglioside 2 ("GD2")/ganglioside 3 ("GD3")/ganglioside-monosialic acid-2 ("GM2"), gonadotropin releasing hormone ("GnRH"), UDP-GlcNAc:$R_1$Man ($\alpha$1-6)$R_2$ [GlcNAc to Man($\alpha$1-6)] $\beta$1,6-N-acetylglucosaminyltransferase V ("GnT V"), GP1, gp100/Pme117, gp-100-in4, gp15, gp75/tyrosine-related protein-1 ("gp75/TRP-1"), human chorionic gonadotropin ("hCG"), heparanase, Her2/neu, human mammary tumor virus ("HMTV"), 70 kiloDalton heat-shock protein ("HSP70"), human telomerase reverse transcriptase ("hTERT"), insulin-like growth factor receptor-1 ("IGFR-1"), interleukin-13 receptor ("IL-13R"), inducible nitric oxide synthase ("iNOS"), Ki67, KIAA0205, K-ras, H-ras, N-ras, KSA, LKLR-FUT, melanoma antigen-encoding gene 1 ("MAGE-1"), melanoma antigen-encoding gene 2 ("MAGE-2"), melanoma antigen-encoding gene 3 ("MAGE-3"), melanoma antigen-encoding gene 4 ("MAGE-4"), mammaglobin, MAP17, Melan-A/melanoma antigen recognized by T-cells-1 ("MART-1"), mesothelin, MIC A/B, MT-MMPs, mucin, testes-specific antigen NY-ESO-1, osteonectin, p15, P170/MDR1, p53, p97/melanotransferrin, PAI-1, platelet-derived growth factor ("PDGF"), $\mu$PA, PRAMS, probasin, progenipoietin, prostate-specific antigen ("PSA"), prostate-specific membrane antigen ("PSMA"), RAGE-1, Rb, RCAS1, SART-1, SSX-family, STAT3, STn, TAG-72, transforming growth factor-alpha ("TGF-$\alpha$"), transforming growth factor-beta ("TGF-$\beta$"), Thymosin-beta-15, tumor necrosis factor-alpha ("TNF-$\alpha$"), TP1, TRP-2, tyrosinase, vascular endothelial growth factor ("VEGF"), ZAG, p16INK4, and glutathione-S-transferase ("GST").

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and do not restrict the scope of the invention as claimed.

The accompanying drawings, which are incorporated in and constitute a part of this specification, illustrate various embodiments of the invention and together with the description, serve to explain the principles of the invention.

BRIEF DESCRIPTION OF THE SEQUENCES

Figure 1A:
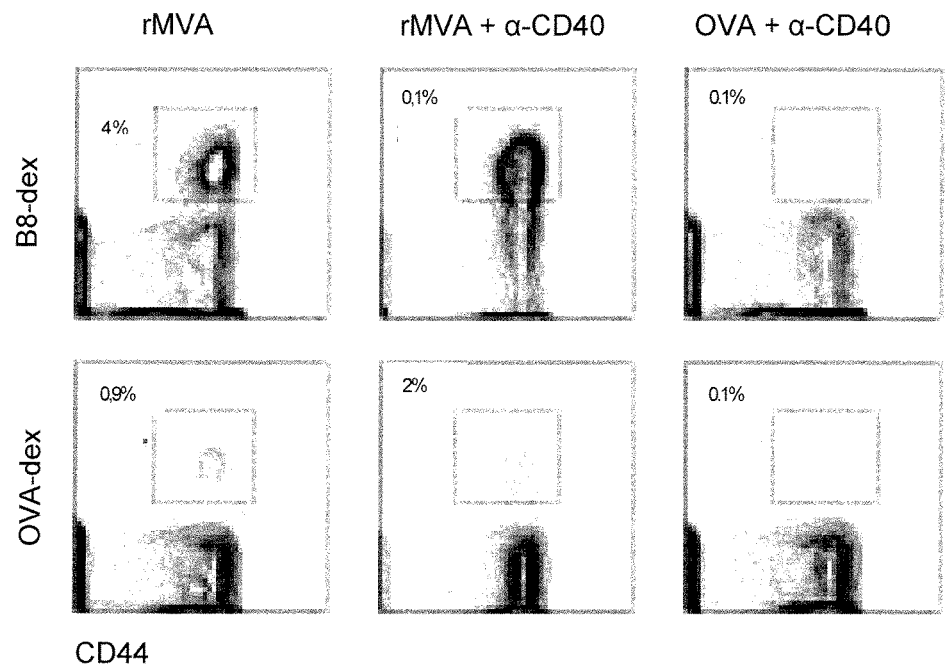
FIG. 1 shows that CD40 co-stimulation increases CTL responses to rMVA encoded antigens but not to a protein antigen. C57BL/6 mice were immunized with rMVA, rMVA+ anti-CD40 mAb or OVA protein+anti-CD40 monoclonal antibody ("mAb"). B8- and OVA-specific CD8 T-cells were visualized by MHC class I dextramer staining. (A) Density plots illustrate the frequency of B8- and OVA-specific CTL in the blood on day 7 (gated on CD8+$^+$ PBL). Numbers indicate the percentage of CD8$^+$ dextramer$^+$ T-cells among PBL. (B) Kinetic analysis of B8- and OVA-specific CTLs is shown. CTL responses to B8 and OVA were drastically enhanced by co-injection of rMVA and anti-CD40 mAb. Note that no detectable CTL response was generated after immunization with OVA protein and anti-CD40 antibody. (C) Similar to the above-described experiment, CBA/J (H-2k) mice were immunized with rMVA-GP encoding the glycoprotein of Ebola virus Zaire±anti-CD40 mAb. The GP-specific CD8+ T-cell response was measured seven days later by intracellular cytokine staining. Shown is the mean percentage±SEM of IFN-$\gamma^+$ GP-specific CD8+ T-cells in the spleen. Data represent four mice per group.

SEQ ID NO:1 is the amino acid sequence of murine CD40L.

SEQ ID NO:2 is the amino acid sequence of human CD40L.

SEQ ID NO:3 is the amino acid sequence of the MVA-derived peptide $B^8{}_{20\text{-}27}$.

SEQ ID NO:4 is the amino acid sequence of the ovalbumin-derived peptide $OVA_{257\text{-}264}$.

SEQ ID NO:5 is the amino acid sequence of the Ebola Virus-Zaire glycoprotein-derived peptide $GP_{577\text{-}584}$.

DESCRIPTION

Reference will now be made in detail to exemplary embodiments of the invention, examples of which are illustrated in the accompanying drawings. Wherever possible, the same reference numbers will be used throughout the drawings to refer to the same or like parts.

Definitions

Unless otherwise noted, technical terms herein are used according to conventional usage by one of ordinary skill in the art of molecular biology. For common terms in molecular biology, conventional usage may be found in standard textbooks such as, for example, *Genes V* by Benjamin Lewin, published by Oxford University Press, 1994 (ISBN 0-19-854287-9); Kendrew et al. (eds.); *The Encyclopedia of Molecular Biology*, published by Blackwell Science Ltd., 1994 (ISBN 0-632-02182-9); and *Molecular Biology and Biotechnology: a Comprehensive Desk Reference* edited by Robert A. Meyers, published by VCH Publishers, Inc., 1995 (ISBN 1-56081-569-8).

As used herein, the singular forms "a", "an", and "the" include plural references unless the context clearly indicates otherwise. Thus, for example, reference to "an epitope" includes reference to one or more epitopes and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize or be able to ascertain using no more than routine experimentation, many equivalents to the specific embodiments of the invention described herein. Such equivalents are encompassed by the present invention.

Throughout this specification and the claims which follow, unless the context requires otherwise, the word "comprise", and variations such as "comprises" and "comprising" mean "includes", and therefore include a stated integer or step or group of integers or steps and do exclude any other integer or step or group of integers or steps. When used herein the term "comprising" can be substituted with the term "containing", "including" or "having". Any of the aforementioned terms (comprising, containing, including, having), whenever used herein in the context of an aspect or embodiment of the present invention can be substituted with the term "consisting of".

When used herein, the term "consisting of" excludes any element, step, or ingredient not specified in the claim. When used herein, "consisting essentially of" excludes any materials or steps "which would affect the basic and novel characteristics" of the product or method defined in the rest of the claim. *Water Techs. Corp. v. Calco Ltd.*, 7 U.S.P.Q.2d 1097, 1102 (Fed. Cir. 1988).

As used herein, the conjunctive "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore to satisfy the requirement of the term "and/or" as used herein. Concurrent applicability of more than one of the options is also understood to fall within the meaning, and therefore satisfy the requirement of the term "and/or."

All publications, patent applications, patents, and other references mentioned herein are incorporated by reference in their entirety. In case of conflict, the present specification, including all definitions, will control.

Adjuvant: A vehicle used to enhance antigenicity. Adjuvants can include: (1) suspensions of minerals (alum, aluminum hydroxide, or phosphate) on which antigen is adsorbed; (2) water-in-oil emulsions in which an antigen solution is emulsified in mineral oil (Freund's incomplete adjuvant), sometimes with the inclusion of killed mycobacteria (Freund's complete adjuvant) to further enhance antigenicity by inhibiting degradation of antigen and/or causing an influx of macrophages; (3) immunstimulatory oligonucleotides such as, for example, those including a CpG motif can also be used as adjuvants (for example see U.S. Pat. Nos. 6,194,388; and 6,207,646); and (4) purified or recombinant proteins such as costimulatory molecules. Exemplary adjuvants include, but are not limited to, B7-1, ICAM-1, LFA-3, and GM-CSF.

Antigen; antigenic determinant; epitope: A compound, composition, or substance that can stimulate the production of antibodies or a CD4+ or CD8+ T-cell response in an animal, including compositions that are injected or absorbed into an animal. An antigen reacts with the immune system to produce an antigen-specific humoral or cellular immune response. The term "antigen" includes all related epitopes of a particular compound, composition or substance. The term "epitope" or "antigenic determinant" refers to a site on an antigen to which B- and/or T-cells respond, either alone or in conjunction with another protein such as, for example, a major histocompatibility complex ("MHC") protein or a T-cell receptor. Epitopes can be formed both from contiguous amino acids or noncontiguous amino acids juxtaposed by secondary and/or tertiary folding of a protein. Epitopes formed from contiguous amino acids are typically retained on exposure to denaturing solvents, while epitopes formed by tertiary folding are typically lost on treatment with denaturing solvents. An epitope typically includes at least 5, 6, 7, 8, 9, 10 or more amino acids—but generally less than 20 amino acids—in a unique spatial conformation. Methods of determining spatial conformation of epitopes include, for example, x-ray crystallography and 2-dimensional nuclear magnetic resonance. See, e.g., "Epitope Mapping Protocols" in *Methods in Molecular Biology*, Vol. 66, Glenn E. Morris, Ed (1996).

An antigen can be a tissue-specific (or tissue-associated) antigen or a disease-specific (or disease-associated) antigen. Those terms are not mutually exclusive, because a tissue-specific antigen can also be a disease-specific antigen. A tissue-specific antigen is expressed in a limited number of tissues. Tissue-specific antigens include, for example, prostate-specific antigen ("PSA"). A disease-specific antigen is expressed coincidentally with a disease process, where antigen expression correlates with or is predictive of development of a particular disease. Disease-specific antigens include, for example, HER-2, which is associated with certain types of breast cancer, or PSA, which is associated with prostate cancer. A disease-specific antigen can be an antigen recognized by T-cells or B-cells.

Cancer; Neoplasm; Tumor: A malignant growth arising from a particular body tissue that has undergone characteristic loss of structural differentiation, generally accompanied by increased capacity for cell division, invasion of surrounding tissue, and the capacity for metastasis. Tumors may be benign or malignant. For example, prostate cancer is a malignant neoplasm that arises in or from prostate tissue, ovarian cancer is a malignant neoplasm that arises in or from ovarian tissue, colon cancer is a malignant neoplasm that arises in or from colon tissue, and lung cancer is a malignant neoplasm that arises in or from lung tissue. Residual cancer is cancer that remains in a subject after treatment given to the subject to reduce or eradicate the cancer. Metastatic cancer is a cancer at one or more sites in the body other than the site of origin of the original (primary) cancer from which the metastatic cancer is derived.

cDNA (complementary DNA): A piece of DNA lacking internal non-coding segments (introns) and regulatory sequences that determine the timing and location of transcription initiation and termination. cDNA can be synthesized in the laboratory by reverse transcription of messenger RNA ("mRNA") extracted from cells.

Conservative variant: A "conservative" variant is a variant protein or polypeptide having one or more amino acid substitutions that do not substantially affect or decrease an activity or antigenicity of the protein or an antigenic epitope thereof. Generally conservative substitutions are those in which a particular amino acid is substituted with another amino acid having the same or similar chemical characteristics. For example, replacing a basic amino acid such as lysine with another basic amino acid such as arginine or glutamine is a conservative substitution. The term conservative variant also includes the use of a substituted amino acid in place of an unsubstituted parent amino acid, provided that antibodies raised to the substituted polypeptide also immunoreact with the unsubstituted polypeptide, and/or that the substituted polypeptide retains the function of the unstubstituted polypeptide. Non-conservative substitutions are those that replace a particular amino acid with one having different chemical characteristics, and typically reduce an activity or antigenicity of the protein or an antigenic epitope thereof.

Specific, non-limiting examples of conservative substitutions include the following examples:

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

CD4: Cluster of differentiation factor 4, a T-cell surface protein that mediates interaction with the MHC Class II molecule. Cells that express CD4, referred to as "CD4+" cells, are often helper T ("$T_H$") cells.

CD8: Cluster of differentiation factor 8, a T-cell surface protein that mediates interaction with the MHC Class I molecule. Cells that express CD8, referred to as "CD8+" cells, are often cytotoxic T ("CTL") cells.

CD40 Ligand; CD40L; CD154: CD40L is a protein that is primarily expressed on activated T-cells. It is a member of the tumor necrosis factor (TNF) protein superfamily. It binds to CD40 on antigen-presenting cells (APCs). That binding interaction induces a range of effects depending on the APC type. Generally, CD40L provides a costimulatory signal that activates APCd in conjunction with stimulation of the T-cell receptor (TCR) by major histocompatibility complex (MHC) molecules on the APC. CD40L also regulates B-cell function by binding CD40 on the surface of B-cells. The amino acid sequence of murine CD40L is set forth in SEQ ID NO:1. The amino acid sequence of human CD40L is set forth in SEQ ID NO:2.

The term CD40L encompasses the native amino acid sequence as set forth, for example, in SEQ ID NO:1 (Accession No. NM_011616.2) and SEQ ID NO:2 (NM_000074.2), protein fragments still able elicit an immune response in a host, as well as homologues or variants of proteins and protein fragments including, for example, glycosylated proteins or polypeptides. Thus, CD40L proteins and polypeptides are not limited to particular native amino acid sequences but encompass sequences identical to the native sequence as well as modifications to the native sequence, such as deletions, additions, insertions and substitutions. Preferably, such homologues or variants have at least about 80%, 81%, 82%, 83%, 84%, 85%, 86%, 87%, 88%, or 89%, at least about 90%, 91%, 92%, 93%, or 94%, at least about 95%, 96%, 97%, 98% or 99%, or about 100% amino acid sequence identity with the referenced protein or polypeptide. The term homologue or variant also encompasses truncated, deleted or otherwise modified nucleotide or protein sequences.

Techniques for determining sequence identity between amino acid sequences are known in the art. Two or more sequences can be compared by determining their "percent identity." The percent identity of two sequences is the number of exact matches between two aligned sequences divided by the length of the shorter sequence and multiplied by 100.

"Percent (%) amino acid sequence identity" with respect to proteins, polypeptides, antigenic protein fragments, antigens and epitopes described herein is defined as the percentage of amino acid residues in a candidate sequence that are identical with the amino acid residues in the reference sequence (i.e., the protein, polypeptide, antigenic protein fragment, antigen or epitope from which it is derived), after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the level of ordinary skill in the art, for example, using publically available computer software such as BLAST, ALIGN, or Megalign (DNASTAR) software. Those skilled in the art can determine appropriate parameters for measuring alignment, including any algorithms needed to achieve maximum alignment over the full length of the sequences being compared.

Chemotherapy; chemotherapeutic agents: Any therapeutically useful chemical agent for the treatment of diseases characterized by abnormal cell growth, including tumors, neoplasms and cancer. Commonly used classes of chemotherapeutics include alkylating agents, antimetabolites, natural products, or hormones and their antagonists. Alkylating agents include nitrogen mustards, alkyl sulfonates, and nitrosoureas. Antimetabolites include folic acid analogs, pyrimidine analogs, and purine analogs. Natural products include vinca alkaloids, epipodophyllotoxins, antibiotics, and enzymes. Miscellaneous agents include platinum coordination complexes, substituted ureas, methyl hydrazine derivatives, and adrenocortical suppressants. Hormones and hormone antagonists include adrenocorticosteroids, progestins, estrogens, antiestrogens, and androgens.

Costimulatory molecule: T-cell activation typically requires binding of the T-cell receptor ("TCR") with a peptide-MHC complex as well as a second signal delivered via the interaction of a costimulatory molecule with its ligand. Costimulatory molecules are molecules that, when bound to their ligand, deliver the second signal required for T-cell activation. The most well-known costimulatory molecule on the T-cell is CD28, which binds to either B7-1 or B7-2. Other costimulatory molecules that can also provide the second signal necessary for activation of T-cells include intracellular adhesion molecule-1 ("ICAM-1"), intracellular adhesion molecule-2 ("ICAM-2"), leukocyte function associated antigen-1 ("LFA-1"), leukocyte function associated antigen-2 ("LFA-2"), and leukocyte function associated antigen-3 ("LFA-3").

Degenerate variant: A polynucleotide encoding a protein or fragment thereof that includes a sequence that contains codons that differ from the native or wild-type gene sequence but still specify the same amino acid. The genetic code includes 20 natural amino acids, most of which are specified by more than one codon. All degenerate nucleotide sequences are encompassed in this disclosure provided the amino acid sequence of the Brachyury protein encoded by the degenerate polynucleotide remains unchanged.

Dendritic cell (DC): Dendritic cells are the primary antigen presenting cells ("APCs") involved in primary immune responses. Dendritic cells include plasmacytoid dendritic cells and myeloid dendritic cells. Their major function is to obtain antigen in tissues, migrate to lymphoid organs and present the antigen in order to activate T-cells. Immature dendritic cells originate in the bone marrow and reside in the periphery as immature cells.

Disease-associated antigen: A disease-associated antigen is expressed coincidentally with a particular disease process, where antigen expression correlates with or predicts development of that disease. Disease-associated antigens include, for example, HER-2, which is associated with certain types of breast cancer, or prostate-specific antigen ("PSA"), which is associated with prostate cancer. A disease-associated antigen can be an antigen recognized by T-cells or B-cells. Some disease-associated antigens may also be tissue-specific. A tissue-specific antigen is expressed in a limited number of tissues. Tissue-specific antigens include, for example, prostate-specific antigen PSA.

Disease-associated antigens can be, for example, tumor antigens, viral antigens, bacterial antigens, fungal antigens, or parasite antigens.

The term "tumor antigen" refers to antigens present expressed exclusively on, associated with, or over-expressed in tumor tissue. Exemplary tumor antigens include, but are not limited to, 5-α-reductase, α-fetoprotein ("AFP"), AM-1, APC, April, B melanoma antigen gene ("BAGE"), β-catenin, Bcl12, bcr-abl, Brachyury, CA-125, caspase-8 ("CASP-8", also known as "FLICE"), Cathepsins, CD19, CD20, CD21/complement receptor 2 ("CR2"), CD22/BL-CAM, CD23/F$_c$εRII, CD33, CD35/complement receptor 1 ("CR1"), CD44/PGP-1, CD45/leucocyte common antigen ("LCA"), CD46/membrane cofactor protein ("MCP"), CD52/CAMPATH-1, CD55/decay accelerating factor ("DAF"), CD59/protectin, CDC27, CDK4, carcinoembryonic antigen ("CEA"), c-myc, cyclooxygenase-2 ("cox-2"), deleted in colorectal cancer gene ("DCC"), DcR3, E6/E7, CGFR, EMBP, Dna78, farnesyl transferase, fibroblast growth factor-8a ("FGF8a"), fibroblast growth factor-8b ("FGF8b"), FLK-1/KDR, folic acid receptor, G250, G melanoma antigen gene family ("GAGE-family"), gastrin 17, gastrin-releasing hormone, ganglioside 2 ("GD2")/ganglioside 3 ("GD3")/ganglioside-monosialic acid-2 ("GM2"), gonadotropin releasing hormone ("GnRH"), UDP-GlcNAc: $R_1$Man(α1-6)$R_2$ [GlcNAc to Man(α1-6)] β1,6-N-acetylglucosaminyltransferase V ("GnT V"), GP1, gp100/Pme117, gp-100-in4, gp15, gp75/tyrosine-related protein-1 ("gp75/TRP-1"), human chorionic gonadotropin ("hCG"), heparanase, Her2/neu, human mammary tumor virus ("HMTV"), 70 kiloDalton heat-shock protein ("HSP70"), human telomerase reverse transcriptase ("hTERT"), insulin-like growth factor receptor-1 ("IGFR-1"), interleukin-13 receptor ("IL-13R"), inducible nitric oxide synthase ("iNOS"), Ki67, KIAA0205, K-ras, H-ras, N-ras, KSA, LKLR-FUT, melanoma antigen-encoding family ("MAGE-family", including at least MAGE-1, MAGE-2, MAGE-3, and MAGE-4), mammaglobin, MAP17, Melan-A/melanoma antigen recognized by T-cells-1 ("MART-1"), mesothelin, MIC A/B, MT-MMPs, mucin, testes-specific antigen NY-ESO-1, osteonectin, p15, P170/MDR1, p53, p97/melanotransferrin, PAI-1, platelet-derived growth factor ("PDGF"), μPA, PRAME, probasin, progenipoietin, prostate-specific antigen ("PSA"), prostate-specific membrane antigen ("PSMA"), RAGE-1, Rb, RCAS1, SART-1, SSX-family, STAT3, STn, TAG-72, transforming growth factor-alpha ("TGF-α"), transforming growth factor-beta ("TGF-β"), Thymosin-beta-15, tumor necrosis factor-alpha ("TNF-α"), TP1, TRP-2, tyrosinase, vascular endothelial growth factor ("VEGF"), ZAG, p16INK4, and glutathione-S-transferase ("GST").

The term "viral antigen" refers to antigens derived from any disease-associated pathogenic virus. Exemplary disease-associated viral antigens include, but are not limited to, antigens derived from adenovirus, Coxsackievirus, Crimean-Congo hemorrhagic fever virus, cytomegalovirus ("CMV"), dengue virus, Ebola virus, Epstein-Barr virus ("EBV"), Guanarito virus, herpes simplex virus-type 1 ("HSV-1"), herpes simplex virus-type 2 ("HSV-2"), human herpesvirus-type 8 ("HHV-8"), hepatitis A virus ("HAV"), hepatitis B virus ("HBV"), hepatitis C virus ("HCV"), hepatitis D virus ("HDV"), hepatitis E virus ("HEV"), human immunodeficiency virus ("HIV"), influenza virus, Junin virus, Lassa virus, Machupo virus, Marburg virus, measles virus, human metapneumovirus, mumps virus, Norwalk virus, human papillomavirus ("HPV"), parainfluenza virus, parvovirus, poliovirus, rabies virus, respiratory syncytial virus ("RSV"), rhinovirus, rotavirus, rubella virus, Sabia virus, severe acute respiratory syndrome virus ("SARS"), varicella zoster virus, variola virus, West Nile virus, and yellow fever virus.

The term "bacterial antigen" refers to antigens derived from any disease-associated pathogenic virus. Exemplary bacterial antigens include, but are not limited to, antigens derived from *Bacillus anthracis, Bordetella pertussis, Borrelia burgdorferi, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium peringens, Clostridium tetani, Corynebacterium diptheriae, Enterococcus faecalis, Enterococcus faecium, Escherichia coli*, enterotoxigenic *Escherichia coli*, enteropathogenic *Escherichia coli, Escherichia coli*) 157: H7, *Francisella tularensis, Haemophilus influenza, Helicobacter pylori, Legionella pneumophila, Leptospira interrogans, Listeria monocytogenes, Mycobacterium leprae, Mycobacterium tuberculosis, Mycoplasma pneumoniae, Neisseria gonorrhoeae, Neisseria meningitides, Pseudomonas aeruginosa, Rickettsia rickettsia, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholerae*, and *Yersinia pestis*.

The term "fungal antigen" refers to antigens derived from any disease-associated pathogenic fungus. Exemplary fungal antigens include, but are not limited to, antigens derived from *Aspergillus clavatus*, *Aspergillus flavus*, *Aspergillus fumigatus*, *Aspergillus nidulans*, *Aspergillus niger*, *Aspergillus terreus*, *Blastomyces dermatitidis*, *Candida albicans*, *Candida dubliniensis*, *Candida glabrata*, *Candida parapsilosis*, *Candida rugosa*, *Candida tropicalis*, *Cryptococcus albidus*, *Cryptococcus Cryptococcus laurentii*, *Cryptococcus neoformans*, *Histoplasma capsulatum*, *Microsporum canis*, *Pneumocystis carinii*, *Pneumocystis jirovecii*, *Sporothrix schenckii*, *Stachbotrys chartarum*, *Tinea barbae*, *Tinea captitis*, *Tinea corporis*, *Tinea cruris*, *Tinea faciei*, *Tinea incognito*, *Tinea nigra*, *Tinea versicolor*, *Trichophyton rubrum* and *Trichophyton tonsurans*.

The term "parasite antigen" refers to antigens derived from any disease-associated pathogenic parasite. Exemplary parasite antigens include, but are not limited to, antigens derived from *Anisakis* spp. *Babesia* spp., *Baylisascaris procyonis*, *Cyptosporidium* spp., *Cyclospora cayetanensis*, *Diphyllobothrium* spp., *Dracunculus medinensis*, *Entamoeba histolytica*, *Giardia duodenalis*, *Giardia intestinalis*, *Giardia lamblia*, *Leishmania* sp., *Plasmodium falciparum*, *Schistosoma mansoni*, *Schistosoma haematobium*, *Schistosoma japonicum*, *Taenia* spp., *Toxoplasma gondii*, *Trichinella spiralis*, and *Trypanosoma cruzi*.

Expression Control Sequences: Nucleic acid sequences that regulate the expression of a heterologous nucleic acid sequence to which they are operatively linked. Expression control sequences are operatively linked to a nucleic acid sequence when the expression control sequences control and regulate the transcription and/or translation of the nucleic acid sequence. Thus, the term "expression control sequences" encompasses promoters, enhancers, transcription terminators, start codons, splicing signals for introns, and stop codons. The term "control sequences" includes, at a minimum, components the presence of which can influence transcription and/or translation of the heterologous nucleic acid sequence and can also include additional components whose presence is advantageous such as, for example, leader sequences and fusion partner sequences.

The term "expression control sequences" encompasses promoter sequences. A promoter is a minimal sequence sufficient to direct transcription of a homologous or heterologous gene. Also included are those promoter elements sufficient to render promoter-dependent gene expression cell-type specific, tissue-specific, or inducible by external signals or agents; such elements may be located in the 5' or 3' regions of the gene. The term "promoter" encompasses both constitutive and inducible promoters. See, e.g., Bitter et al., *Methods in Enzymology* 153:516-544 (1987). Exemplary promoter sequences include, but are not limited to, the retrovirus long terminal repeat ("LTR"), the adenovirus major late promoter, the vaccinia virus 7.5K promoter ("Pr7.5"), the vaccinia virus synthetic early/late promoter ("sE/L"), the PrSynIIm promoter, the PrLE1 promoter, the PrH5m promoter, the PrS promoter, a hybrid early/late promoter, or a cowpox virus ATI promoter.

Heterologous: Originating from separate genetic sources or species. A polypeptide that is heterologous to human Brachyury originated from a nucleic acid that does not encode human Brachyury such as, for example, mouse Brachyury, β-galactosidase, maltose binding protein, or human serum albumin.

Host cells: Cells in which a vector can be propagated and its DNA expressed. The cells may be prokaryotic (e.g., bacterial) or eukaryotic (e.g., mammalian or human). The term also encompasses progeny of the original host cell, even though all progeny may not be identical to the parental cell since there may be mutations that occur during replication.

Immune response: An adaptive response of an immune system cell, such as a B-cell, T-cell, or monocyte, to a stimulus. An adaptive response is a response to a particular antigen, and is thus described as "antigen-specific". An adaptive immune response can include the production of antibodies to a particular antigen by a B-cell, T-cell help by a CD4+ helper T-cell expanding a population of antigen-specific CD8+ T-cells ("CTLs"), cytotoxic activity of CD8+ T-cells directed against cells expressing a particular antigen, or yet another type of antigen-specific immune response.

Immunogenic composition: As used herein, the term "immunogenic composition" refers to a composition comprising a nucleic acid encoding the CD40L protein and a nucleic acid encoding a disease-associated antigen, both under the control of an expression control sequence or promoter, such as a poxvirus vector, that induces a measurable disease-associated antigen-specific, adaptive immune response. The nucleic acid or poxvirus vector may optionally include additional nucleic acids encoding, for example, one or more costimulatory molecules as described elsewhere herein. That immune response may be, for example, a CD8+ T-cell or CTL response directed against cells expressing the disease-associated antigen, or a B-cell response producing disease-associated antigen-specific antibodies. Such compositions may include the isolated nucleic acid or vector, optionally formulated with one or more pharmaceutically acceptable carriers.

Lymphocytes: A type of white blood cell that is involved in the immune defenses of the body. There are two main types of lymphocytes: B-cells and T-cells.

Major Histocompatibility Complex (MHC): A generic designation meant to encompass the histocompatability antigen systems described in different species, including the human leukocyte antigens ("HLA").

Mammal: This term includes both human and non-human mammals. Similarly, the term "subject" includes both human and veterinary subjects.

Open reading frame (ORF): A series of nucleotide codons specifying a series of amino acids without any internal termination codons that capable of being translated to produce a polypeptide.

Operably linked: A first nucleic acid sequence is operably linked to a second nucleic acid sequence when the first nucleic acid sequence is placed in a functional relationship with the second nucleic acid sequence. For example, a promoter is operably linked to a coding sequence if the promoter is placed in a position where it can direct transcription of the coding sequence. Generally, operably linked DNA sequences are contiguous and, where necessary to join two protein-coding regions, in the same reading frame.

Pharmaceutically acceptable carriers: *Remington's Pharmaceutical Sciences*, by E. W. Martin, Mack Publishing Co., Easton, Pa., 15th Edition (1975), describes compositions and formulations using conventional pharmaceutically acceptable carriers suitable for administration of the vectors and compositions disclosed herein. Generally the nature of the carrier used depends on the particular mode of administration being employed. For example, parenteral formulations usually comprise injectable fluids that include pharmaceutically and physiologically acceptable fluids such as water, physiological saline, balanced salt solutions, aqueous dextrose, glycerol or the like, as a vehicle. For solid compositions (such as powders, pills, tablets, or capsules), conventional non-toxic solid carriers include, for example, pharmaceutical grades of mannitol, lactose, starch, or magnesium stearate. Pharmaceutical compositions can also contain minor amounts of non-toxic auxiliary substances such as wetting or emulsifying agents, preservatives, pH-buffering agents and the like such as, for example, sodium acetate or sorbitan monolaurate.

Polynucleotide; nucleic acid: The term polynucleotide refers to a nucleic acid polymer at least 300 bases long composed of ribonucleotides (i.e., RNA) or deoxyribonucleotides (i.e., DNA or cDNA) and capable of encoding a polypeptide or protein. The term includes single- and double-stranded forms of DNA.

Polypeptide or Protein: The term polypeptide or protein refers to an polymer at least 100 amino acids long, generally greater than 50 amino acids in length.

Poxvirus: The term poxvirus refers to any of the genera of poxviruses capable of infecting humans (e.g., orthopox viruses, avipox viruses, parapox viruses, yatapox viruses, and molluscipox viruses) whether productively or not, but preferably the orthopox and/or avipox viruses. Orthopox viruses include smallpox virus (also known as variola virus), vaccinia virus, cowpox virus, and monkeypox virus. Avipox viruses include canarypox virus and fowlpox virus. The term "vaccinia virus" refers to both the wild-type vaccinia virus and any of the various attenuated strains or isolates subsequently isolated including, for example, vaccinia virus-Western Reserve, vaccinia virus-Copenhagen, Dryvax (also known as vaccinia virus-Wyeth), ACAM2000, modified vaccinia virus Ankara ("MVA"), and modified vaccinia virus Ankara-Bavarian Nordic ("MVA-BN").

Prime-boost vaccination: The term "prime-boost vaccination" refers to a vaccination strategy using a first, priming injection of a vaccine targeting a specific antigen followed at intervals by one or more boosting injections of the same vaccine. Prime-boost vaccination may be homologous or heterologous. A homologous prime-boost vaccination uses a vaccine comprising the same immunogen and vector for both the priming injection and the one or more boosting injections. A heterologous prime-boost vaccination uses a vaccine comprising the same immunogen for both the priming injection and the one or more boosting injections but different vectors for the priming injection and the one or more boosting injections. For example, a homologous prime-boost vaccination may use an MVA vector comprising nucleic acids expressing Brachyury and TRICOM for both the priming injection and the one or more boosting injections. In contrast, a heterologous prime-boost vaccination may use an MVA vector comprising nucleic acids expressing Brachyury and TRICOM for the priming injection and a fowlpox vector comprising nucleic acids expressing Brachyury and TRICOM for the one or more boosting injections. Heterologous prime-boost vaccination also encompasses various combinations such as, for example, use of a plasmid encoding an immunogen in the priming injection and use of a poxvirus vector encoding the same immunogen in the one or more boosting injections, or use of a recombinant protein immunogen in the priming injection and use of a plasmid or poxvirus vector encoding the same protein immunogen in the one or more boosting injections.

Recombinant; recombinant nucleic acid; recombinant vector; recombinant poxvirus: The term "recombinant" when applied to a nucleic acid, vector, poxvirus and the like refers to a nucleic acid, vector, or poxvirus made by an artificial combination of two or more otherwise heterologous segments of nucleic acid sequence, or to a nucleic acid, vector or poxvirus comprising such an artificial combination of two or more otherwise heterologous segments of nucleic acid sequence. The artificial combination is most commonly accomplished the artificial manipulation of isolated segments of nucleic acids, using well-established genetic engineering techniques.

Sequence identity: The term "sequence identity" refers to the degree of similarity between the nucleic acid or amino acid sequences. Sequence identity is frequently measured in terms of percent identity (often described as sequence "similarity" or "homology"). The higher the percent sequence identity, the more similar the two sequences are. Homologs or variants of a Brachyury protein will have a relatively high degree of sequence identity when aligned using standard methods.

Methods of aligning sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Higgins and Sharp, *Gene* 73:237, 1988; Higgins and Sharp, *CABIOS* 5:151, 1989; Corpet et al., *Nucl. Acids Res.* 16:10881, 1988; and Pearson and Lipman, *Proc. Nat'l Acad. Sci. USA* 85:2444, 1988. In addition, Altschul et al., *Nature Genet.* 6:119, 1994, presents a detailed consideration of sequence alignment methods and homology calculations. The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.; see also http://blast.ncbi.nlm.nih.gov/Blast.cgi), for use in connection with the sequence analysis programs blastp, blastn, blastx, tblastn and tblastx.

Homologs and variants of a human Brachyury protein typically have at least 90%, 91%, 92%, 93%, 94%, 95%, 96%, 97%, 98% or 99% amino acid sequence identity over a full-length alignment with the amino acid sequence of wild-type human Brachyury prepared with NCBI Blast v2.0, using blastp set to the default parameters. For comparisons of amino acid sequences of greater than about 30 amino acids, the Blast 2 sequences function is employed using the default BLOSUM62 matrix set to the default parameters (gap existence cost of 11, and a per residue gap cost of 1).

Subject: Living multi-cellular vertebrate organisms, including, for example, humans, non-human mammals and birds. The term "subject" may be used interchangeably with the term "animal" herein.

T-Cell: A lymphocyte or white blood cell essential to the adaptive immune response. T-cells include, but are not limited to, $CD4^+$ T-cells and $CD8^+$ T-cells. A $CD4^+$ T-cell is an immune cell that carries a marker on its surface known as "cluster of differentiation 4" ("CD4"). These cells, also known as helper T-cells, help orchestrate the immune response, including both antibody and CTL responses. $CD8^+$ T-cells carry the "cluster of differentiation 8" ("CD8") marker. CD8+ T-cells include both CTLs, memory CTLs, and suppressor T-cells.

Therapeutically active polypeptide: An agent composed of amino acids, such as a Brachyury protein, that induces an adaptive immune response, as measured by clinical response (e.g., an increase in CD4+ T-cells, CD8+ T-cells, or B-cells, an increase in Brachyury-specific cytolytic activity, a measurable reduction in tumor size, or a reduction in number of metastases). Therapeutically active molecules can also be made from nucleic acids such as, for example, a poxvirus vector comprising a nucleic acid encoding human Brachyury operably linked to an expression control sequence.

Therapeutically effective amount: A "therapeutically effective amount" is a quantity of a composition or a cell sufficient to achieve a desired therapeutic or clinical effect in a subject being treated. For example, a therapeutically effective amount of a poxviral vector comprising a nucleic acid encoding human Brachyury protein operably linked to an expression control sequence would be an amount sufficient to elicit a Brachyury-specific immune response, to reduce tumor size or burden, to reduce the number of tumor metastases, to delay progression of a cancer, or to increase overall survival of a patient or population of patients having cancer. A therapeutically effective amount of the poxvirus vectors and compositions comprising the poxvirus vectors described herein is an amount sufficient to raise an immune response to Brachyury-expressing cells. The immune response must be of sufficient magnitude to slow the proliferation of Brachyury-expressing cells, to inhibit their growth, to reduce a sign or a symptom of the tumor, to provide subjective relief of one or more symptoms associated with the tumor or to provide objectively identifiable improvement in one or more symptoms noted by the attending clinician such as, for example, a reduction in tumor size, a decrease in the number of metastatic lesions, a delay in disease progression, or an increase in overall survival, and the like.

Transduced or Transformed: The term "transduced" or "transformed" refers to a cell into which a recombinant nucleic acid has been introduced by standard molecular biological methods. As used herein, the term transduction encompasses all techniques by which a nucleic acid molecule might be introduced into such a cell, including infection with viral vectors, transformation with plasmid vectors, and introduction of naked DNA by electroporation, lipofection, or particle gun acceleration.

Treating cancer: The term "treating cancer" refers to a therapeutic intervention intended to reduce or eliminate a sign or symptom of the cancer or to delay progression of the disease and increase overall survival of a subject having cancer. Cancer may be treated by standard chemotherapy, radiation, or active immunotherapy such as, for example, administration of a recombinant vaccinia virus comprising a nucleic acid encoding a Brachyury protein. Reducing or eliminating a sign or symptom of the cancer encompasses a wide variety of effects including, for example reducing signs or symptoms of a tumor, reducing tumor volume, reducing the number of metastases, increasing response duration, increasing time to progression, increasing disease-free survival, increasing progression-free survival, or increasing the overall survival of patients having the disease.

TRICOM: A Triad of COstimlatory Molecules consisting of B7-1 (also known as CD80), intracellular adhesion molecule-1 (ICAM-1, also known as CD54) and lymphocyte function-associated antigen-3 (LFA-3, also known as CD58), commonly included in recombinant viral vectors (e.g., poxviral vectors) expressing a specific antigen in order to increase the antigen-specific immune response. The individual components of TRICOM can be under the control of the same or different promoters, and can be provided on the same vector with the specific antigen or on a separate vector. Exemplary vectors are disclosed, for example, in Hodge et al., "A Triad of Costimulatory Molecules Synergize to Amplify T-Cell Activation," *Cancer Res.* 59:5800-5807 (1999) and U.S. Pat. No. 7,211,432 B2, both of which are incorporated herein by reference.

Vector: A nucleic acid molecule introduced into a host cell, thereby producing a transduced or transformed host cell. Vectors generally include nucleic acid sequences enabling them to replicate in a host cell, such as an origin of replication, as well as one or more selectable marker genes, expression control sequences, restriction endonuclease recognition sequences, primer sequences and a variety of other genetic elements known in the art. Commonly used vector types include plasmids for expression in bacteria (e.g., *E. coli*) or yeast (e.g., *S. cerevisiae*), shuttle vectors for constructing recombinant poxviruses, cosmids, bacterial artificial chromosomes, yeast artificial chromosomes, and viral vectors. Viral vectors include poxvirus vectors, retrovirus vectors, adenovirus vectors, herpes virus vectors, baculovirus vectors, Sindbis virus vecturs, and poliovirus vectors, among others. Poxvirus vectors include, but are not limited to orthopox viruses, avipox viruses, parapox viruses, yatapox viruses, and molluscipox viruses, but preferably the orthopox and/or avipox viruses. Orthopox viruses include smallpox virus (also known as variola virus), vaccinia virus, cowpox virus, and monkeypox virus. Avipox viruses include canarypox virus and fowlpox virus. The term "vaccinia virus" refers to both the wild-type vaccinia virus and any of the various attenuated strains or isolates subsequently isolated including, for example, vaccinia virus-Western Reserve, vaccinia virus-Copenhagen, Dryvax (also known as vaccinia virus-Wyeth), ACAM2000, modified vaccinia virus Ankara ("MVA"), and modified vaccinia virus Ankara-Bavarian Nordic ("MVA-BN").

Modified Vaccinia Virus Ankara (MVA)

MVA has been generated by more than 570 serial passages on chicken embryo fibroblasts of the dermal vaccinia strain Ankara [Chorioallantois vaccinia virus Ankara virus, CVA; for review see Mayr et al. (1975), Infection 3, 6-14] that was maintained in the Vaccination Institute, Ankara, Turkey for many years and used as the basis for vaccination of humans. However, due to the often severe post-vaccinal complications associated with vaccinia viruses, there were several attempts to generate a more attenuated, safer smallpox vaccine.

During the period of 1960 to 1974, Prof. Anton Mayr succeeded in attenuating CVA by over 570 continuous passages in CEF cells [Mayr et al. (1975)]. It was shown in a variety of animal models that the resulting MVA was avirulent [Mayr, A. & Danner, K. (1978), Dev. Biol. Stand. 41: 225-234]. As part of the early development of MVA as a pre-smallpox vaccine, there were clinical trials using MVA-517 in combination with Lister Elstree [Stickl (1974), Prey. Med. 3: 97-101; Stickl and Hochstein-Mintzel (1971), Munich Med. Wochenschr. 113: 1149-1153] in subjects at risk for adverse reactions from vaccinia. In 1976, MVA derived from MVA-571 seed stock (corresponding to the $571^{st}$ passage) was registered in Germany as the primer vaccine in a two-stage parenteral smallpox vaccination program. Subsequently, MVA-572 was used in approximately 120,000 Caucasian individuals, the majority children between 1 and 3 years of age, with no reported severe side effects, even though many of the subjects were among the population with high risk of complications associated with vaccinia (Mayr et al. (1978), *Zentralbl. Bacteria*. (B) 167: 375-390). MVA-572 was deposited at the European Collection of Animal Cell Cultures as ECACC V94012707.

As a result of the passaging used to attenuate MVA, there are a number of different strains or isolates, depending on the passage number in CEF cells. For example, MVA-572 was used in Germany during the smallpox eradication program, and MVA-575 was extensively used as a veterinary vaccine. MVA-575 was deposited on Dec. 7, 2000, at the European Collection of Animal Cell Cultures (ECACC) with the deposition number V00120707. The attenuated CVA-virus MVA (Modified Vaccinia Virus Ankara) was obtained by serial propagation (more than 570 passages) of the CVA on primary chicken embryo fibroblasts.

Even though Mayr and colleagues demonstrated during the 1970s that MVA is highly attenuated and avirulent in humans and mammals, certain investigators have reported that MVA is not fully attenuated in mammalian and human cell lines since residual replication might occur in these cells [Blanchard et al. (1998), J Gen Virol 79:1159-1167; Carroll & Moss (1997), Virology 238:198-211; U.S. Pat. No. 5,185,146; Ambrosini et al. (1999), J Neurosci Res 55: 569]. It is assumed that the results reported in these publications have been obtained with various known strains of MVA, since the viruses used essentially differ in their properties, particularly in their growth behaviour in various cell lines. Such residual replication is undesirable for various reasons, including safety concerns in connection with use in humans.

Strains of MVA having enhanced safety profiles for the development of safer products, such as vaccines or pharmaceuticals, have been developed by Bavarian Nordic: MVA was further passaged by Bavarian Nordic and is designated MVA-BN. MVA as well as MVA-BN lacks approximately 15% (31 kb from six regions) of the genome compared with ancestral CVA virus. The deletions affect a number of virulence and host range genes, as well as the gene for Type A inclusion bodies. A sample of MVA-BN corresponding to passage 583 was deposited on Aug. 30, 2000 at the European Collection of Cell Cultures (ECACC) under number V00083008.

MVA-BN can attach to and enter human cells where virally-encoded genes are expressed very efficiently. However, assembly and release of progeny virus does not occur. MVA-BN is strongly adapted to primary chicken embryo fibroblast (CEF) cells and does not replicate in human cells. In human cells, viral genes are expressed, and no infectious virus is produced. MVA-BN is classified as Biosafety Level 1 organism according to the Centers for Disease Control and Prevention in the United States. Preparations of MVA-BN and derivatives have been administered to many types of animals, and to more than 2000 human subjects, including immune-deficient individuals. All vaccinations have proven to be generally safe and well tolerated. Despite its high attenuation and reduced virulence, in preclinical studies MVA-BN has been shown to elicit both humoral and cellular immune responses to vaccinia and to heterologous gene products encoded by genes cloned into the MVA genome [E. Harrer et al. (2005), *Antivir. Ther.* 10(2):285-300; A. Cosma et al. (2003), *Vaccine* 22(1):21-9; M. Di Nicola et al. (2003), *Hum. Gene Ther.* 14(14):1347-1360; M. Di Nicola et al. (2004), *Clin. Cancer Res.,* 10(16):5381-5390].

"Derivatives" or "variants" of MVA refer to viruses exhibiting essentially the same replication characteristics as MVA as described herein, but exhibiting differences in one or more parts of their genomes. MVA-BN as well as a derivative or variant of MVA-BN fails to reproductively replicate in vivo in humans and mice, even in severely immune suppressed mice. More specifically, MVA-BN or a derivative or variant of MVA-BN has preferably also the capability of reproductive replication in chicken embryo fibroblasts (CEF), but no capability of reproductive replication in the human keratinocyte cell line HaCat [Boukamp et al (1988), J Cell Biol 106: 761-771], the human bone osteosarcoma cell line 143B (ECACC No. 91112502), the human embryo kidney cell line 293 (ECACC No. 85120602), and the human cervix adenocarcinoma cell line HeLa (ATCC No. CCL-2). Additionally, a derivative or variant of MVA-BN has a virus amplification ratio at least two-fold less, more preferably three-fold less than MVA-575 in Hela cells and HaCaT cell lines. Tests and assay for these properties of MVA variants are described in WO 02/42480 (US 2003/0206926) and WO 03/048184 (US 2006/0159699), both incorporated herein by reference.

The amplification or replication of a virus is normally expressed as the ratio of virus produced from an infected cell (output) to the amount originally used to infect the cell in the first place (input) referred to as the "amplification ratio". An amplification ratio of "1" defines an amplification status where the amount of virus produced from the infected cells is the same as the amount initially used to infect the cells, meaning that the infected cells are permissive for virus infection and reproduction. In contrast, an amplification ratio of less than 1, i.e., a decrease in output compared to the input level, indicates a lack of reproductive replication and therefore attenuation of the virus.

The advantages of MVA-based vaccine include their safety profile as well as availability for large scale vaccine production. Preclinical tests have revealed that MVA-BN demonstrates superior attenuation and efficacy compared to other MVA strains (WO02/42480). An additional property of MVA-BN strains is the ability to induce substantially the same level of immunity in vaccinia virus prime/vaccinia virus boost regimes when compared to DNA-prime/vaccinia virus boost regimes.

The recombinant MVA-BN viruses, the most preferred embodiment herein, are considered to be safe because of their distinct replication deficiency in mammalian cells and their well-established avirulence. Furthermore, in addition to its efficacy, the feasibility of industrial scale manufacturing can be beneficial. Additionally, MVA-based vaccines can deliver multiple heterologous antigens and allow for simultaneous induction of humoral and cellular immunity.

In another aspect, an MVA viral strain suitable for generating the recombinant virus may be strain MVA-572, MVA-575 or any similarly attenuated MVA strain. Also suitable may be a mutant MVA, such as the deleted chorioallantois vaccinia virus Ankara (dCVA). A dCVA comprises del I, del II, del III, del IV, del V, and del VI deletion sites of the MVA genome. The sites are particularly useful for the insertion of multiple heterologous sequences. The dCVA can reproductively replicate (with an amplification ratio of greater than 10) in a human cell line (such as human 293, 143B, and MRC-5 cell lines), which then enable the optimization by further mutation useful for a virus-based vaccination strategy (see, e.g., WO 2011/092029).

Immunogenic Compositions and Disease-Associated Antigens

In one aspect, provided herein are immunogenic compositions comprising recombinant poxviruses such as, for example, modified vaccinia virus Ankara (MVA) comprising a nucleic acid sequence encoding a CD40 ligand (CD40L) and a nucleic acid sequence encoding a heterologous disease-associated antigen, wherein the immunogenic composition induces increased T-cell immune responses specific for the heterologous disease-associated antigen when administered to a human host.

In certain embodiments, the nucleic acid sequence encodes a CD40L having an amino acid sequence having at least 95%, 96%, 97%, 98%, 99%, or 100% amino acid sequence identity to SEQ ID NO:1. In certain embodiments, the nucleic acid sequence encodes a CD40L having an amino acid sequence having at least 95% amino acid sequence identity to SEQ ID NO:1. In certain embodiments, the nucleic acid sequence encodes a CD40L having an amino acid sequence having at least 96% amino acid sequence identity to SEQ ID NO:1. In certain embodiments, the nucleic acid sequence encodes a CD40L having an amino acid sequence having at least 97% amino acid sequence identity to SEQ ID NO:1. In certain embodiments, the nucleic acid sequence encodes a CD40L having an amino acid sequence having at least 98% amino acid sequence identity to SEQ ID NO:1. In certain embodiments, the nucleic acid sequence encodes a CD40L having an amino acid sequence having at least 99% amino acid sequence identity to SEQ ID NO:1. In certain embodiments, the nucleic acid sequence encodes a CD40L having the amino acid sequence of SEQ ID NO:1.

In certain embodiments, the nucleic acid sequence encodes a CD40L having an amino acid sequence having at least 95%, 96%, 97%, 98%, 99%, or 100% amino acid sequence identity to SEQ ID NO:2. In certain embodiments, the nucleic acid sequence encodes a CD40L having an amino acid sequence having at least 95% amino acid sequence identity to SEQ ID NO:2. In certain embodiments, the nucleic acid sequence encodes a CD40L having an amino acid sequence having at least 96% amino acid sequence identity to SEQ ID NO:2. In certain embodiments, the nucleic acid sequence encodes a CD40L having an amino acid sequence having at least 97% amino acid sequence identity to SEQ ID NO:2. In certain embodiments, the nucleic acid sequence encodes a CD40L having an amino acid sequence having at least 98% amino acid sequence identity to SEQ ID NO:2. In certain embodiments, the nucleic acid sequence encodes a CD40L having an amino acid sequence having at least 99% amino acid sequence identity to SEQ ID NO:2. In certain embodiments, the nucleic acid sequence encodes a CD40L having the amino acid sequence of SEQ ID NO:2.

In certain embodiments, the immunogenic compositions comprise at least two recombinant poxviruses (e.g., MVA), one comprising a nucleic acid encoding CD40L and one comprising a nucleic acid encoding a heterologous disease-associated antigen, wherein the immunogenic composition induces increased T-cell immune responses specific for the heterologous disease-associated antigen when administered to a human host.

Nucleic acids encoding CD40L can be operatively linked to expression control sequences. An expression control sequence operatively linked to a coding sequence is joined such that expression of the coding sequence is achieved under conditions compatible with the expression control sequences. The expression control sequences include, but are not limited to, appropriate promoters, enhancers, transcription terminators, a start codon at the beginning a protein-encoding open reading frame, splicing signals for introns, and in-frame stop codons. Suitable promoters include, but are not limited to, the SV40 early promoter, the retrovirus LTR, the adenovirus major late promoter, the human CMV immediate early I promoter, and various poxvirus promoters including, but not limited to the following vaccinia virus or MVA-derived promoters: the 30K promoter, the I3 promoter, the sE/L promoter, the Pr7.5K, the 40K promoter, the Cl promoter, the PrSynIIm promoter, the PrLE1 promoter, the PrH5m promoter, the PrS promoter, a hybrid early/late promoter, the PrS5E promoter, the PrA5E promoter, and the Pr4LS5E promoter; a cowpox virus ATI promoter, or the following fowlpox-derived promoters: the Pr7.5K promoter, the I3 promoter, the 30K promoter, or the 40K promoter.

Additional expression control sequences include, but are not limited to, leader sequences, termination codons, polyadenylation signals and any other sequences necessary for the appropriate transcription and subsequent translation of the nucleic acid sequence encoding the desired recombinant protein (e.g., CD40L) in the desired host system. The recombinant poxviruses (e.g., MVA) may also contain additional elements necessary for the transfer and subsequent replication of the expression vector containing the nucleic acid sequence in the desired host system. It will further be understood by one skilled in the art that such vectors are easily constructed using conventional methods (Ausubel et al., (1987) in "Current Protocols in Molecular Biology," John Wiley and Sons, New York, N.Y.) and are commercially available.

In certain embodiments, the recombinant poxviruses (e.g., MVA) disclosed herein further comprise nucleic acid molecules encoding one or more costimulatory molecules. In certain embodiments, the one or more costimulatory molecules are selected from the group consisting of B7-1, B7-2, ICAM-1, LFA-3, 4-1BBL, CD59, CD40, CD70, VCAM-1 and OX-40L. In certain embodiments, the recombinant poxviruses (e.g., MVA) disclosed herein further comprise a nucleic acid molecule encoding one costimulatory molecule. In certain embodiments, the recombinant poxviruses (e.g., MVA) disclosed herein further comprise one or more nucleic acid molecules encoding two costimulatory molecules. In certain embodiments, the recombinant poxviruses (e.g., MVA) disclosed herein further comprise one or more nucleic acid molecules encoding three costimulatory molecules. In certain embodiments, the three costimulatory molecules are B7-1, ICAM-1, and LFA-3 TRICOM). In certain embodiments, the recombinant poxviruses (e.g., MVA) comprise one or more nucleic acid molecules encoding human B7.1, human ICAM-1, and human LFA-3. In certain embodiments, the nucleic acid molecules encoding B7-1, ICAM-1, and LFA-3 are under the control of the same expression control sequences. In certain embodiments, the nucleic acids encoding B7-1, ICAM-1, and LFA-3 are under control of different expression control sequences.

The use of at least three costimulatory molecules produces a synergistic enhancement of the immune response induced by the recombinant poxviruses (e.g., MVA) encoding CD40L, and the synergy is not obtainable using only one or two costimulatory molecules. Effective combinations of costimulatory molecules are selected from the group consisting of: B7-1, ICAM-1, and LFA-3; B7-1, B7-2, ICAM-1, and LFA-3; B7-1, B7-2, ICAM-1, and 4-1BBL; B7-1, B7-2, ICAM-1, LFA-3, and 4-1BBL; CD59 and VCAM-1; B7-1 and B7-2; CD59, CD40, 4-1 BBL, and CD70; VCAM-1, B7-1, and B7-2; and OX-40L and 4-1BBL; and the like, depending on the desired immune response and the disease or condition to be treated (see, e.g., U.S. Pat. No. 7,211,432, which is hereby incorporated herein by reference in its entirety).

Genes or functional portions thereof encoding costimulatory molecules that can be incorporated into the recombinant poxviruses (e.g., MVA) disclosed herein include but are not limited to B7-1, B7-2, ICAM-1, LFA-3, 4-1BBL, CD59, CD40, CD70, OX-40L, and their mammalian homologs.

The term "B7" refers to a family of costimulatory molecules which are members of the immunoglobulin ("Ig") gene superfamily. The members include B7-1 (also known as "CD80") and B7-2 (also known as "CD86"), which are the natural ligands of CD28 and CTLA-4 (also known as "CD152"). The gene sequence of mouse B7.1 is deposited in GenBank under Accession No. X60958. See, e.g., Freeman et al., J. Immunol. 143:2714-2722 (1989). The gene sequence of mouse B7.2 is deposited in GenBank under Accession No. L25606. See, e.g., Azuma et al., Nature 366:76-79 (1993). The human homologs of the mouse B7-1 and B7-2 costimulatory molecules include CD80, the homolog of mouse B7.1, and CD86, the homolog of mouse B7.2. The gene sequence of human B7.1 is deposited in GenBank under Accession No. M27533. The gene sequence of human B7.2 (CD86) is deposited in GenBank under Accession Nos. U04343 and AF099105.

The term "intercellular adhesion molecule" ("ICAM") refers to a family of costimulatory molecules which are members of the Ig gene superfamily. The members include ICAM-1 (also known as "CD54"), ICAM-2 (also known as "CD102"), ICAM-3 (also known as "CD50"), ICAM-4 (also known as "CD242"), and ICAM-5, which are the natural ligands of the leukocyte integrins CD11a/CD18 (also known as "leukocyte function-associated antigen-1" or "LFA-1") which are expressed on the surface of lymphocytes and granulocytes. The gene sequence of human ICAM-1 is deposited in GenBank under Accession No. J03132. The gene sequence of mouse ICAM-1 is deposited in GenBank under Accession No. X52264.

The term "leukocyte function-associated antigen" ("LFA") refers to a family of costimulatory molecules involved in cell adhesion. The members include LFA-1 (also known as "CD11a/CD18", LFA-2 (also known as "CD2"), and LFA-3 (also known as "CD58"). LFA-3, a glycosyl-phosphatidylinositol-linked glycoprotein, is a member of the CD2 family of the Ig gene superfamily. The natural ligand of LFA-3 is CD2 (also known as "LFA-2") which is expressed on thymocytes, T-cells, B-cells and natural killer ("NK") cells. The gene sequence of human LFA-3 is deposited in GenBank under Accession No. Y00636. The gene sequence of mouse LFA-3 is deposited in GenBank under Accession No. X53526.

Examples of poxvirus strains that are useful in the practice of the present invention include, but are not limited to orthopox viruses, avipox viruses, parapox viruses, yatapox viruses, and molluscipox viruses, but preferably the orthopox and/or avipox viruses. In certain embodiments, the recombinant poxvirus is selected from the group consisting of orthopox viruses, avipox viruses, parapox viruses, yatapox viruses, and molluscipox viruses. In certain embodiments, the recombinant poxvirus is an avipox virus. In certain embodiments, the avipox virus is selected from the group consisting of canarypox virus and fowlpox virus. In certain embodiments, the avipox virus is canarypox virus. In certain embodiments, the avipox virus is fowlpox virus.

In certain embodiments, the recombinant poxvirus is an orthopox virus. In certain embodiments, the orthopox virus is selected from the group consisting of vaccinia virus, cowpox virus, and monkeypox virus. In certain embodiments, the orthopox virus is vaccinia virus. In certain embodiments, the vaccinia virus is selected from the group consisting of wild-type vaccinia virus, vaccinia virus-Western Reserve, vaccinia virus-Copenhagen, Dryvax (also known as vaccinia virus-Wyeth), ACAM2000, and MVA.

Examples of MVA virus strains that are useful in the practice of the present invention and that have been deposited in compliance with the requirements of the Budapest Treaty are strains MVA 572, deposited at the European Collection of Animal Cell Cultures (ECACC), Vaccine Research and Production Laboratory, Public Health Laboratory Service, Centre for Applied Microbiology and Research, Porton Down, Salisbury, Wiltshire SP4 OJG, United Kingdom, under the deposition number ECACC 94012707 on Jan. 27, 1994, and MVA 575 deposited at the European Collection of Animal Cell Cultures (ECACC) under deposition number ECACC 00120707 on Dec. 7, 2000. MVA-BN®, deposited on Aug. 30, 2000, at the European Collection of Animal Cell Cultures (ECACC) under deposition number V00083008, and its derivatives, are additional exemplary strains.

In certain embodiments, the recombinant MVA is MVA-572. In certain embodiments, the recombinant MVA is MVA-575. In certain embodiments, the recombinant MVA is MVA-BN or a derivative thereof.

In certain embodiments, the increased T-cell immune response comprises greater numbers of cytotoxic T-cells (CTLs) specific for the heterologous disease-associated antigen. In certain embodiments, the greater numbers of CTLs specific for the heterologous disease-associated antigen also display increased cytolytic activity compared to CTLs induced by administration of a recombinant MVA comprising a nucleic acid sequence encoding a heterologous disease-associated antigen but not a nucleic acid sequence encoding a CD40L. In certain embodiments, the increased T-cell immune response comprises greater numbers of memory T-cells specific for the heterologous disease-associated antigen. In certain embodiments, the increased T-cell immune response comprises greater numbers of CTLs specific for the heterologous disease-associated antigen and greater numbers of memory T-cells specific for the heterologous disease-associated antigen. In certain embodiments, the greater numbers of CTLs specific for the heterologous disease-associated antigen also display increased cytolytic activity compared to CTLs induced by administration of a recombinant MVA comprising a nucleic acid sequence encoding a heterologous disease-associated antigen but not a nucleic acid sequence encoding a CD40L.

In certain embodiments, the heterologous disease-associated antigen is an infectious disease antigen or a tumor-associated antigen. In certain embodiments, the heterologous disease-associated antigen is a tumor-associated antigen. In certain embodiments, the tumor-associated antigen is selected from the group consisting of 5-α-reductase, α-fetoprotein ("AFP"), AM-1, APC, April, B melanoma antigen gene ("BAGE"), β-catenin, Bcl12, bcr-abl, Brachyury, CA-125, caspase-8 ("CASP-8", also known as "FLICE"), Cathepsins, CD19, CD20, CD21/complement receptor 2 ("CR2"), CD22/BL-CAM, CD23/$F_c\varepsilon$RII, CD33, CD35/complement receptor 1 ("CR1"), CD44/PGP-1, CD45/leukocyte common antigen ("LCA"), CD46/membrane cofactor protein ("MCP"), CD52/CAMPATH-1, CD55/decay accelerating factor ("DAF"), CD59/protectin, CDC27, CDK4, carcinoembryonic antigen ("CEA"), c-myc, cyclooxygenase-2 ("cox-2"), deleted in colorectal cancer gene ("DCC"), DcR3, E6/E7, CGFR, EMBP, Dna78, farnesyl transferase, fibroblast growth factor-8a ("FGF8a"), fibroblast growth factor-8b ("FGF8b"), FLK-1/KDR, folic acid receptor, G250, G melanoma antigen gene family ("GAGE-family"), gastrin 17, gastrin-releasing hormone, ganglioside 2 ("GD2")/ganglioside 3 ("GD3")/ganglioside-monosialic acid-2 ("GM2"), gonadotropin releasing hormone ("GnRH"), UDP-GlcNAc:$R_1$Man($\alpha$1-6)$R_2$ [GlcNAc to Man ($\alpha$1-6)] β1,6-N-acetylglucosaminyltransferase V ("GnT V"), GP1, gp100/Pme117, gp-100-in4, gp15, gp75/tyrosine-related protein-1 ("gp75/TRP-1"), human chorionic gonadotropin ("hCG"), heparanase, Her2/neu, human mammary tumor virus ("HMTV"), 70 kiloDalton heat-shock protein ("HSP70"), human telomerase reverse transcriptase ("hTERT"), insulin-like growth factor receptor-1 ("IGFR-1"), interleukin-13 receptor ("IL-13R"), inducible nitric oxide synthase ("iNOS"), Ki67, KIAA0205, K-ras, H-ras, N-ras, KSA, LKLR-FUT, melanoma antigen-encoding family ("MAGE-family", including at least MAGE-1, MAGE-2, MAGE-3, and MAGE-4), mammaglobin, MAP17, Melan- A/melanoma antigen recognized by T-cells-1 ("MART-1"), mesothelin, MIC A/B, MT-MMPs, mucin, testes-specific antigen NY-ESO-1, osteonectin, p15, P170/MDR1, p53, p97/melanotransferrin, PAI-1, platelet-derived growth factor ("PDGF"), µPA, FRAME, probasin, progenipoietin, prostate-specific antigen ("PSA"), prostate-specific membrane antigen ("PSMA"), RAGE-1, Rb, RCAS1, SART-1, SSX-family, STAT3, STn, TAG-72, transforming growth factor-alpha ("TGF-α"), transforming growth factor-beta ("TGF-β"), Thymosin-beta-15, tumor necrosis factor-alpha ("TNF-α"), TP1, TRP-2, tyrosinase, vascular endothelial growth factor ("VEGF"), ZAG, p16INK4, and glutathione-S-transferase ("GST"). In certain embodiments, the tumor-associated antigen is brachyury. In certain embodiments, the tumor-associated antigen is PSA. In certain embodiments, the tumor-associated antigen is CEA. In certain embodiments, the tumor-associated antigen is MUC-1. In certain embodiments, the tumor-associated antigen is CEA and MUC-1.

In certain embodiments, the heterologous disease-associated antigen is an infectious disease antigen. In certain embodiments, the infectious disease antigen is a viral antigen, a bacterial antigen, a fungal antigen, or a parasite antigen.

In certain embodiments, the infectious disease antigen is a viral antigen. In certain embodiments, the infectious disease antigen is selected from the group consisting of antigens derived from adenovirus, Coxsackievirus, Crimean-Congo hemorrhagic fever virus, cytomegalovirus ("CMV"), dengue virus, Ebola virus, Epstein-Barr virus ("EBV"), Guanarito virus, herpes simplex virus-type 1 ("HSV-1"), herpes simplex virus-type 2 ("HSV-2"), human herpesvirus-type 8 ("HHV-8"), hepatitis A virus ("HAV"), hepatitis B virus ("HBV"), hepatitis C virus ("HCV"), hepatitis D virus ("HDV"), hepatitis E virus ("HEV"), human immunodeficiency virus ("HIV"), influenza virus, Junin virus, Lassa virus, Machupo virus, Marburg virus, measles virus, human metapneumovirus, mumps virus, Norwalk virus, human papillomavirus ("HPV"), parainfluenza virus, parvovirus, poliovirus, rabies virus, respiratory syncytial virus ("RSV"), rhinovirus, rotavirus, rubella virus, Sabia virus, severe acute respiratory syndrome virus ("SARS"), varicella zoster virus, variola virus, West Nile virus, and yellow fever virus. In certain embodiments, the viral antigen is derived from RSV. In certain embodiments, the viral antigen is derived from Ebola virus. In certain embodiments, the viral antigen is derived from Marburg virus. In certain embodiments, the viral antigen is derived from HIV. In certain embodiments, the viral antigen is derived from influenza virus. In certain embodiments, the viral antigen is derived from dengue virus. In certain embodiments, the viral antigen is derived from yellow fever virus.

In certain embodiments, the infectious disease antigen is a bacterial antigen. In certain embodiments, the bacterial antigen is selected from the group consisting of antigens derived from *Bacillus anthracis, Bordetella pertussis, Borrelia burgdorferi, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diptheriae, Enterococcus faecalis, Enterococcus faecium, Escherichia coli,* enterotoxigenic *Escherichia coli,* enteropathogenic *Escherichia coli, Escherichia coli)* 157: H7, *Francisella tularensis, Haemophilus influenza, Helicobacter pylori, Legionella pneumophila, Leptospira interrogans, Listeria monocytogenes, Mycobacterium leprae, Mycobacterium tuberculosis, Mycoplasma pneumoniae, Neisseria gonorrhoeae, Neisseria meningitides, Pseudomonas aeruginosa, Rickettsia rickettsia, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholerae,* and *Yersinia pestis.* In certain embodiments, the bacterial antigen is derived from *Bacillus anthracis.*

In certain embodiments, the infectious disease antigen is a fungal antigen. In certain embodiments, the fungal antigen is selected from the group consisting of antigens derived from *Aspergillus clavatus, Aspergillus flavus, Aspergillus fumigatus, Aspergillus nidulans, Aspergillus niger, Aspergillus terreus, Blastomyces dermatitidis, Candida albicans, Candida dubliniensis, Candida glabrata, Candida parapsilosis, Candida rugosa, Candida tropicalis, Cryptococcus albidus, Cryptococcus Cryptococcus laurentii, Cryptococcus neoformans, Histoplasma capsulatum, Microsporum canis, Pneumocystis carinii, Pneumocystis jirovecii, Sporothrix schenckii, Stachbotrys chartarum, Tinea barbae, Tinea captitis, Tinea corporis, Tinea cruris, Tinea faciei, Tinea incognito, Tinea nigra, Tinea versicolor, Trichophyton rubrum* and *Trichophyton tonsurans.*

In certain embodiments, the infectious disease antigen is a parasite antigen. In certain embodiments, the parasite antigen is selected from the group consisting of antigens derived from *Anisakis* spp. *Babesia* spp., *Baylisascaris procyonis, Cryptosporidium* spp., *Cyclospora cayetanensis, Diphyllobothrium* spp., *Dracunculus medinensis, Entamoeba histolytica, Giardia duodenalis, Giardia intestinalis, Giardia lamblia, Leishmania* sp., *Plasmodium falciparum, Schistosoma mansoni, Schistosoma haematobium, Schistosoma japonicum, Taenia* spp., *Toxoplasma gondii, Trichinella spiralis,* and *Trypanosoma cruzi.*

Pharmaceutical Compositions

In certain embodiments, any of the the immunogenic compositions provided herein further comprise a pharmaceutically-acceptable carrier. In certain embodiments, the immunogenic composition can be formulated in solution in a concentration range of $10^4$ to $10^9$ $TCID_{50}$/ml, $10^5$ to $5\times10^8$ $TCID_{50}$/ml, $10^6$ to $10^8$ $TCID_{50}$/ml, or $10^7$ to $10^8$ $TCID_{50}$/ml. A preferred dose for humans comprises between $10^6$ to $10^9$ $TCID_{50}$, including a dose of $10^6$ $TCID_{50}$, $10^7$ $TCID_{50}$, $10^8$ $TCID_{50}$ or $5\times10^8$ $TCID_{50}$.

The immunogenic compositions provided herein may generally include one or more pharmaceutically-acceptable and/or approved carriers, additives, antibiotics, preservatives, adjuvants, diluents and/or stabilizers. Such auxiliary substances can be water, saline, glycerol, ethanol, wetting or emulsifying agents, pH buffering substances, or the like. Suitable carriers are typically large, slowly metabolized molecules such as proteins, polysaccharides, polylactic acids, polyglycolic acids, polymeric amino acids, amino acid copolymers, lipid aggregates, or the like.

For the preparation of vaccines, the immunogenic compositions provided herein can be converted into a physiologically acceptable form. This can be done based on experience in the preparation of poxvirus vaccines used for vaccination against smallpox as described by H. Stickl et al., Dtsch. med. Wschr. 99:2386-2392 (1974).

For example, purified viruses can be stored at −80° C. with a titer of $5\times10^8$ $TCID_{50}$/ml formulated in about 10 mM Tris, 140 mM NaCl pH 7.7. For the preparation of vaccine shots, e.g., $10^2$-$10^8$ or $10^2$-$10^9$ particles of the virus can be lyophilized in 100 ml of phosphate-buffered saline (PBS) in the presence of 2% peptone and 1% human albumin in an ampoule, preferably a glass ampoule. Alternatively, the vaccine shots can be produced by stepwise freeze-drying of the virus in a formulation. This formulation can contain additional additives such as mannitol, dextran, sugar, glycine, lactose or polyvinylpyrrolidone or other aids such as antioxidants or inert gas, stabilizers or recombinant proteins (e.g., human serum albumin) suitable for in vivo administration. The glass ampoule is then sealed and can be stored between 4° C. and room temperature for several months. However, as long as no need exists, the ampoule is stored preferably at temperatures below −20° C.

For vaccination or therapy, the lyophilisate can be dissolved in an aqueous solution, preferably physiological saline or Tris buffer, and administered either systemically or locally, i.e., parenteral, subcutaneous, intravenous, intramuscular, intranasal, or any other path of administration known to the skilled practitioner. The mode of administration, the dose and the number of administrations can be optimized by those skilled in the art in a known manner. However, most commonly a patient is vaccinated with a second shot about one month to six weeks after the first vaccination shot.

Kits Comprising Immunogenic Compositions

Also provided herein are kits comprising any one or more of the immunogenic compositions disclosed herein. The kits can comprise one or multiple containers or vials of the immunogenic compositions, together with instructions for the administration of the immunogenic compositions to a subject at risk of contracting an infectious disease or having a tumor. In certain embodiments, the subject is a human. The instructions may indicate that the immunogenic composition should be administered to the subject in a single dose, or in multiple (i.e., 2, 3, 4, etc.) doses. In certain embodiments, the instructions indicate that the immunogenic composition should be administered in a first (priming) and one or more subsequent boosting administrations to naïve or non-naïve subjects. Further provided are kits comprising the immunogenic compositions in a first vial or container for a first administration (priming) and in one or more additional vials or containers for one or more subsequent boosting administrations.

Methods and Uses of Recombinant MVA Viruses

Also provided herein are methods of enhancing an antigen-specific immune response to a disease-associated antigen comprising administering any of the immunogenic compositions provided herein to a subject in need thereof, wherein the immunogenic composition induces increased T-cell immune responses specific for the heterologous disease-associated antigen when administered to the subject, as well as any of the immunogenic compositions provided herein for use in methods of immunizing a subject and use of any of the immunogenic compositions provided herein in the preparation of a medicament for immunizing a subject.

In certain embodiments, the subject is a mammal. In certain embodiments, the mammal is a rat, rabbit, pig, mouse, or human, and the methods comprise administering a dose of any one or more of the immunogenic compositions provided herein to the subject.

The subject is preferably a human and may be an adult. In certain embodiments, the adult is over the age of 50, 55, 60, 65, 70, 75, 80, or 85 years. In certain embodiments, the subject is less than 5 years, less than 3 years, less than 2 years, less than 15 months, less than 12 months, less than 9 months, less than 6 months, or less than 3 months of age. In certain embodiments, the subject is 0-3 months, 3-6 months, 6-9 months, 9-12 months, 1-2 years, or 2-5 years of age. In certain embodiments, the subject is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75 or more years old.

In certain embodiments, any of the immunogenic compositions provided herein are administered to the subject at a dose of $10^6$ to $10^9$ $TCID_{50}$, at a dose of $10^6$ to $5\times10^8$ $TCID_{50}$. or $10^7$ to $10^8$ $TCID_{50}$. The immunogenic compositions provided herein may also be administered to the subject at a dose of $10^6$, $10^7$ $TCID_{50}$, $10^8$, or $5\times10^8$ $TCID_{50}$. In certain embodiments, any of the immunogenic compositions provided herein are administered to a human subject at a dose of $10^7$ $TCID_{50}$, $10^8$, or $5\times10^8$ $TCID_{50}$.

In certain embodiments, the immunogenic compositions comprise at least two recombinant poxviruses (e g., MVA), one comprising a nucleic acid encoding CD40L and one comprising a nucleic acid encoding a heterologous disease-associated antigen, wherein the immunogenic composition induces increased T-cell immune responses specific for the heterologous disease-associated antigen when administered to a human host.

In certain embodiments, the immunogenic compositions provided herein are administered to the subject in a single dose, or in multiple (i.e., 2, 3, 4, etc.) doses. In certain embodiments, the immunogenic compositions are administered in a first (priming) inoculation and one or more subsequent boosting administrations. In certain embodiments, the first dose comprises $10^7$ to $10^8$ $TCID_{50}$ of the immunogenic composition and the second dose comprises $10^7$ to $10^8$ $TCID_{50}$ of the immunogenic composition.

In certain embodiments, the one or more subsequent boosting administrations comprise the same recombinant poxvirus vector as previously administered and the methods comprise a homologous prime-boost vaccination. In certain embodiments, the one or more subsequent boosting administrations comprise a different recombinant poxvirus vector than previously administered and the methods comprise a heterologous prime-boost vaccination. In certain embodiments, the first poxvirus vector (i.e., the priming vaccination) administered is an orthopox virus vector. In certain embodiments, the orthopox virus vector is an MVA or an MVA-BN. In certain embodiments, the second poxvirus vector (i.e., the one or more boosting vaccinations) administered is an avipox virus. In certain embodiments, the second recombinant poxvirus vector (i.e., the one or more boosting vaccinations) administered is an avipox virus. In certain embodiments, the avipox virus vector is a canary pox virus vector or a fowlpox virus vector. In certain embodiments, the avipox virus vector is a canary pox virus vector. In certain embodiments, the avipox virus vector is a fowlpox virus vector.

In certain embodiments, the one or more subsequent administrations (i.e., the one or more boosting vaccinations) are administered at intervals comprising days, weeks or months after administration of the initial priming vaccination. In certain embodiments, the one or more subsequent administrations of a recombinant poxvirus vector (i.e., the one or more boosting vaccinations) are administered at intervals of 1, 2, 3, 4, 5, 6, 7 or more days after administration of the initial amount of a recombinant poxvirus vector (i.e., the priming vaccination). In certain embodiments, the one or more subsequent administrations of a recombinant poxvirus vector (i.e., the one or more boosting vaccinations) are administered at intervals of 1, 2, 3, 4, 5, 6, 7, 8 or more weeks after administration of the initial amount of a recombinant poxvirus vector (i.e., the priming vaccination). In certain embodiments, the one or more subsequent administrations of a recombinant poxvirus vector (i.e., the one or more boosting vaccinations) are administered at intervals of 1, 2, 3, 4, 5, 6, 7, 8, 9, 10, 11, 12 or more months after administration of the initial priming vaccination. In certain embodiments, the one or more subsequent administrations of a recombinant poxvirus vector (i.e., the one or more boosting vaccinations) are administered at any combination of intervals after administration of the initial priming vaccination (e.g., 1, 2, 3, 4, 5, 6, 7 or more days, 1, 2, 3, 4, 5, 6, 7, 8 or more weeks, or 1, 2, 3, 4, 5, 6, 7, 8, 9, 10, 11, 12 or more months) disclosed herein.

In certain embodiments, the immunogenic compositions can be administered systemically or locally, parenterally, subcutaneously, intravenously, intramuscularly, or intranasally, preferably subcutaneously or intranasally. The immunogenic compositions can also be administered by any other path of administration known to the skilled practitioner.

EXAMPLES

Example 1

Materials and Methods

Mice. Mice were bred and maintained either in the animal facilities at Bavarian Nordic GmbH or at the University of Zurich according to institutional guidelines. C57BL/6J (H-2$^b$) and CBA/J (H-2$^k$) mice were purchased from Elevage Janvier (Le Genest, France). MHC class II deficient (MHC II$^{-/-}$), CD40 deficient (CD40$^{-/-}$), CD40L deficient (CD40L$^{-/-}$) and JHT mice were on a C57BL/6 background and were obtained from the animal facility of the University Zurich.

Generation of MVA-BN recombinants. All recombinant virus vectors used for this study were based on a cloned version of MVA-BN® in a bacterial artificial chromosome (BAC). MVA-BN® was developed by Bavarian Nordic and is deposited at the European Collection of Cell Cultures (ECACC) under Accession No. V00083008. The generation of MVA recombinants was carried out as described recently (Baur et al., "Immediate-early expression of a recombinant antigen by modified vaccinia virus Ankara breaks the immunodominance of strong vector-specific B8R antigen in acute and memory CD8 T-cell responses," *J. Virol.* 84(17):8743-52 (2010)). Briefly, the sequence of the strong synthetic early-late pS promoter comprises 40 nucleotides exactly matching the previously described sequence (Chakrabarti et al., "Compact, synthetic vaccinia virus early/late promoter for protein expression," *BioTechniques* 23(6):1094-97 (1997)). The pS promoter was cloned upstream of the open reading frame for chicken ovalbumin (OVA). The pHyb promoter was developed and described by Baur and colleagues (Baur et al. (2010)) and comprises a late element from the promoter directing the expression of the ATI protein in cowpox virus (Funahashi et al., "Cloning and characterization of the gene encoding the major protein of the A-type inclusion body of cowpox virus," *J. Gen. Virol.* 69(Pt. 1):35-47 (1988); and Patel et al., "A poxvirus-derived vector that directs high levels of expression of cloned genes in mammalian cells," *Proc. Nat'l Acad. Sci. USA* 85(24):9431-35 (1988)) and five tandemly arranged early elements derived from a modified p7.5 promoter (Davison et al., "Structure of vaccinia virus early promoters," *J. Mol. Biol.* 210(4):749-769 (1989). The pHyb promoter was cloned upstream of the open reading for murine CD40L. Infectious viruses were reconstituted from BACs by transfecting BAC DNA into BHK-21 cells and superinfecting them with Shope fibroma virus as a helper virus. After three additional passages on primary chicken embryo fibroblasts (CEF), helpervirus free MVA-OVA, MVA-OVA-CD40L and MVA-ZE-BOV-GP viruses were obtained. All viruses used in animal experiments were purified twice through a sucrose cushion. For the UV-inactivation of viruses concentrated virus stocks were UV irradiated with an UV Chamber (Genelinker GS, Bio-Rad Laboratories, Munich, Germany) in the presence of psoralen.

Immunization of mice. Intravenous (i.v.) injections were given into a lateral tail vein with a total volume of 200 µl containing 5×10$^7$ TCID$_{50}$ of the respective MVA recombinants. Where noted, 50 µg anti-CD40 antibody (BioXCell, West Lebanon, N.H., USA) was mixed with MVA recombinants or 100 µg EndoGrade Ovalbumin (Hyglos GmbH, Bernried am Starnberger See, Germany) prior to injection. For Ectromelia virus (ECTV, strain Moscow) infection mice were anaesthetized with ketamine/xylamine and virus (1×10$^5$ TCID$_{50}$) was applied by intranasal (i.n.) drop wise installation in a total volume of 50 µl. The health status of infected mice was checked daily. All animal experiments were approved by the government of Upper Bavaria (Regierung von Oberbayern) and were carried out in accordance with the guidelines for animal experiments at Bavarian Nordic GmbH.

Flow cytometry. Mononuclear cell suspensions were stained with appropriate dilutions of the following monoclonal antibodies: anti CD3-FITC, CD3-PECy7, CD4–APC-H7, CD8α-FITC, CD8α-PerCP-Cy5.5, CD19-FITC, CD19-PerCP-Cy5.5, CD44-FITC, CD62L-FITC, CD69-FITC, CD80-FITC, CD8O-PE, CD86-FITC, NK1.1-FITC, NK1.1-APC, NK1.1-PerCP-Cy5.5, IL-2-APC, TNF-α-PE (all BD Biosciences), CD4–Alexa700, CD3-PerCP-Cy5.5, CD8α-Alexa700, CD8α-eFluor450, CD11b-Alexa700, CD11c-PECy7, CD25-PE, CD44-PerCP-Cy5.5, CD44-APC-eFluor780, CD45R (B220)-eFluor780, CD86-eFluor605, CD127-PECy7, CD154 (CD40L)-eFluor780, H-2K$^b$/SIIN-FEKL-APC (25-D1.16), KLRG-1-PerCP-eFluor710, KLRG-1-FITC, IFNγ-PECy7, Bcl-2-FITC (all eBioscience, Frankfurt, Germany) and anti-huGranzyme B-PE (GRB04, Life Technologies GmbH, Darmstadt, Germany). APC-conjugated MHC class I H-2K$^b$ dextramers loaded with B8$_{20-27}$-peptide (SEQ ID NO:3—TSYKFESV) or PE-conjugated MHC class I H-2K$^b$ dextramers loaded with OVA$_{257-264}$-peptide (SEQ ID NO:4—SIINFEKL) were used according to the manufacturers' instructions (Immudex). For intracellular cytokine staining cells were incubated with 2.5 µg/ml of MHC class I restricted peptides (B$^8_{20-27}$, OVA$_{257-264}$ or ZEBOV-GP$_{577-584}$ (SEQ ID NO:5—TELRTFSI)) for 5-6 hours at 37° C. in complete RPMI in the presence of 1 µl/ml GolgiPlug (BD Biosciences, Heidelberg, Germany). Peptides were purchased from GenScript. Intracellular staining of IFN-γ, TNF-α and IL-2 was performed after fixation/permeabilization according to the manufacturers' instructions (BD Cytofix/Cytoperm, BD Biosciences, Heidelberg, Germany). In order to measure cell proliferation 100 µg EdU were injected i.v. into MVA immunized animals. Spleens were removed one hour later for surface staining and subsequent EdU staining according to the manufactures' instructions (Click-iT EdU Alexa Fluor488 Flow cytometry Assay Kit, Life Technologies GmbH, Darmstadt, Germany). For live/dead discrimination cells were stained before fixation according to the manufactures' instructions (LIVE/DEAD fixable violet dead cell staining kit, Life Technologies GmbH, Darmstadt, Germany). All cells were acquired using a digital flow cytometer (LSR II, BD Biosciences, Heidelberg, Germany) and data were analyzed with FlowJo software (Tree Star, Inc., Ashland, Oreg., USA).

In vivo CTL assay. The in vivo CTL assay was essentially performed as described before (Coles et al., "Progression of armed CTL from draining lymph node to spleen shortly after localized infection with herpes simplex virus 1," *J. Immunol.* 168(2):834-38 (2002)) but extended to two target cell populations. Briefly, mononuclear spleen cell suspensions from naïve mice were incubated at ~2×10$^7$ cells/ml with 20 μg/ml B8$_{20-27}$-peptide, OVA$_{257-264}$-peptide or without peptide for one hour at 37° C. Each spleen cell population was labeled with 5 μM CFSE (Life Technologies GmbH, Darmstadt, Germany), 0.5 μM CFSE or 5 μM eFluor670 (eBioscience, Frankfurt, Germany) for 10 minutes at 37° C. Labeling was stopped by addition of 10 ml FCS. Washed cells were mixed at a 1:1:1 ratio and 1-2×10$^7$ cells were injected i.v. into syngeneic naïve and immunized mice. Mice were sacrificed after 4 hours and mononuclear spleen cell suspensions prepared. Cells were analyzed flow cytometrically. Percent specific lysis (PSL) of fluorescent target cells was calculated as follows: ratio=percentage of unpulsed cells/percentage of pulsed cells; PSL=(1−ratio unprimed/ratio primed)×100.

In vitro DC stimulation and adoptive DC transfer. FLT3-L bone marrow culture derived dendritic cells (FLDC) were prepared as described (Hochrein et al., "Herpes simplex virus type-1 induces IFN-alpha production via Toll-like receptor 9-dependent and -independent pathways," *Proc. Nat'l Acad. Sci. USA* 101(31):11416-21 (2004)). For in vitro analysis of DC activation and gene expression, wt FLDCs were transduced with MVA-OVA or MVA-OVA-CD40L (MOI 2). 3, 6 and 9 hours later DCs were harvested and stained for flow cytometric analysis. Supernatant was kept for cytokine analysis. For DC immunization, wt and CD40$^{-/-}$ FLDCs were transduced with MVA-OVA or MVA-OVA-CD40L (MOI 2.5) for one hour at 37° C. 2×10$^7$ transduced FLDCs per mouse were injected i.v. into C57BL/6J and CD40$^{-/-}$ mice.

Cytokine detection. Cytokine concentrations in serum and supernatant of FLDC cultures were determined by FlowCytomix bead assay (eBioscience, Frankfurt, Germany) according to the manufacturers' instructions.

Example 2

MVA Induced CD8+ T-Cell Responses were Amplified by an Agonistic Anti-CD40 Antibody The combination of a Toll-like Receptor ("TLR") with a CD40 agonist has been shown to synergistically enhance antigen-specific CD4+ and CD8+ T-cell responses after protein immunization [C. L. Ahonen et al., "Combined TLR and CD40 triggering induces potent CD8+ T-cell expansion with variable dependence on type I IFN," *J. Exp. Med.* 199(6):775-784 (2004); J. S. Kurche et al., "Comparison of OX40 ligand and CD70 in the promotion of CD4+ T-cell responses," *J. Immunol.* 185(4):2106-2115 (2010)]. Because of the TLR-stimulating properties of MVA [J. Delaloye et al., "Innate immune sensing of modified vaccinia virus Ankara (MVA) is mediated by TLR2-TLR6, MDA-5 and the NALP3 inflammasome," *PLoS Pathogens* 5(6):e1000480 (2009)], it was hypothesized that co-administration of MVA and a CD40 agonist might lead to enhanced CD8+ T-cell responses. Therefore, we first set out to evaluate whether MVA-induced CD8+ T-cell responses could be amplified by an agonistic antibody to murine CD40.

Figure 1B:
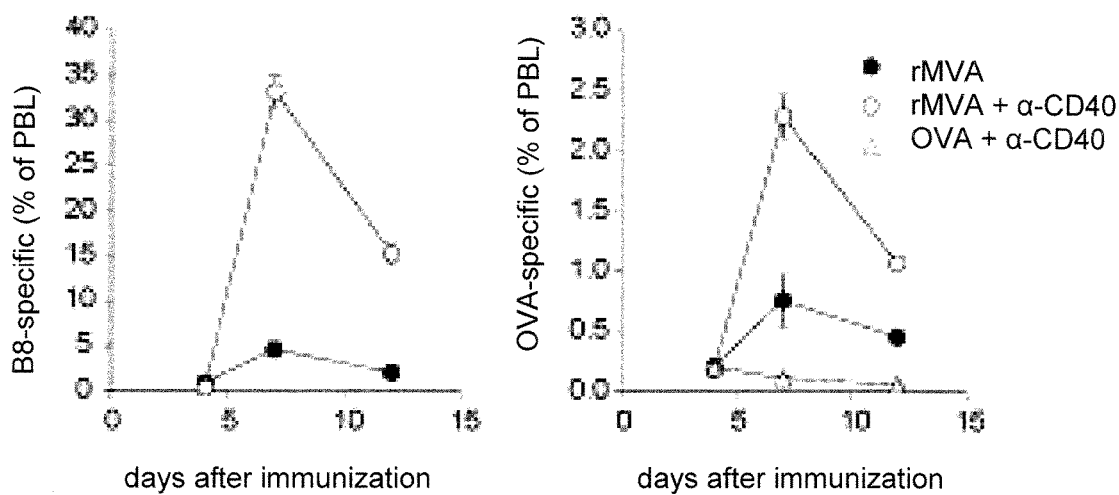
Figure 1C:
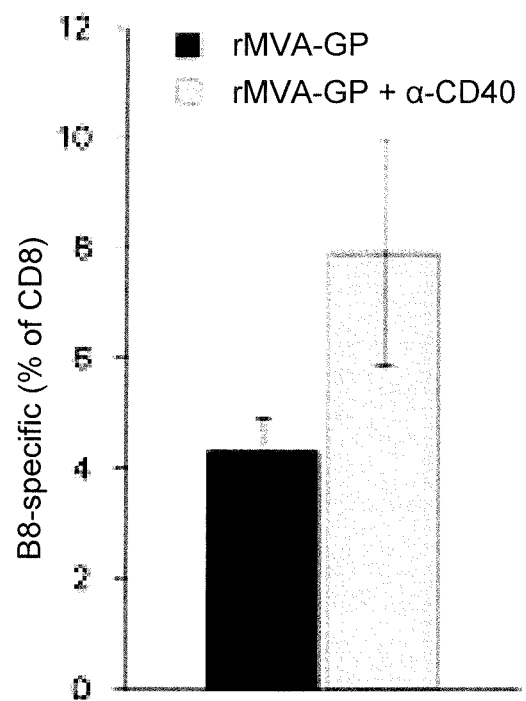

Mice were immunized with MVA-OVA (hereafter referred to as rMVA), rMVA mixed with anti-CD40 Ab or OVA protein combined with anti-CD40 Ab. Animals in this and all subsequent experiments were immunized with 5×10$^7$ TCID$_{50}$ of recombinant virus (e.g., MVA-OVA) via injection into the tail vein. MHC class I (H-2k$^b$) dextramers loaded with either the B8$_{20-27}$- or the OVA$_{257-264}$-peptidee were used to detect MVA- and OVA-specific CD8+ T-cell responses, respectively (FIG. 1A). Fluorescence-activated cell sorting ("FACS") analysis of peripheral blood lymphocytes ("PBL") done using standard methods revealed that rMVA immunization induced B8- and OVA-specific CD8+ T-cell responses and that these responses were enhanced ~7- and ~3-fold, respectively, by anti-CD40 Ab (FIG. 1B). OVA/anti-CD40 immunization, in contrast, did not lead to a detectable antigen-specific CD8+ T-cell response. In order to verify that these findings with the model antigen OVA were transferable to pathogen-derived antigens, the above experiment was repeated using recombinant MVA encoding the glycoprotein (GP) from Ebola virus Zaire (rMVA-GP). Ebola GP specific CD8+ T-cells were detected by intracellular cytokine staining with standard methods after restimulation with the H2-k$^k$ restricted peptide GP$_{577584}$ [M. Rao et al., "Cytotoxic T-lymphocytes to Ebola Zaire virus are induced in mice by immunization with liposomes containing lipid A," *Vaccine* 17(23-24):2991-2998 (1999)]. Again, a significantly enhanced (P<0.005) GP-specific CD8+ T-cell response was observed in the spleen of mice immunized with rMVA-GP+anti-CD40 (FIG. 1C).

Example 3

Construction and In Vitro Characterization of rMVA-CD40L

Figure 2:
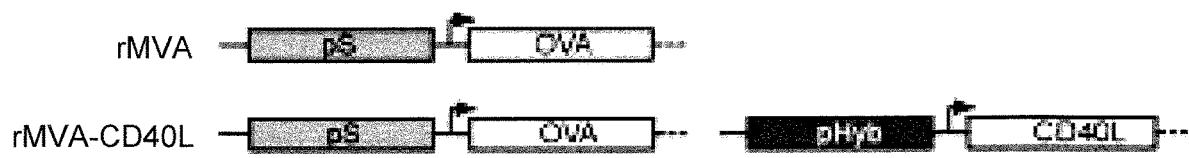
FIG. 2 shows a schematic representation of rMVA-OVA ("rMVA") and rMVA-OVA-CD40L ("rMVA-CD40L"). Recombinant MVA encoding OVA alone or OVA together with murine CD40L were generated as described in the Materials and Methods. OVA expression is controlled by the early/late synthetic promoter (pS) and CD40L expression by the recently described early/late hybrid promoter (pHyb) (Baur et al., 2010).

A CD40L expression cassette including the recently described early/late hybrid promoter (pHyb) [K. Baur et al., "Immediate-early expression of a recombinant antigen by modified vaccinia virus Ankara breaks the immunodominance of strong vector-specific B8R antigen in acute and memory CD8+ T-cell responses,"*J. Virol.* 84(17):8743-8752 (2010)] and the cDNA sequence of murine CD40L (FIG. 2) was inserted into a recombinant MVA expressing OVA under the control of the early/late synthetic promoter (pS) [S. Chakrabarti et al., "Compact, synthetic, vaccinia virus early/late promoter for protein expression," *Biotechniques* 23(6): 1094-1097 (1997)]. This promoter choice results in simultaneous expression of antigen and CD40L. The model antigen OVA instead of Ebola GP was used because more analytical tools are available for OVA and the above-described experiments suggested that OVA-based findings were likely to be applicable to other antigens as well.

Figure 3A:
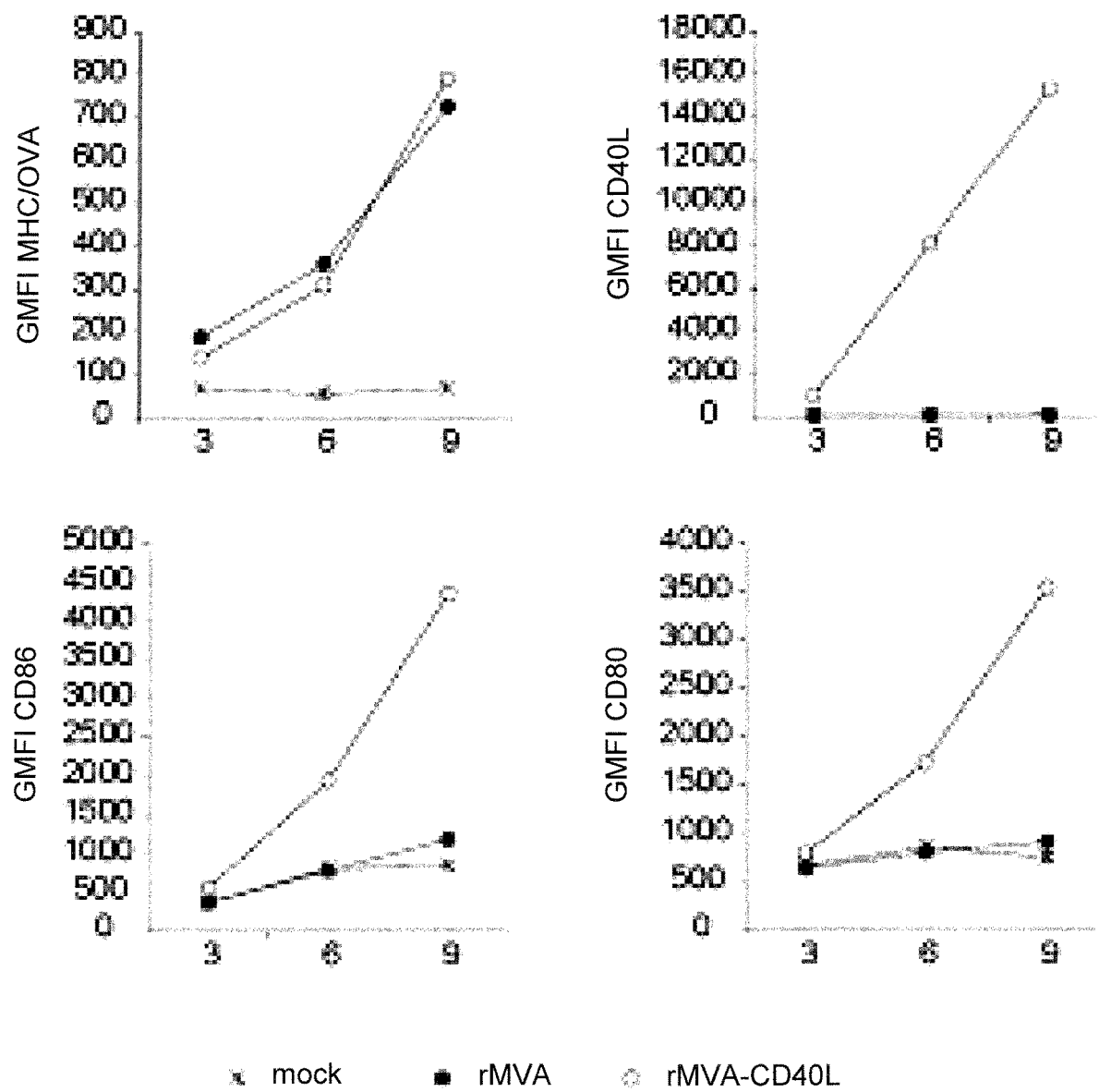
FIG. 3 shows that transduction of FLDCs in vitro with rMVA-CD40L leads to superior DC activation and cytokine secretion. In vitro-generated FLDCs were transduced with rMVA or rMVA-CD40L (MOI=2). (A) 3, 6 and 9 hours after transduction DCs were analyzed for OVA (H-2k$^b$/OVA$_{257-264}$ complexes) and CD40L expression and the activation markers CD86 and CD80. Note that OVA expression is not different between rMVA and rMVA-CD40L. (B) At the same points as in (A), supernatants were analyzed for IL-6, IL-12p70, TNF-$\alpha$ and IFN-$\alpha$ by a cytometric bead assay. Note that IL-12p70 and TNF-$\alpha$ were only detectable after transduction with rMVA-CD40L but not rMVA. Data represent at least two independent experiments. Shown is the mean of duplicate samples.
Figure 3B:
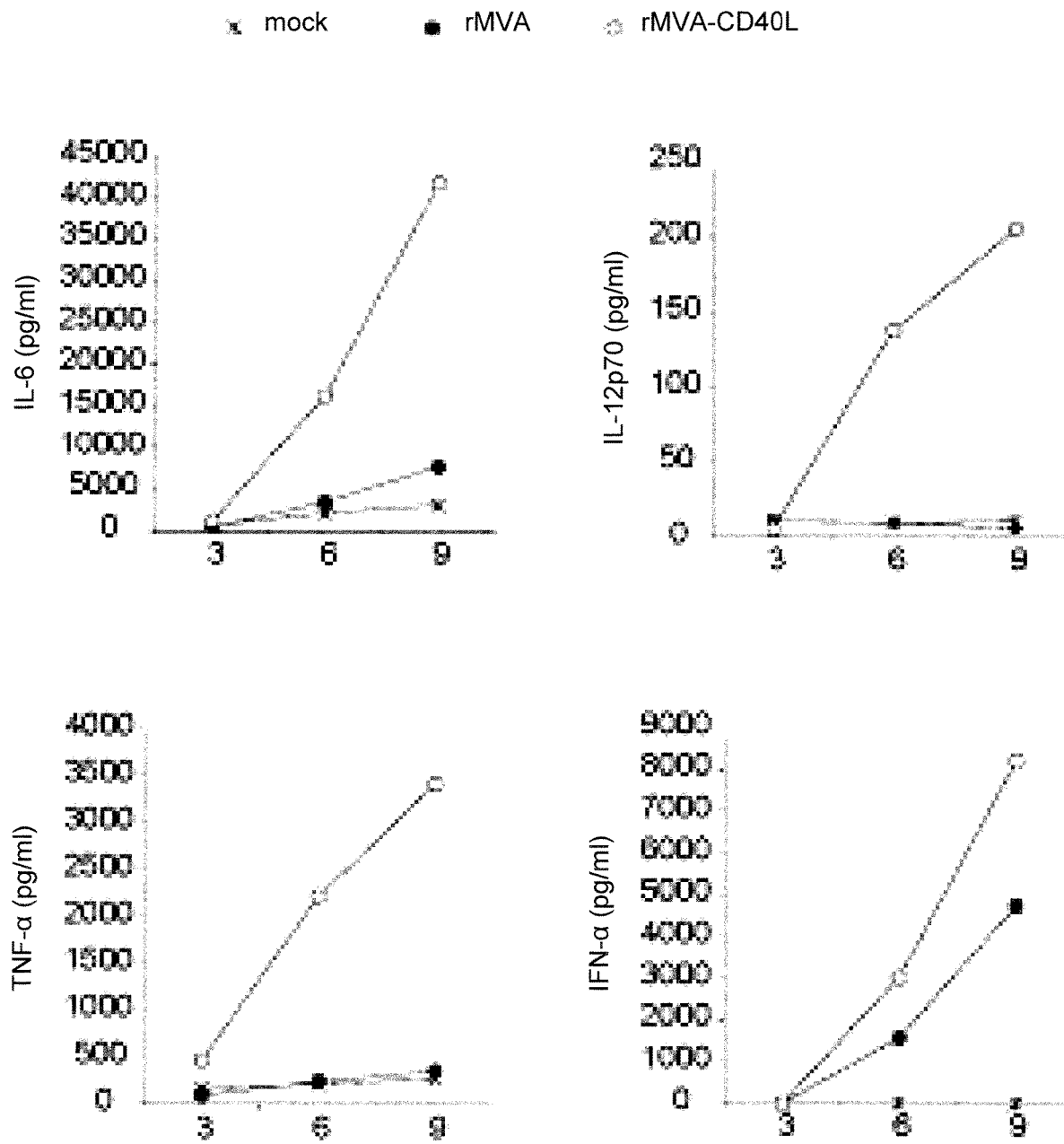

The expression of OVA and CD40L was verified by transducing bone marrow DCs ("BMDCs") with rMVA or rMVA-CD40L. OVA expression was measured by using the 25-D1.16 antibody that specifically detects H-2k$^b$/OVA$_{257-264}$ complexes [A. Porgador et al., "Localization, quantitation, and in situ detection of specific peptide-MHC class I complexes using a monoclonal antibody," *Immunity* 6(6): 715-726 (1997)]. As shown in FIG. 3A (upper row), OVA expression was readily detected after 3 hours and continued to increase during the observation period of 9 hours. While there was no difference in OVA expression in rMVA or rMVA-CD40L-transduced cells, CD40L was exclusively expressed in cells transduced with the latter. Importantly, H-2k$^b$/OVA$_{257-264}$ complexes and CD40L appeared synchronously on the cell surface of transduced DCs, ensuring the isochronic availability of antigen and co-stimulus. The same cells were also analyzed for expression of the two activation markers CD86 and CD80. rMVA-transduced BMDCs showed only weak signs of activation after 9 hours compared to untreated cells (FIG. 3A, bottom row). In contrast, the geometric mean fluorescence intensity ("GMFI") of CD86 and CD80 was 3-to-4-fold higher after 9 hours in rMVA-CD40L-transduced cells compared to rMVA-transduced cells. In order to further compare the in vitro immunogenicity of the two constructs, the amount of secreted cytokines in the supernatant of transduced DCs was measured. Both rMVA- and rMVA-CD40L-transduced cells secreted IL-6 and IFN-a above background levels, with far higher levels in rMVA-CD40L transduced cells (FIG. 3B). TNF-α and IL-12p70, however, were strongly expressed exclusively by rMVA-CD40L-transduced BMDCs. Thus, the addition of CD40L into rMVA did not change OVA-antigen expression but improved its immunogenicity in vitro.

Example 4

Figure 4:
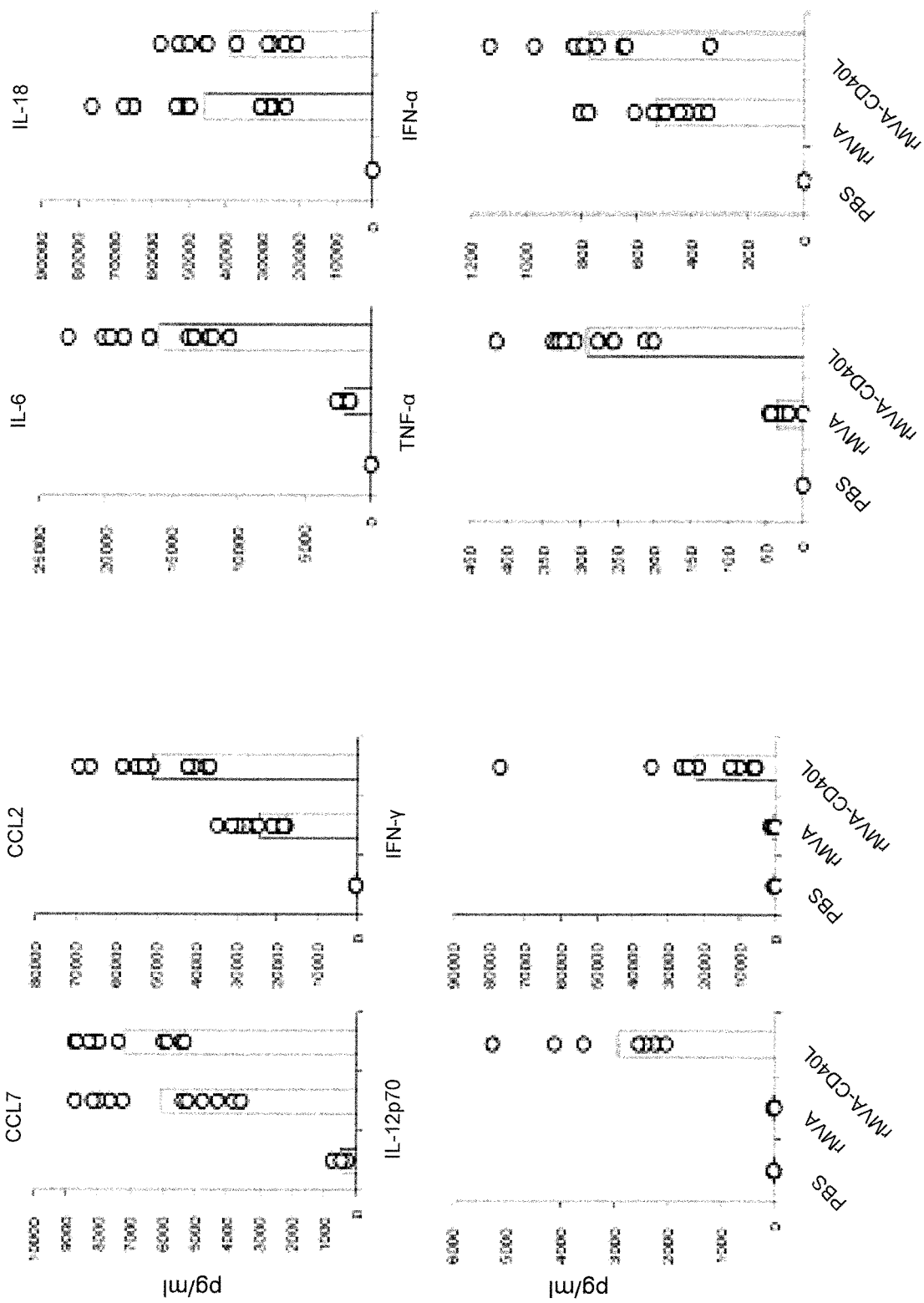
FIG. 4 shows enhanced systemic cytokine levels after injection of rMVA-CD40L. C57BL/6 mice were treated with PBS, rMVA or rMVA-CD40L. 6 hours after injection serum cytokine levels were determined by a cytometric bead assay. Note that IL-12p70 was only detectable after rMVA-CD40L injection. IFN-$\gamma$ levels were low to undetectable after rMVA immunization. Results are compiled from three independent experiments. Circles denote individual mice and bars the mean of all mice per group.
Figure 5A:
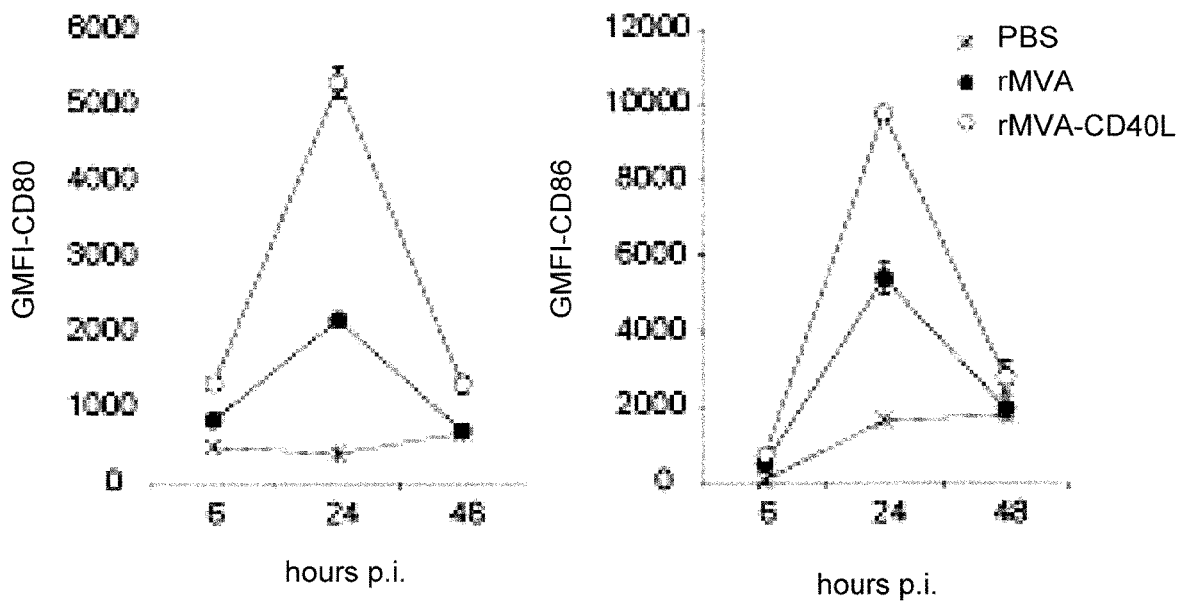
FIG. 5 shows enhanced DC activation in vivo after rMVA-CD40L immunization. C57BL/6 mice were treated with PBS, rMVA or rMVA-CD40L. (A) 6, 24 and 48 hours after injection splenic DCs were analyzed for expression of the activation markers CD80 and CD86. Similar to in vitro transduced DCs (see FIG. 3), splenic DCs were more strongly activated by rMVA-CD40L. The peak of activation was at 24 hours post immunization. (B) In order to test whether the enhanced immunogenicity of rMVA-CD40L is dependent on the interaction of CD40 and virally encoded CD40L, we immunized CD40$^{+/+}$ C57BL/6 mice with rMVA or rMVA-CD40L and CD40 mice with rMVA-CD40L. Serum concentration of IL-12p70 was determined 6 hours after injection and CD86 expression was analyzed on splenic DCs after 24 hours. Shown is the mean±SEM of three mice per group.
Figure 5B:
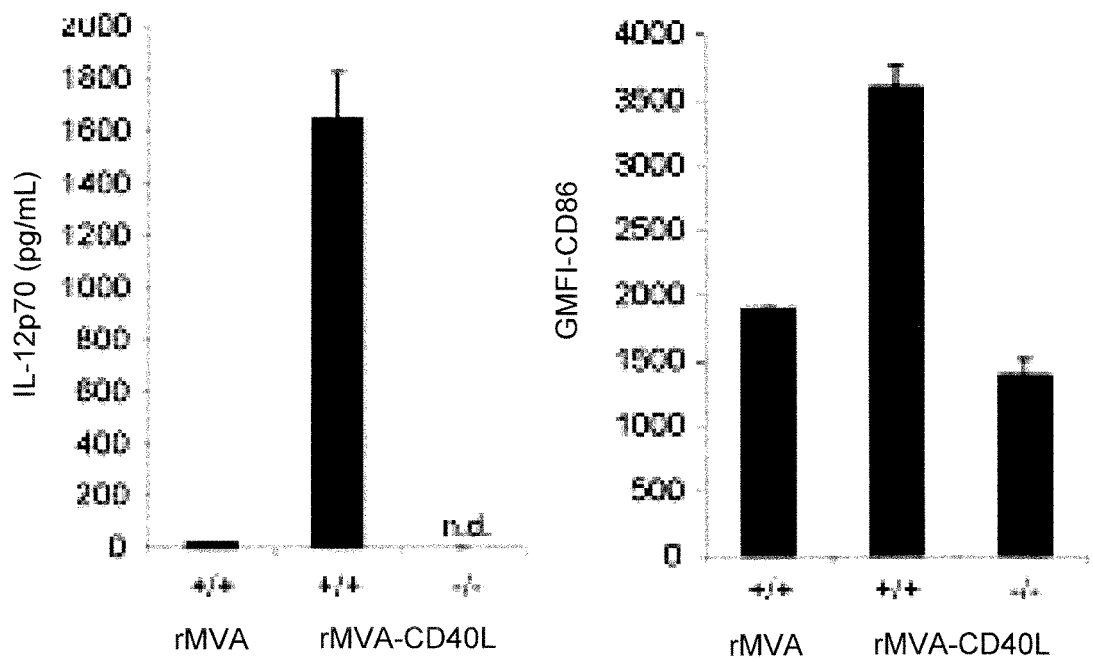

Heightened DC Activation and Innate Cytokine Production In Vivo After Immunization with rMVA-CD40L To gain insight into the in vivo immunogenicity of the two vaccine vectors, mice were intravenously inoculated with rMVA and rMVA-CD40L. 6 hours after injection, mice were bled for serum cytokine analyses using standard methods. While there were no differences in expression of CCL7 and IL-18, rMVA-CD40L induced significantly higher levels of CCL2, IL-6, TNF-α, IFN-α, IL-12p70 and IFN-γ, with the latter two not detectable in serum of rMVA-immunized mice (FIG. 4). Of note, IL-12p70 levels after rMVA-CD40L immunization were ~10-fold higher than after injection of the prototypical IL-12 inducer CpG1668 (2936±1046 vs. 292±31). Similar to the in vitro analyses, DC activation in vivo was also monitored. CD80 and CD86 expression by conventional DCs ("cDCs") was increased after rMVA immunization with the peak at 24 hours (FIG. 5A). Both CD80 and CD86 were expressed at a significantly higher level after injection of rMVA-CD40L. In order to confirm that the enhanced immunogenicity of rMVA-CD40L was due to the insertion of CD40L, wild-type (wt) C57BL/6 mice were immunized either with rMVA or rMVA-CD40L, CD40 mice were immunized with rMVA-CD40L, and CD86 expression by cDCs was measured again after 24 hours. While wt DCs expressed higher levels of CD86 following rMVA-CD40L immunization compared to rMVA immunization, there was no enhanced expression by DCs isolated from CD40–/– mice (FIG. 5B). Similarly, the cytokine expression pattern after 6 hours was comparable between rMVA-immunized wt mice and rMVA-CD40L-immunized knock-out ("KO") mice (FIG. 5B). Taken together, these data confirmed the enhanced immunogenicity of rMVA-CD40L and proved that the observed effect was strictly dependent on interaction between CD40 and virally-encoded CD40L.

Figure 6:
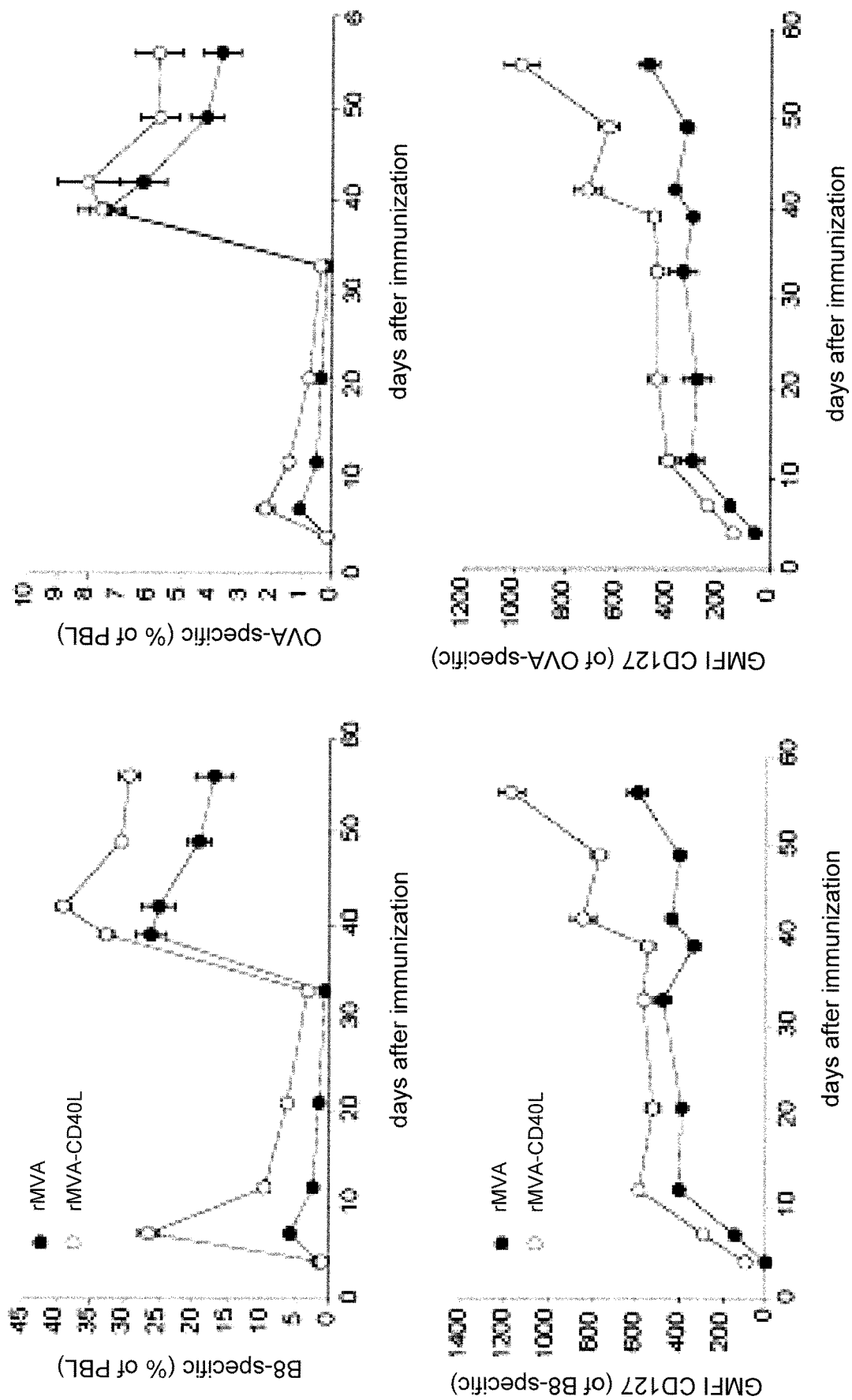
FIG. 6 shows increased CD8+ T-cell response after rMVA-CD40L immunization. C57BL/6 mice were immunized with rMVA and rMVA-CD40L on day 0 and 35. The primary and secondary B8- and OVA-specific CD8+ T-cell response was quantified by dextramer staining of PBL at the indicated time points as shown in FIG. 1A. (A) The kinetic analysis shows the mean percentage±SEM of CD8+ dextramer$^+$ T-cells among PBL. (B) B8- and OVA-specific CD8+ T-cells were also analyzed flow cytometrically for surface expression of CD127. Shown is the mean±SEM GMFI. Data represents five mice per group and two independent experiments.

Example 5 rMVA-CD40L Immunization Induced High Numbers of Multifunctional CD8+ T-Cells and Faster Memory Differentiation The strong up-regulation of co-stimulatory molecules on DCs and the induction of high levels of T-cell instructing cytokines (e.g., IL-12p70) following rMVA-CD40L immunization suggested that this vector might induce superior CTL responses as well. Therefore, after assessing innate immunity in vitro and in vivo, the analyses were extended to examine T-cell responses after rMVA-CD40L immunization. To this end, C57BL/6 mice were injected with rMVA or rMVA-CD40L and the frequency of B8- and OVA-specific CD8+ T-cells in blood over time was measured. In both groups, specific CD8+ T-cells became detectable on day 4 and peaked on day 7 after the first immunization (FIGS. 6A and B). In line with the pilot experiment (see FIG. 1), the frequency at the peak of the primary response of B8- and OVA-specific CTLs was ~5 and ~2-fold higher, respectively, after rMVA-CD40L immunization.

As expected, both T-cell populations increased substantially after the boost on day 35 and once again antigen-specific CD8+ T-cell frequencies were higher in rMVA-CD40L-immunized mice. Notably, a single immunization with rMVA-CD40L resulted in the same frequency of B8-specific T-cells (~26% of PBL) as two immunizations with rMVA. In order gain insight into the effect of additional CD40L stimulation on memory differentiation, the expression of the IL-7 receptor a chain (IL-7Rα, CD127) on antigen-specific CD8+ T-cells was further analyzed. Surface expression of CD127 on activated CD8+ T-cells is used as a marker to distinguish between effector and memory T-cells [K. M. Huster et al., "Selective expression of IL-7 receptor on memory T-cells identifies early CD40L-dependent generation of distinct CD8+ memory T-cell subsets," Proc. Nat'l Acad. Sci. USA 101(15):5610-5615 (2004); S. M. Kaech et al., "Selective expression of the interleukin 7 receptor identifies effector CD8+ T-cells that give rise to long-lived memory cells," Nature Immunol. 4(12):1191-1198 (2003)] and $CD127^{high}$ memory CD8+ T-cells have been correlated with better protection against bacterial challenge [Kaech et al., (2003)].

Interestingly, at all time points analyzed B8- and OVA-specific CD8+ T-cells in rMVA-CD40L-immunized mice had higher geometric mean fluorescence intensities ("GMFI") of CD127 (FIGS. 6C and D). The higher GMFI was a result of two things: (1) more $CD127^{high}$ cells; and (2) higher CD127 expression on a per cell basis. The difference between the two groups became most prominent after the second immunization. Thus, rMVA-CD40L immunization not only leads to enhanced CTL responses but also to faster memory differentiation.

Figure 7A:
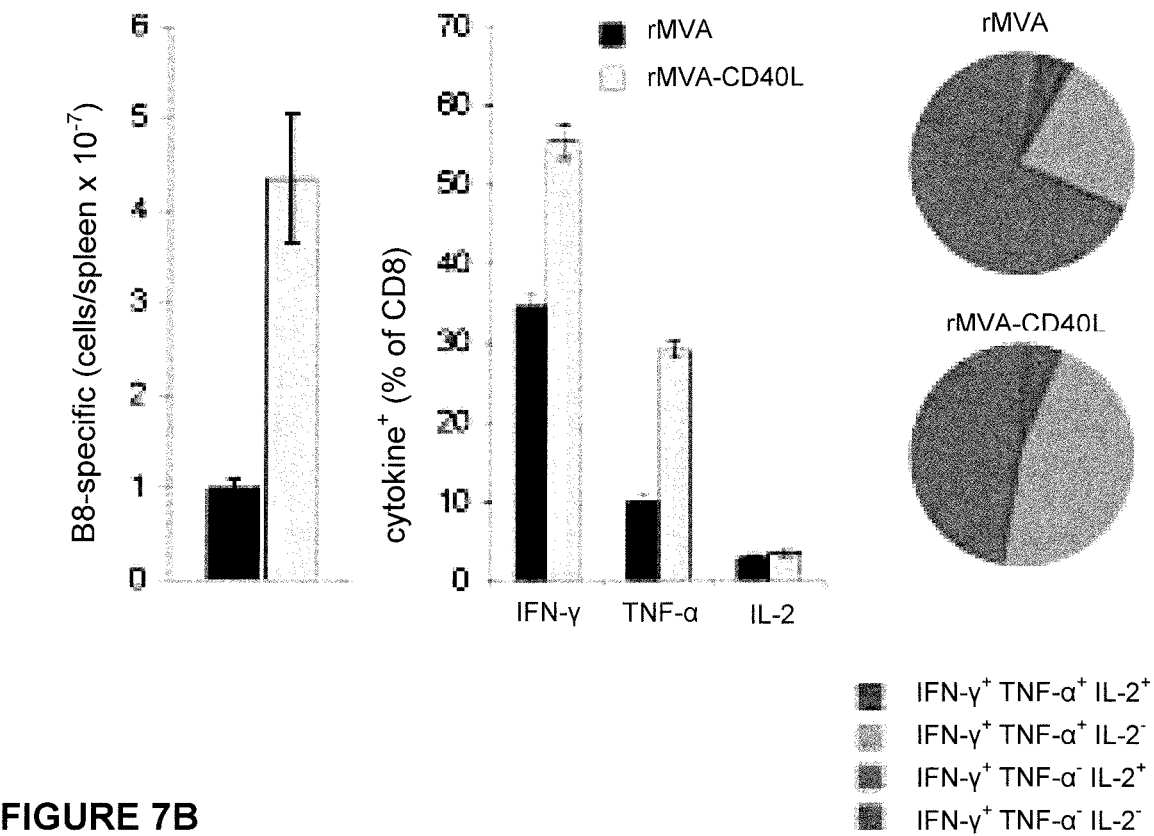
FIG. 7 shows quantitative and qualitative improvement of primary CD8+ T-cell responses after immunization with rMVA-CD40L. C57BL/6 mice were immunized with rMVA or rMVA-CD40L. B8-specific (A) and OVA-specific (B) CD8+ T-cell numbers in the spleen were determined by MHC I dextramer staining on day 7 after immunization (left panel). IFN-γ, TNF-α and IL-2 production was analyzed by intracellular cytokine staining after standard 6 hour in vitro re-stimulation with $B8_{20-27}$ and $OVA_{257-264}$ peptides (middle panel). Pie charts denote the fraction of IFN-γ$^+$ cells expressing IFN-γ alone (violet), IFN-γ and TNF-α (green), IFN-γ and IL-2 (blue) and IFN-γ, TNF-α and IL-2 (red). Note the increased percentage of IFN-γ/TNF-α double producing cells in rMVA-CD40L immunized mice (green area). Thus, in comparison to rMVA, rMVA-CD40L immunization leads to functionally improved primary effector CD8+ T-cells. Data represent five mice per group and two independent experiments.
Figure 7B:
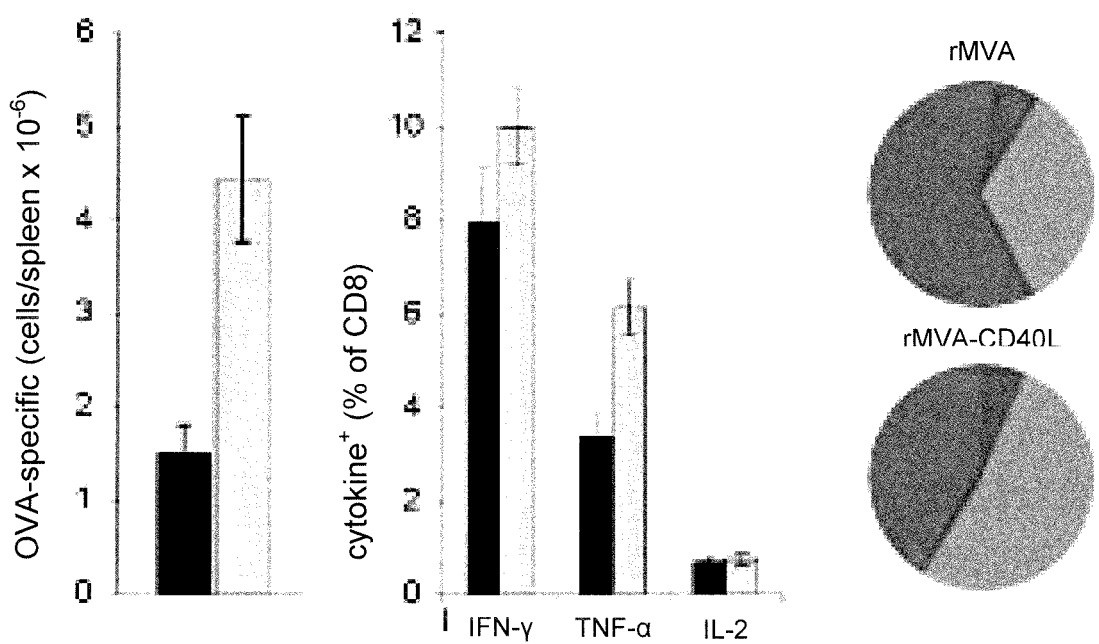
Figure 8A:
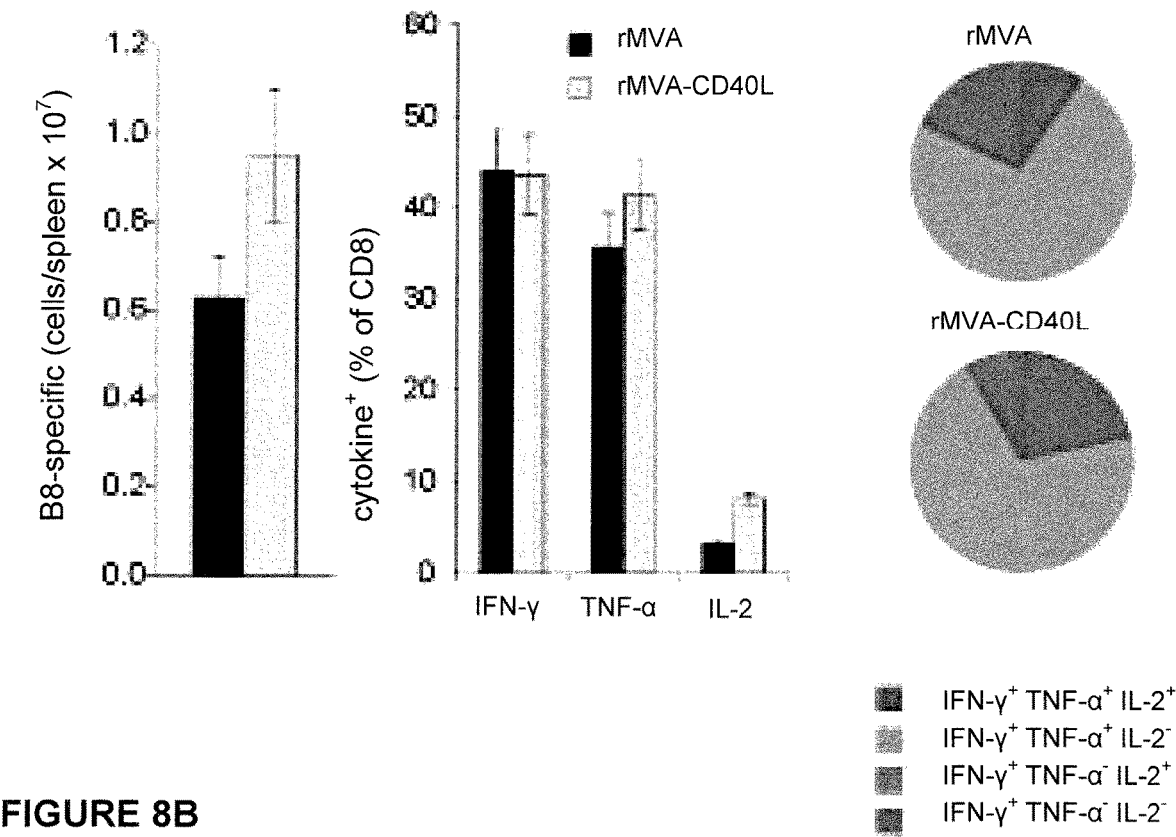
FIG. 8 shows the qualitative improvement of memory CD8+ T-cell responses after immunization with rMVA-CD40L. C57BL/6 mice were immunized on day 0 and 35 with rMVA or rMVA-CD40L. B8-specific (A) and OVA-specific (B) specific CD8+ T-cell numbers in the spleen were determined by MHC I dextramer staining on day 104 (left panel). IFN-γ, TNF-α and IL-2 production were analyzed by intracellular cytokine staining after standard 6 hour in vitro restimulation with $B8_{20-27}$ and $OVA_{257-264}$ peptides (middle panel). Pie charts denote the fraction of IFN-γ$^+$ cells expressing IFN-γ alone (violet), IFN-γ and TNF-α (green), IFN-γ and IL-2 (blue) and IFN-γ, TNF-α and IL-2 (red). Note the increased percentage of IFN-γ/TNF-α/IL-2 triple producer cells in rMVA-CD40L immunized mice (red area). Thus, in comparison to rMVA, rMVA-CD40L immunization leads to functionally improved memory CD8+ T-cells. Data represent five mice per group and two independent experiments.
Figure 8B:
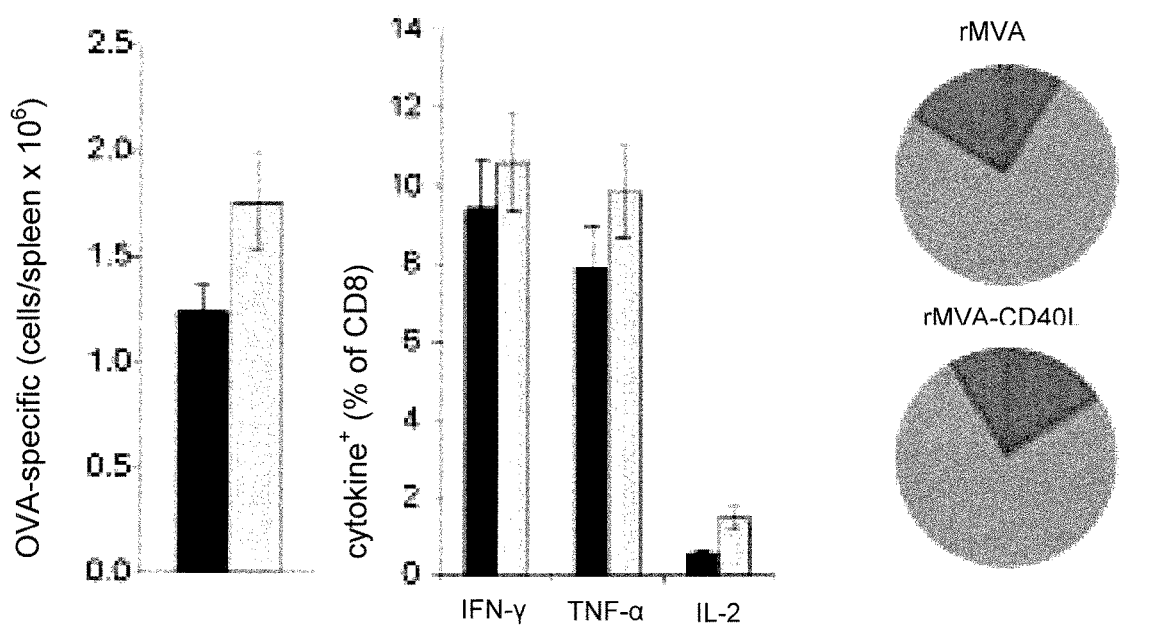

T-cell mediated protection is the result of increased numbers of antigen-specific CD8+ T-cells that are poised to rapidly secrete cytotoxic molecules (e.g., perforin, granzyme B) and cytokines (e.g., IFN-γ, TNF-α). Therefore, after having assessed increased frequencies after rMVA-CD40L immunization, the absolute number and functionality of effector and memory B8- and OVA-specific CD8+ T-cells in the spleen were also analyzed. B8- and OVA-specific CD8+ T-cells were enumerated by MHC class I dextramer staining and intracellular cytokine staining (both using standard methods) at day 7 after one immunization and at day 104 after two immunizations. Increased frequencies in the blood after rMVA-CD40L immunization translated into higher absolute numbers of B8- and OVA-specific CD8+ T-cells in the spleen at day 7 (FIGS. 7A and B, left panel). More IFN-γ and TNF-α producing effector CD8+ T-cells were also detected for both antigens (FIGS. 7A and B, middle panel). A higher functional capacity after rMVA-CD40L immunization was revealed by relatively more IFN-γ+/TNF-α+ cells (FIGS. 7A and B, right panel). At this time point, there was no difference in IL-2 production between the two groups (FIGS. 7A and B, middle panel). Analysis of memory T-cells at day 104 (=day 69 after the 2$^{nd}$ immunization) revealed only marginal differences in absolute numbers of B8- and OVA-specific CD8+ T-cells between rMVA and rMVA-CD40L-immunized mice (FIGS. 8A and B, left panel). Also, the frequencies of IFN-γ and TNF-α producing memory cells were similar (FIGS. 8A and B, middle panel). In contrast to effector cells, however, more rMVA-CD40L-induced memory CD8+ T-cells produced IL-2 upon re-stimulation with B8 and OVA peptides (FIGS. 8A and B, middle panel). Importantly, mice that were immunized with rMVA-CD40L had ~2-fold more triple cytokine positive (IFN-γ, TNF-α, IL-2) antigen-specific CD8+ T-cells (FIGS. 8A and B, right panel).

Figure 9:
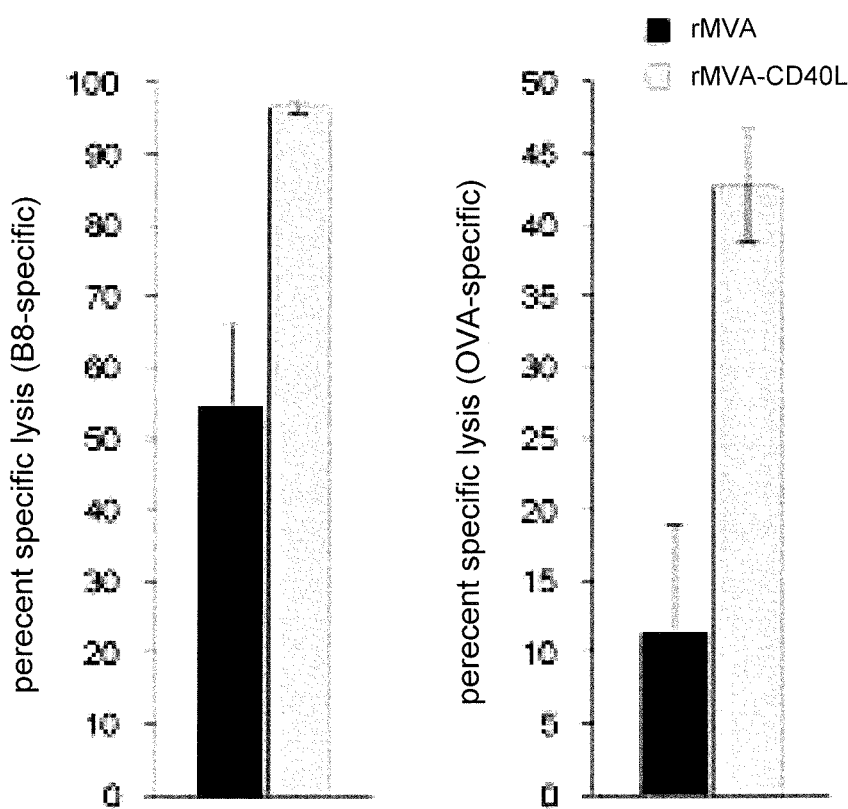
FIG. 9 shows heightened CTL activity in rMVA-CD40L immunized mice. In order to characterize the lytic activity of B8- and OVA CD8+ T-cells, an in vivo CTL assay was performed on day 56 after immunization. Unpulsed (CFSE$^{low}$), $B^8{}_{20-27}$-peptide pulsed (CFSE$^{high}$) and $OVA_{257\text{-}264}$-peptide pulsed (eFluor670$^{high}$) splenic target cells were injected into rMVA- and rMVA-CD40L-immunized mice. 4 hours post-transfer, the ratio of unpulsed and peptide-pulsed target cells was determined and the percent specific lysis calculated. Values represent mean±SEM specific lysis of target cells of four mice per group and two independent experiments.

In order to directly determine the cytolytic activity, an in vivo CTL assay was performed at day 56 after a single immunization. The killing activity was analyzed 4 hours after target cell transfer and revealed 54 compared to 97 percent specific lysis ("PSL") of B8$_{20-27}$ loaded target cells and 11 compared to 43 PSL of OVA$_{257-264}$ loaded target cells for rMVA- and rMVA-CD40L-immunized mice, respectively (FIG. 9). Those results demonstrated that immunization with rMVA-CD40L induced more multifunctional effector and memory CD8+ T-cells with higher cytolytic activity than immunization with rMVA. Since multifunctional T-cells have been correlated with better protection against parasites, bacteria and viruses [M. R. Betts et al., "HIV non-progressors preferentially maintain highly functional HIV-specific CD8+ T-cells," Blood 107(12):4781-4789 (2006); N. E. Beveridge et al., "Immunization with BCG and recombinant MVA85A induces long-lasting, polyfunctional *Mycobacterium tuberculosis*-specific CD4+ memory T-lymphocyte populations," Eur. J. Immunol. 37(11):3089-3100 (2007); P. A. Darrah et al., "Multifunctional T$_H$1 cells define a correlate of vaccine-mediated protection against *Leishmania major*," Nature Med. 13(7): 843-850 (2007); and M. L. Precopio et al., "Immunization with vaccinia virus induces polyfunctional and phenotypically distinctive CD8(+) T-cell responses," J. Exp. Med. 204(6):1405-1416 (2007)], these data suggest that this vaccine vector might induce superior protection.

Example 6

Figure 10A:
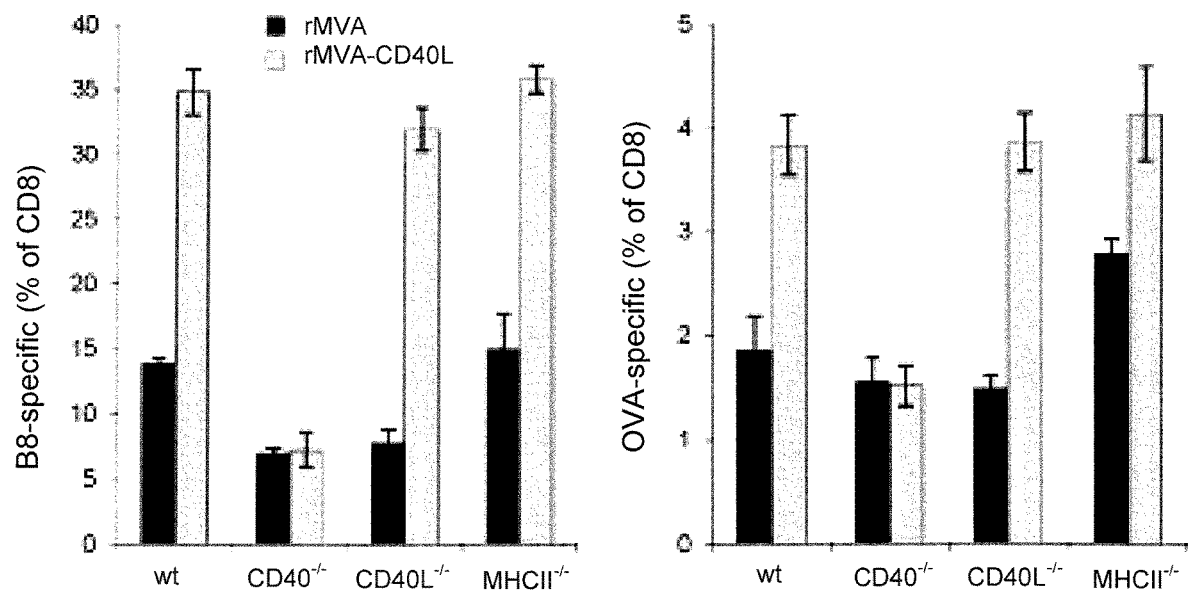
FIG. 10 shows that endogenous CD40 is essential for enhanced CD8+ T-cell response after rMVA-CD40L immunization. (A) C57BL/6 wt, CD40$^{-/-}$, CD40L$^{-/-}$ and MHC II$^{-/-}$ mice were immunized with rMVA and rMVA-CD40L. Seven days later splenic lymphocytes were analyzed flow cytometrically for the presence of B8-specific and OVA-specific CD8+ T-cells. Bars represent the mean±SEM percentage of B8- and OVA-specific CD8+ T-cells of three mice per group. Note that the frequencies in CD40$^{-/-}$ mice were equal after rMVA and rMVA-CD40L immunization, demonstrating an essential role of CD40 for the costimulatory function of virally encoded CD40L. (B) C57BL/6 mice were immunized with active or UV/psoralen-inactivated rMVA and rMVA-CD40L. Serum concentration of IL-12p70 was determined 6 hours after injection and CD86 expression was analyzed on splenic DCs after 24 hours. Shown is the mean±SEM of five to six mice per group and two independent experiments.
Figure 10B:
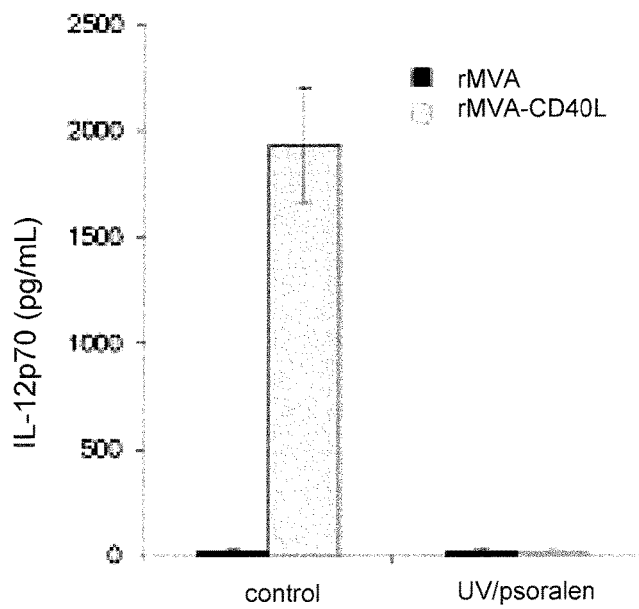

Increased Immunogenicity of rMVA-CD40L was Independent of CD4+ T-Cells but Dependent on CD40 Expression in the Host After having demonstrated clearly superior DC activation and CD8+ T-cell responses after rMVA-CD40L immunization, additional studies designed to elucidate the mechanism of action of this vaccine vector were performed. For this purpose wt, CD40, CD40L and MHC-II$^{-/-}$ mice were initially immunized with rMVA or rMVA-CD40L and B8- and OVA-specific CD8+ T-cell responses were determined on day 7 in the spleen. As expected from the results shown in FIG. 5C, the heightened T-cell response after rMVA-CD40L immunization was strictly dependent on CD40 expression in the host (FIG. 10A). Interestingly, neither CD40L nor CD4+ T-cells were required for the enhancement. Because Bereta et al. suggested that CD40L might be present in recombinant vaccinia virus virions [M. Bereta et al., (2004)], it was possible this might also be true for the rMVA-CD40L vector. To this end, rMVA-CD40L was inactivated by psoralen/UV treatment and serum cytokine levels were measured 6 hours after immunization by standard methods. In contrast to active rMVA-CD40L, no IL-12p70 was detected in the serum of mice treated with inactivated virus (FIG. 10B). These data suggest that expression of virally encoded CD40L (vCD40L) is necessary for the increased immunogenicity of rMVA-CD40L.

Figure 11:
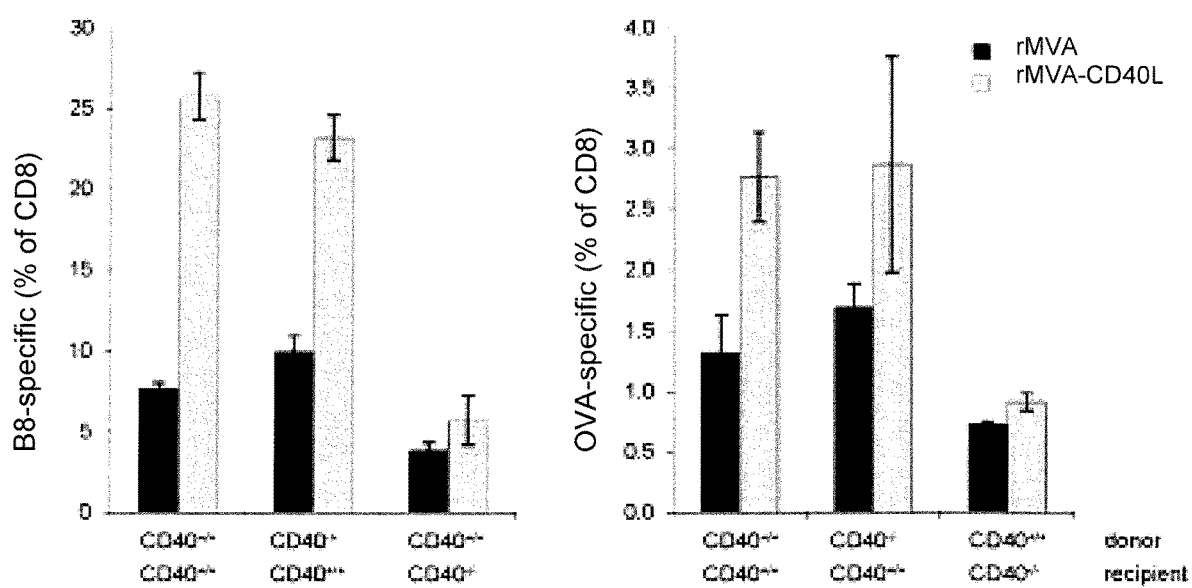
FIG. 11 shows that CD40 expression on transduced DCs is dispensable for heightened immunogenicity of rMVA-CD40L. In vitro-generated FLDCs from CD40$^{+/+}$ wt and CD40$^{-/-}$ mice were transduced with rMVA or rMVA-CD40L (MOI=2.5) and injected into CD40$^{+/+}$ wt and CD40$^{-/-}$ mice. Seven days later the frequencies of splenic B8-specific and OVA-specific CD8+ T-cells were determined by dextramer staining. Note that rMVA-CD40L transduced DCs can be CD40$^{-/-}$ to show enhanced CD8+ T-cell responses, but not the DC recipient. Values represent the mean±SEM percentage of B8-specific and OVA-specific CD8+ T-cells of three mice per group.

The classical view has been that CD40L is mainly expressed by CD4+ T-helper cells ("CD4+ T$_H$-cells") and CD40 by professional antigen presenting cells ("pAPC"). In recent years it has become clear, however, that both molecules can be expressed on many cells, facilitating a wide range of interactions [R. Elgueta et al., "Molecular mechanism and function of CD40/CD40L engagement in the immune system," Immunol. Rev. 229(1):152-172 (2009)]. MVA is known to transduce DCs in vivo [H. Lauterbach, unpublished observation and L. Liu et al., "Dendritic cells are preferentially targeted among hematolymphocytes by Modified Vaccinia Virus Ankara and play a key role in the induction of virus-specific T-cell responses in vivo," BMC Immunol. 9:15 (2008)]. In order to find out whether CD40 needs to be expressed on transduced DCs theoretically enabling short circuit activation, or if expression of rMVA-encoded CD40L allows activation of CD40$^+$ non-transduced cells in trans, a DC immunization protocol with restricted CD40 expression was used (FIG. 11). As shown in FIG. 11, immunization of wt mice with rMVA- and rMVA-CD40L-transduced wt DCs yielded similar CD8+ T-cell responses as direct immunization (compare FIG. 11 to FIG. 10). The same frequencies of B8- and OVA-specific CD8+ T-cells were induced upon vaccination with transduced CD40 DCs when transferred into wt recipients. When rMVA-CD40L-transduced wt DCs were used to immunize CD40$^{-/-}$ mice, however, the augmentation of the CD8+ T-cell response was almost completely abolished. Therefore, CD40 expression in the host is essential for enhanced CD8+ T-cell responses after rMVA-CD40L immunization and the increased immunogenicity of rMVA-CD40L is dependent on interaction between vCD40L+ DCs and CD40+ host cells. Transduced DCs, however, do not need to express CD40, suggesting signaling in trans occurs between vCD40L and host CD40.

Example 7

Figure 12A:
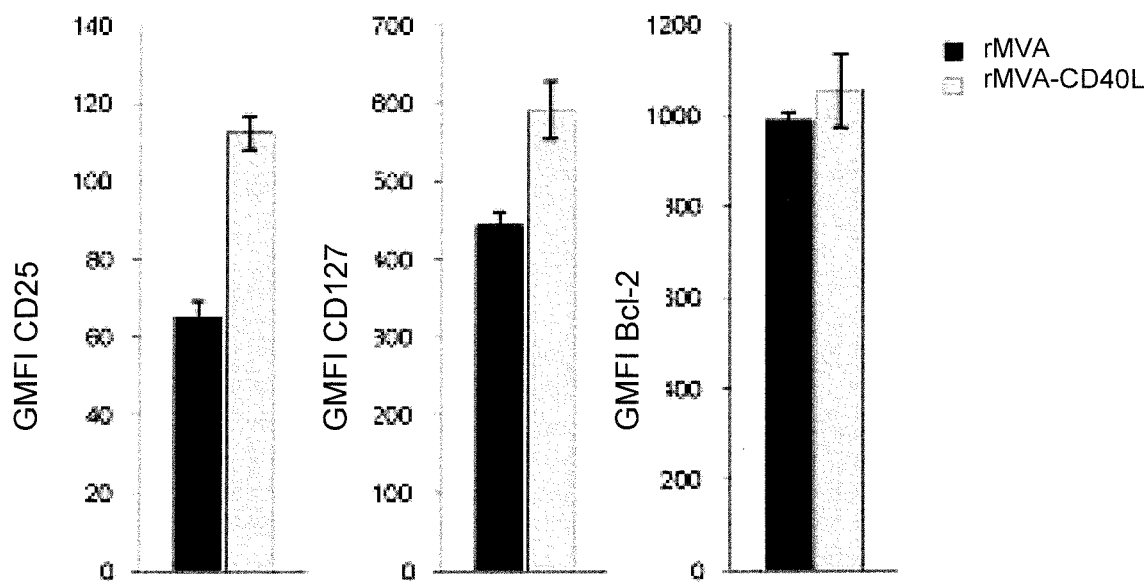
FIG. 12 shows that rMVA-CD40L immunization influences the phenotype and the proliferation rate of CD8+ T-cells. C57BL/6 mice were immunized with rMVA and rMVA-CD40L. Five days later expression of CD25, CD127 and Bcl-2 in B8-specific CD8+ T-cells was analyzed flow cytometrically. (A) Bars represent the mean±SEM GMFI (gated on B8-dextramer$^+$ CD8+ T-cells). In order to measure cell proliferation, mice were treated with the thymidine analog EdU five days later. EdU incorporation into splenic T-cells was determined flow cytometrically after one hour. (B) The percentage and GMFI of EdU$^+$ CD4+, CD8+ and B8-specific T-cells are shown as the mean±SEM. (C) The relative frequencies of CD127$^+$ KLRG-1$^-$, CD127$^+$ KLRG-1$^+$, CD127 KLRG-1$^+$ and CD127$^-$ KLRG-1$^-$ cells among all splenic B8-specific CD8+ T-cells on day 7 after immunization. Data represent five mice per group and at least two independent experiments.
Figure 12B:
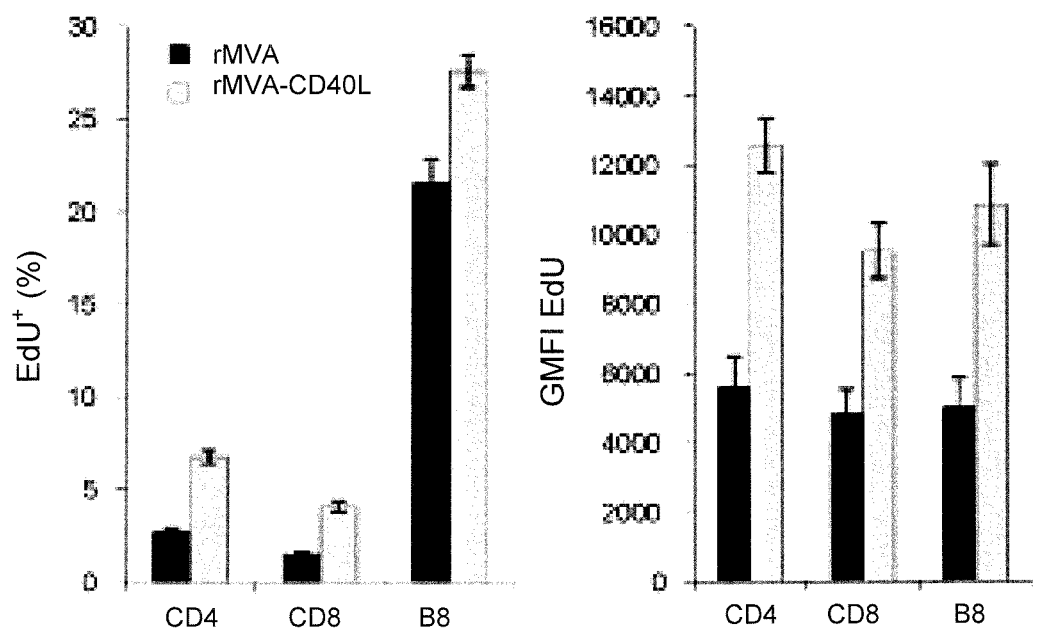

Higher Expression of IL-2Rα and IL-7Rα on T-Cells and Faster Proliferation After rMVA-CD40L Immunization Next, the CD8+ T-cells were investigated in more detail. Enhanced CD8+ T-cell numbers can be the result of faster proliferation, less apoptosis or a combination of both. Proliferation and survival in turn are regulated, at least in part, by cytokines of the IL-2 family (IL-2, IL-4, IL-7, IL-9, IL-15 and IL-21)[ M. Benczik and S. L. Gaffen, "The interleukin (IL)-2 family cytokines: survival and proliferation signaling pathways in T-lymphocytes," Immunol. Invest. 33(2):109-142 (2004)]. Especially, enhanced signaling via the IL-2 receptor leads to stronger expansion of antigen-stimulated CD8+ T-cells [L. E. Cheng et al., "Enhanced signaling through the IL-2 receptor in CD8+ T-cells regulated by antigen recognition results in preferential proliferation and expansion of responding CD8+ T-cells rather than promotion of cell death," Proc. Nat'l Acad. Sci. USA 99(5):3001-3006 (2002)]. Therefore, expression of CD25 (IL-2Rα), CD127 (IL-7Rα) and the anti-apoptotic molecule Bcl-2 on B8-specific CD8+ T-cell were initially measured five days after immunization with rMVA or rMVA-CD40L. B8-specific CD8+ T-cells in rMVA-CD40L-immunized animals displayed higher expression of CD25 and CD127 but not of Bcl-2 than in rMVA-immunized mice (FIG. 12). In order to measure cell proliferation, the thymidine analog EdU was administered intravenously ("i.v.") on day 5 after immunization and excised the spleens one hour later. As shown in FIG. 12, EdU was incorporated into the DNA of CD4+ and CD8+ T-cells. The percentage of EdU+ CD4+ and CD8+ T-cells was ~2.5times higher in rMVA-CD40L- than in rMVA-immunized mice. Significantly, more B8-specific CD8+ T-cells had taken up EdU within one hour (27.6%±0.9 vs. 21.6%±1.3; p≤0.005). Furthermore, the amount of incorporated EdU was determined on a per cell basis by measuring the GMFI of EdU+ cells. All investigated T-cell populations (CD4+, CD8+ and B8-specific CD8+) in rMVA-CD40L-immunized mice showed drastically higher GMFIs of EdU, indicating a faster cell cycle. Taken together, both higher expression of CD25 and CD127 and more and faster proliferating T-cells were observed after immunization with rMVA-CD40L.

Figure 12C:
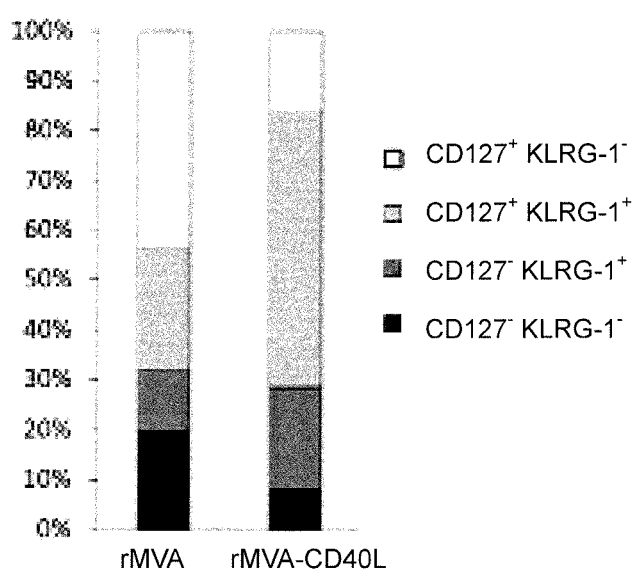

Because IL-12 is known to influence the memory potential of CD8+ T-cells [N. S. Joshi et al., "Inflammation directs memory precursor and short-lived effector CD8(+) T-cell fates via the graded expression of T-bet transcription factor," *Immunity* 27(2):281-295 (2007)], the memory-related phenotype of B8 CD8+ T-cells was analyzed. As shown in FIG. 12C, 12.2±1.6% of B8-specific CD8+ T-cells had the phenotype of short-lived effector cells ("SLECs", which are $CD127^-/KLRG-1^+$) seven days after rMVA immunization while 20.5±1.1% displayed this phenotype after rMVA-CD40L immunization. In the latter group, most cells were double positive for CD127 and KLRG-1 (55±3%). The percentage of memory precursor effector cells ("MPECs", which are $CD127^+/KLRG-1^-$) and early effector cells ("EECs", which are $CD127^-/KLRG-1^-$) was higher in rMVA-immunized mice (43.8±3.4% and 19.7±2.3%, respectively). Thus, integration of CD40L into rMVA clearly influences the memory-related phenotype of CD8+ T-cells.

Example 8

Figure 13:
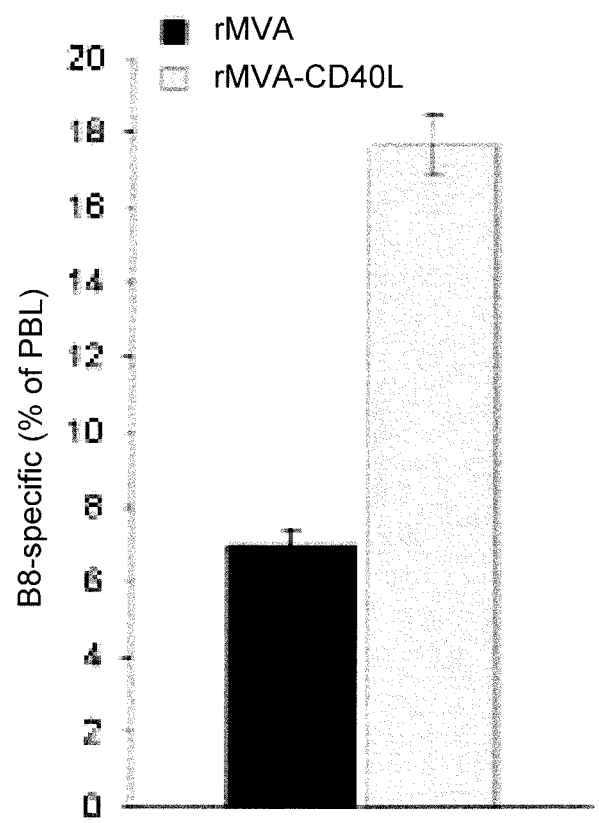
FIG. 13 shows that B-cell deficient JHT mice mount similar CD8+ T-cell responses as C57BL/6 wt mice. In order to confirm that B-cell deficient JHT mice used for challenge studies mount similar responses as C57BL/6 wt mice, JHT mice were immunized with rMVA and rMVA-CD40L. Seven days later the frequency of B8-specific CD8+ T-cells in the blood was determined by dextramer staining. Note that the percentage of B8-dextramer CD8+ T-cells after immunization is comparable between C57BL/6 wt mice (see FIG. 6) and JHT mice. Data represent five mice per group and two independent experiments.

Immunization with rMVA-CD40L Conferred Sterile Protection Independently of Antibodies In light of the astonishingly strong CD8+ T-cell response after immunization with rMVA-CD40L, it was evaluated whether immunization with this vaccine vector provided better protection in an infection model. Because prophylactic immunization of wt mice with MVA already provides full protection against vaccinia virus or ectromelia virus ("ECTV") challenge via antibodies [I. M. Belyakov et al., "Shared modes of protection against poxvirus infection by attenuated and conventional smallpox vaccine viruses," *Proc. Nat'l Acad. Sci. USA* 100(16):9458-9463 (2003)], a T-cell-dependent and antibody-independent challenge model was established. To this end, B-cell deficient JHT mice were immunized with rMVA or rMVA-CD40L and then challenged approximately two months later with a lethal dose of ECTV. B8-specific CD8+ T-cell responses were confirmed to be similar in JHT and wt mice (FIG. 13). While five out of five mice immunized with rMVA developed severe symptoms of ECTV infection, including necrotic tails, swollen and necrotic paws, and skin lesions, and either died or had to be euthanized, none of the rMVA-CD40L-immunized mice developed any infection symptoms during an observation period of 55 days. These data suggest that the heightened and qualitatively improved CD8+ T-cell response after rMVA-CD40L immunization leads to sterile protection against a lethal virus challenge even in the complete absence of antibodies.

Example 9

MVA-CD40L Increases CTL Responses if Used During Boost

Figure 14:
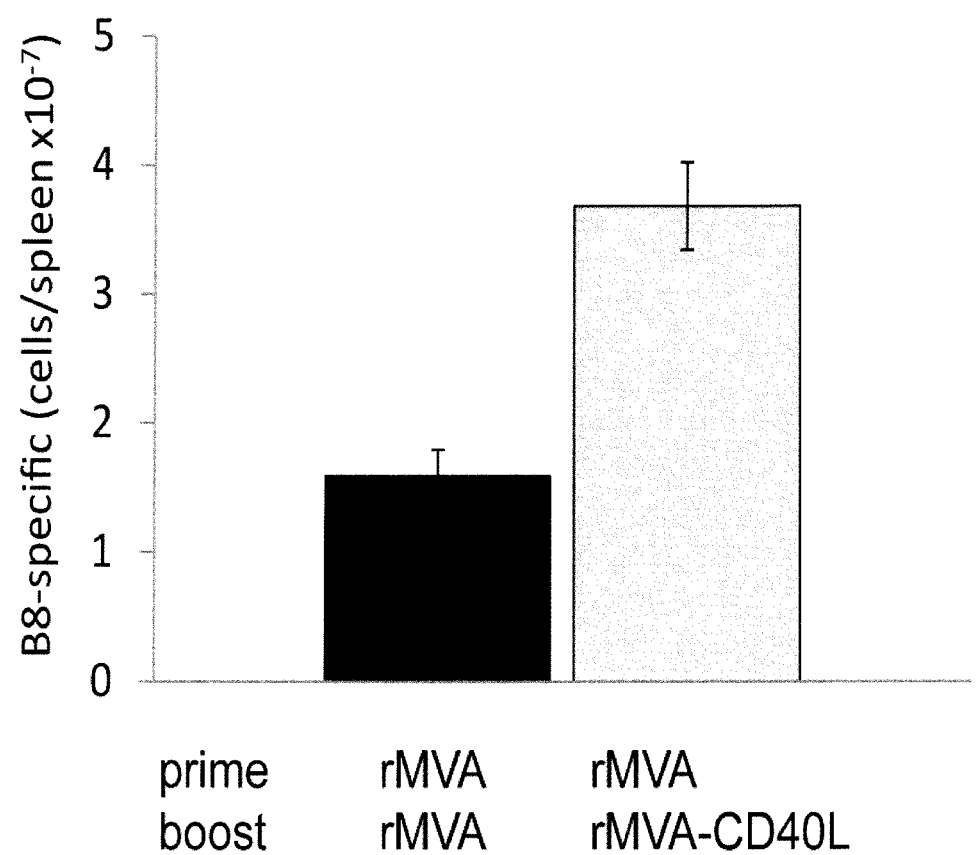
FIG. 14 shows that MVA-CD40L increases CTL responses if used during boost.

To analyse if MVA-CD40L is able to increase cytotoxic T-cell (CTL) responses if solely used during the boost regime, we immunized mice with MVA and boosted after 4 weeks with either MVA only or with MVA-CD40L. Spleen cells were analysed on day 35 after the primary (day 7 after the boost) immunization with pentamers specific for the orthopoxvirus-specific epitope B8. MVA used for prime and boost showed the typical numbers of B8-specific CTLs (FIG. 14, left column). Using MVA-CD40L for the boost regime resulted in further increased numbers of specific CTLs (FIG. 14, right column). Thus, the incorporation of CD40L into MVA enhances existing CTL responses more strongly than the use of MVA alone.

Example 10

MVA-CD40L Induces IL-12p70 in Mouse and Human Dendritic Cells

Figure 15A:
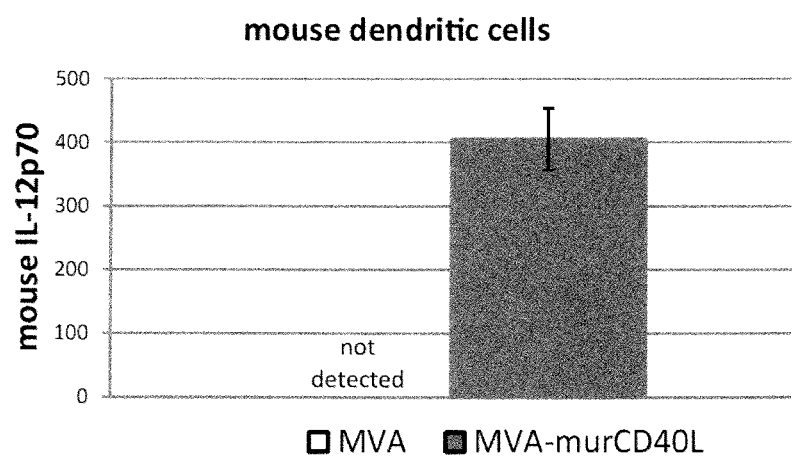
FIG. 15 shows that mouse and human CD40L sequences incorporated into MVA are both able to activate corresponding species- and CD40L-specific immune responses.
Figure 15B:
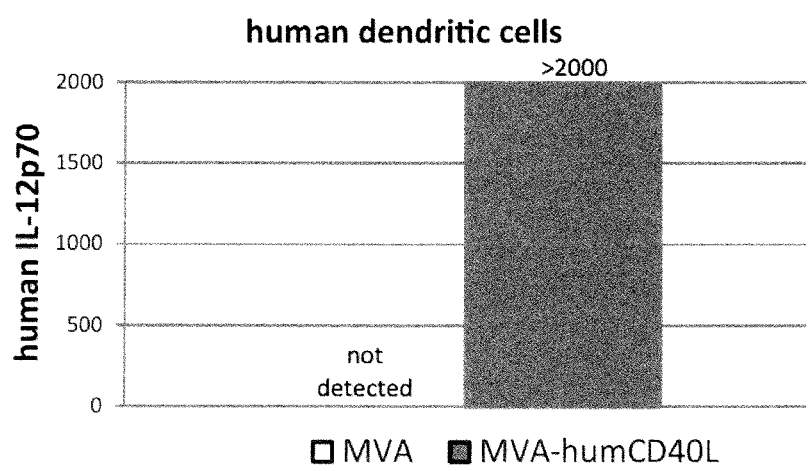

To gain insight into the stimulatory activity of MVA-CD40L we transduced mouse or human dendritic cells with MVA-CD40L of mouse or human origin respectively. Mouse and human dendritic cells were generated and stimulated and IL-12p70 levels in the cell cultures supernatants were determined after 18 hours of culture as described elsewhere (Lauterbach et al., *J. Exp. Med.* 207(12):2703-2717 (2010); Traidl-Hoffmann et al., *J. Exp. Med.* 201(4): 627-636 (2005)). IL-12p70 induces interferon-γ ("IFN-γ") production by natural killer cells, T-cells, dendritic cells, and macrophages. It also promotes differentiation of naïve CD4+ T-cells into $T_H1$ cells that produce IFN-γ and aid in cell-mediated immune responses. See, e.g., Watford et al., *Cytokine & Growth Factor Rev.* 14:361-368 (2003). Whereas empty MVA did not induce any detectable IL-12p70 levels in mouse dendritic cells, recombinant MVA harbouring the murine CD40L induced robust levels of IL-12p70 (FIG. 15A). Similarly, recombinant MVA with human CD40L induced IL-12p70 in human dendritic cells, whereas MVA without CD40L was unable to induce detectable IL-12p70 amounts (FIG. 15B). Thus, mouse and human CD40L sequences incorporated into MVA are both able to activate corresponding species and CD40L-specific immune responses.

Sequences (amino acid sequence of mouse CD40L (Accession No. NM_011616.2):

SEQ ID NO: 1

MIETYSQPSPRSVATGLPASMKIFMYLLTVFLITQMIGSVLFAVYLHRRLDKVEEEVNLHE

DFVFIKKLKRCNKGEGSLSLLNCEEMRRQFEDLVKDITLNKEEKKENSFEMQRGDEDP

QIAAHVVSEANSNAASVLQWAKKGYYTMKSNLVMLENGKQLTVIKREGLYYVYTQVTFC

```
SNREPSSQRPFIVGLWLKPSSGSERILLKAANTHSSSQLCEQQSVHLGGVFELQAGASVFV

NVTEASQVIHRVGFSSFGLLKL
```

(amino acid sequence of human CD40L (Accession No. NM_000074.2)):
SEQ ID NO: 2
```
MIETYNQTSPRSAATGLPISMKIFMYLLTVFLITQMIGSALFAVYLHRRLDKIEDERNLHED

FVFMKTIQRCNTGERSLSLLNCEEIKSQFEGFVKDIMLNKEETKKENSFEMQKGDQNPQ

IAAHVISEASSKTTSVLQWAEKGYYTMSNNLVTLENGKQLTVKRQGLYYIYAQVTFCSNR

EASSQAPFIASLCLKSPGRFERILLRAANTHSSAKPCGQQSIHLGGVFELQPGASVFVNVTD

PSQVSHGTGFTSFGLLKL
```

($B8_{20-27}$-peptide):
SEQ ID NO: 3
TSYKFESV ($OVA_{257-264}$-peptide):
SEQ ID NO: 4
SIINFEKL ($ZEBOV\text{-}GP_{577-584}$-peptide):
SEQ ID NO: 5
TELRTFSI Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A method of enhancing T-cell responses specific for a disease-associated antigen in a human comprising administering intravenously to the human a priming injection of a recombinant modified vaccinia virus Ankara (MVA) that is not capable of reproductive replication in the human keratinocyte cell line HaCat and that comprises:
   (a) a nucleic acid sequence encoding a CD40 ligand (CD40L) and
   (b) a nucleic acid sequence encoding a heterologous disease-associated antigen; wherein the intravenous administration of the recombinant MVA induces increased numbers of cytotoxic T-cells (CTLs) specific for the heterologous disease-associated antigen, and wherein the method further comprises administering to the human one or more boosting injections of the recombinant MVA.

2. The method of claim 1, wherein the intravenous administration of the recombinant MVA induces increased numbers of cytotoxic T-cells (CTLs) specific for the heterologous disease-associated antigen after said priming injection.

3. The method of claim 1, wherein the modified vaccinia virus Ankara (MVA) is MVA-BN or a derivative of MVA-BN.

4. The method of claim 1, wherein the increased T-cell response comprises greater numbers of memory T-cells specific for the heterologous disease-associated antigen.

5. The method of claim 1, wherein the nucleic acid sequence encodes a CD40L having at least 95%, 96%, 97%, 98%, 99%, or 100% amino acid sequence identity to SEQ ID NO:2.

6. The method of claim 1, wherein the nucleic acid sequence encodes a CD40L having the amino acid sequence of SEQ ID NO:2.

7. The method of claim 1, wherein the disease-associated antigen is an infectious disease antigen or a tumor-associated antigen.

8. The method of claim 1, wherein the disease-associated antigen is a tumor-associated antigen.

9. The method of claim 7, wherein the tumor-associated antigen is selected from the group consisting of: 5-α-reductase, α-fetoprotein ("AFP"), AM-1, APC, April, B melanoma antigen gene ("BAGE"), β-catenin, Bcl12, bcr-abl, Brachyury, CA-125, caspase-8 ("CASP-8", also known as "FLICE"), Cathepsins, CD19, CD20, CD21/complement receptor 2 ("CR2"), CD22/BL-CAM, CD23/F$_c$εRII, CD33, CD35/complement receptor 1 ("CR1"), CD44/PGP-1, CD45/leucocyte common antigen ("LCA"), CD46/membrane cofactor protein ("MCP"), CD52/CAMPATH-1, CD55/decay accelerating factor ("DAF"), CD59/protectin, CDC27, CDK4, carcinoembryonic antigen ("CEA"), c-myc, cyclooxygenase-2 ("cox-2"), deleted in colorectal cancer gene ("DCC"), DcR3, E6/E7, CGFR, EMBP, Dna78, farnesyl transferase, fibroblast growth factor-8a ("FGF8a"), fibroblast growth factor-8b ("FGF8b"), FLK-1/KDR, folic acid receptor, G250, G melanoma antigen gene family ("GAGE-family"), gastrin 17, gastrin-releasing hormone, ganglioside 2 ("GD2")/ganglioside 3 ("GD3")/ganglioside-monosialic acid-2 ("GM2"), gonadotropin releasing hormone ("GnRH"), UDP-GlcNAc:$R_1$Man($\alpha$1-6)$R_2$ [GlcNAc to Man ($\alpha$1-6)] $\beta$1,6-N-acetylglucosaminyltransferase V ("GnT V"), GP1, gp100/Pme117, gp-100-in4, gp15, gp75/tyrosine-related protein-1 ("gp75/TRP-1"), human chorionic gonadotropin ("hCG"), heparanase, Her2/neu, human mammary tumor virus ("HMTV"), 70 kiloDalton heat-shock protein ("HSP70"), human telomerase reverse transcriptase ("hTERT"), insulin-like growth factor receptor-1 ("IGFR-1"), interleukin-13 receptor ("IL-13R"), inducible nitric oxide synthase ("iNOS"), Ki67, KIAA0205, K-ras, H-ras, N-ras, KSA, LKLR-FUT, melanoma antigen-encoding gene 1 ("MAGE-1"), melanoma antigen-encoding gene 2 ("MAGE-2"), melanoma antigen-encoding gene 3 ("MAGE-3"), melanoma antigen-encoding gene 4 ("MAGE-4"), mammaglobin, MAP17, Melan-A/melanoma antigen recognized by T-cells-1 ("MART-1"), mesothelin, MIC A/B, MT-MMPs, mucin, testes-specific antigen NY-ESO-1, osteonectin, p15, P170/MDR1, p53, p97/melanotransferrin, PAI-1, platelet-derived growth factor ("PDGF"), μPA, PRAME, probasin, progenipoietin, prostate-specific antigen ("PSA"), prostate-specific membrane antigen ("PSMA"), RAGE-1, Rb, RCAS1, SART-1, SSX-family, STAT3, STn, TAG-72, transforming growth factor-alpha ("TGF-$\alpha$"), transforming growth factor-beta ("TGF-$\beta$"), Thymosin-beta-15, tumor necrosis factor-alpha ("TNF-$\alpha$"), TP1, TRP-2, tyrosinase, vascular endothelial growth factor ("VEGF"), ZAG, p16INK4, and glutathione-S-transferase ("GST").

10. The method of claim 7, wherein the tumor-associated antigen is selected from the group consisting of: carcinoembryonic antigen ("CEA"), mucin, and prostate-specific antigen ("PSA").

11. The method of claim 1, wherein the disease-associated antigen is an infectious disease antigen.

12. The method of claim 11, wherein the infectious disease antigen is a viral antigen.

13. The method of claim 12, wherein the viral antigen is derived from a virus selected from the group consisting of adenovirus, Coxsackievirus, Crimean-Congo hemorrhagic fever virus, cytomegalovirus ("CMV"), dengue virus, Ebola virus, Epstein-Barr virus ("EBV"), Guanarito virus, herpes simplex virus-type 1 ("HSV-1"), herpes simplex virus-type 2 ("HSV-2"), human herpesvirus-type 8 ("HHV-8"), hepatitis A virus ("HAV"), hepatitis B virus ("HBV"), hepatitis C virus ("HCV"), hepatitis D virus ("HDV"), hepatitis E virus ("HEY"), human immunodeficiency virus ("HIV"), influenza virus, Junin virus, Lassa virus, Machupo virus, Marburg virus, measles virus, human metapneumovirus, mumps virus, Norwalk virus, human papillomavirus ("HPV"), parainfluenza virus, parvovirus, poliovirus, rabies virus, respiratory syncytial virus ("RSV"), rhinovirus, rotavirus, rubella virus, Sabia virus, severe acute respiratory syndrome virus ("SARS"), varicella zoster virus, variola virus, West Nile virus, and yellow fever virus.

14. The method of claim 11, wherein the infectious disease antigen is a bacterial antigen.

15. The method of claim 14, wherein the bacterial antigen is derived from a bacterium selected from the group consisting of *Bacillus anthracis*, *Bordetella pertussis*, *Borrelia burgdorferi*, *Brucella abortus*, *Brucella canis*, *Brucella melitensis*, *Brucella suis*, *Campylobacter jejuni*, *Chlamydia pneumoniae*, *Chlamydia trachomatis*, *Chlamydophila psittaci*, *Clostridium botulinum*, *Clostridium difficile*, *Clostridium perfringens*, *Clostridium tetani*, *Corynebacterium diptheriae*, *Enterococcus faecalis*, *Enterococcus faecium*, *Escherichia coli*, enterotoxigenic *Escherichia coli*, enteropathogenic *Escherichia coli*, *Escherichia coli*) 157: 117, *Francisella tularensis*, *Haemophilus influenza*, *Helicobacter pylori*, *Legionella pneumophila*, *Leptospira interrogans*, *Listeria monocytogenes*, *Mycobacterium leprae*, *Mycobacterium tuberculosis*, *Mycoplasma pneumoniae*, *Neisseria gonorrhoeae*, *Neisseria meningitides*, *Pseudomonas aeruginosa*, *Rickettsia rickettsia*, *Salmonella typhi*, *Salmonella typhimurium*, *Shigella sonnei*, *Staphylococcus aureus*, *Staphylococcus epidermidis*, *Staphylococcus saprophyticus*, *Streptococcus agalactiae*, *Streptococcus pneumoniae*, *Streptococcus pyogenes*, *Treponema pallidum*, *Vibrio cholerae*, and *Yersinia pestis*.

* * * * *